(12) United States Patent
Jin et al.

(10) Patent No.: US 9,814,870 B2
(45) Date of Patent: Nov. 14, 2017

(54) NON-LUER CONNECTORS

(75) Inventors: Yun Jin, Bedminster, NJ (US); Yongxian Wu, Beijing (CN); Devesh Mathur, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 24 days.

(21) Appl. No.: 13/210,966

(22) Filed: Aug. 16, 2011

(65) Prior Publication Data
US 2012/0150129 A1 Jun. 14, 2012

Related U.S. Application Data

(60) Provisional application No. 61/374,325, filed on Aug. 17, 2010.

(51) Int. Cl.
A61M 39/10 (2006.01)
(52) U.S. Cl.
CPC ..... *A61M 39/10* (2013.01); *A61M 2039/1094* (2013.01)
(58) Field of Classification Search
CPC .......... A61M 39/10; A61M 2039/1094; A61M 3/00; A61M 3/0279; A61M 5/178; A61M 5/31; A61M 5/3134; A61M 5/346
USPC ............... 604/187, 243, 533, 534, 535, 538; 285/328, 330, 331, 332
See application file for complete search history.

(56) References Cited

U.S. PATENT DOCUMENTS

| 3,043,304 A | 7/1962 | Higgins |
| 3,472,227 A | 10/1969 | Burke |
| 4,538,836 A | 9/1985 | Krutten et al. |
| 4,740,205 A | 4/1988 | Seltzer et al. |
| 5,069,225 A | 12/1991 | Okamura |
| 5,437,650 A | 8/1995 | Larkin et al. |
| 5,484,421 A | 1/1996 | Smocer |
| 5,509,911 A | 4/1996 | Cottone, Sr. et al. |
| 5,545,152 A | 8/1996 | Funderburk et al. |
| 5,569,222 A | 10/1996 | Haselhorst et al. |
| 5,573,516 A | 11/1996 | Tyner |
| 5,616,133 A | 4/1997 | Cardenas |
| 5,616,136 A | 4/1997 | Shillington et al. |

(Continued)

FOREIGN PATENT DOCUMENTS

| AU | 2010202231 B2 | 1/2011 |
| CA | 2483178 A1 | 11/2003 |

(Continued)

OTHER PUBLICATIONS

Non-Final Office Action in U.S. Appl. No. 13/210,767, dated Jul. 19, 2013, 13 pgs.

(Continued)

*Primary Examiner* — Kami A Bosworth
(74) *Attorney, Agent, or Firm* — Servilla Whitney LLC

(57) ABSTRACT

Drug delivery devices having integrated non-luer connectors are described. An exemplary drug delivery device includes a container with a non-luer connector that prevents connection of a standard female luer connector to the container. One or more embodiments pertain to a container with a non-luer connector that prevents the formation of a fluid-tight seal between a standard female luer connector and the container. A non-luer connector for attachment to a container having a non-luer element is also described.

12 Claims, 45 Drawing Sheets

(56) References Cited

U.S. PATENT DOCUMENTS

| | | | |
|---|---|---|---|
| 5,968,020 A | 10/1999 | Saito | |
| 6,050,978 A | 4/2000 | Orr et al. | |
| 6,273,870 B1 | 8/2001 | Garvin | |
| 6,402,207 B1 | 6/2002 | Segal | |
| 6,500,153 B1 | 12/2002 | Sheppard et al. | |
| 6,599,269 B1 | 7/2003 | Lewandowski et al. | |
| 6,612,624 B1 | 9/2003 | Segal et al. | |
| 7,040,598 B2 | 5/2006 | Raybuck | |
| 7,137,654 B2 | 11/2006 | Segal | |
| 7,306,566 B2 | 12/2007 | Raybuck | |
| 7,651,481 B2 | 1/2010 | Raybuck | |
| 7,873,402 B2 | 1/2011 | Schachar et al. | |
| 2003/0212372 A1* | 11/2003 | Bills et al. | 604/236 |
| 2005/0251096 A1* | 11/2005 | Armstrong | A61M 5/14546 604/218 |
| 2006/0033331 A1 | 2/2006 | Ziman | |
| 2006/0047251 A1* | 3/2006 | Bickford Smith | A61M 39/10 604/240 |
| 2007/0060898 A1* | 3/2007 | Shaughnessy et al. | 604/284 |
| 2007/0076401 A1 | 4/2007 | Carrez et al. | |
| 2007/0179454 A1 | 8/2007 | Ziman et al. | |
| 2007/0260195 A1 | 11/2007 | Bartholomew et al. | |
| 2008/0045929 A1 | 2/2008 | Birnbach | |
| 2008/0103486 A1 | 5/2008 | Owens | |
| 2008/0132851 A1 | 6/2008 | Shaw et al. | |
| 2008/0312640 A1 | 12/2008 | Grant | |
| 2008/0319422 A1 | 12/2008 | Cardenas | |
| 2009/0099552 A1 | 4/2009 | Levy et al. | |
| 2009/0326481 A1 | 12/2009 | Swisher et al. | |
| 2010/0286558 A1 | 11/2010 | Schraga | |
| 2012/0245564 A1 | 9/2012 | Tekeste | |

FOREIGN PATENT DOCUMENTS

| | | |
|---|---|---|
| CA | 2588888 A1 | 6/2006 |
| CA | 2612094 A1 | 12/2006 |
| CA | 2692157 A1 | 12/2008 |
| CA | 2735146 A1 | 3/2010 |
| CN | 1299686 A | 6/2001 |
| DE | 102006050212 | 4/2008 |
| EP | 0716860 | 6/1996 |
| EP | 2269685 | 1/2011 |
| FR | 2928552 | 9/2009 |
| JP | S58-13216 | 1/1983 |
| JP | H09-507779 | 8/1997 |
| JP | 2002500935 A | 1/2002 |
| JP | 2007-098106 | 4/2007 |
| JP | 2007-512855 | 5/2007 |
| JP | 2001-187141 | 7/2007 |
| JP | 2009544345 A | 12/2009 |
| WO | WO-99/37356 | 7/1999 |
| WO | WO-2008/009946 | 1/2008 |
| WO | WO-2009/144583 | 12/2009 |
| WO | WO-2010/064074 | 6/2010 |

OTHER PUBLICATIONS

PCT International Search Report & Written Opinion in PCT/US2011/048034, dated Feb. 19, 2013, 6 pgs.
PCT International Search Report & Written Opinion in PCT/US2011/048034, dated Dec. 15, 2011, 11 pgs.
PCT International Search Report & Written Opinionin PCT/US2011/048057, mailed Dec. 14, 2011, 12 pgs.
Final Office Action in U.S. Appl. No. 13/210,767, dated Nov. 25, 2013, 9 pgs.
International Preliminary Report on Patentability and Written Opinion in PCT/US2011/048057, dated Oct. 10, 2013, 8 pages.
Non-Final Office Action in U.S. Appl. No. 13/210,767, dated Nov. 18, 2014, 12 pages.
Non-Final Office Action in U.S. Appl. No. 13/210,767, dated Dec. 21, 2015, 14 pages.
Final Office Action in U.S. Appl. No. 13/210,767, dated Mar. 27, 2015, 10 pages.
Non-Final Office Action in U.S. Appl. No. 15/230,861 dated Dec. 8, 2016, 34 pages.
Extended European Search Report in 16204426.7 dated May 2, 2017, 10 pages.
Non-Final Office Action in U.S. Appl. No. 15/230,861 dated Jun. 6, 2017, 28 pages.

* cited by examiner

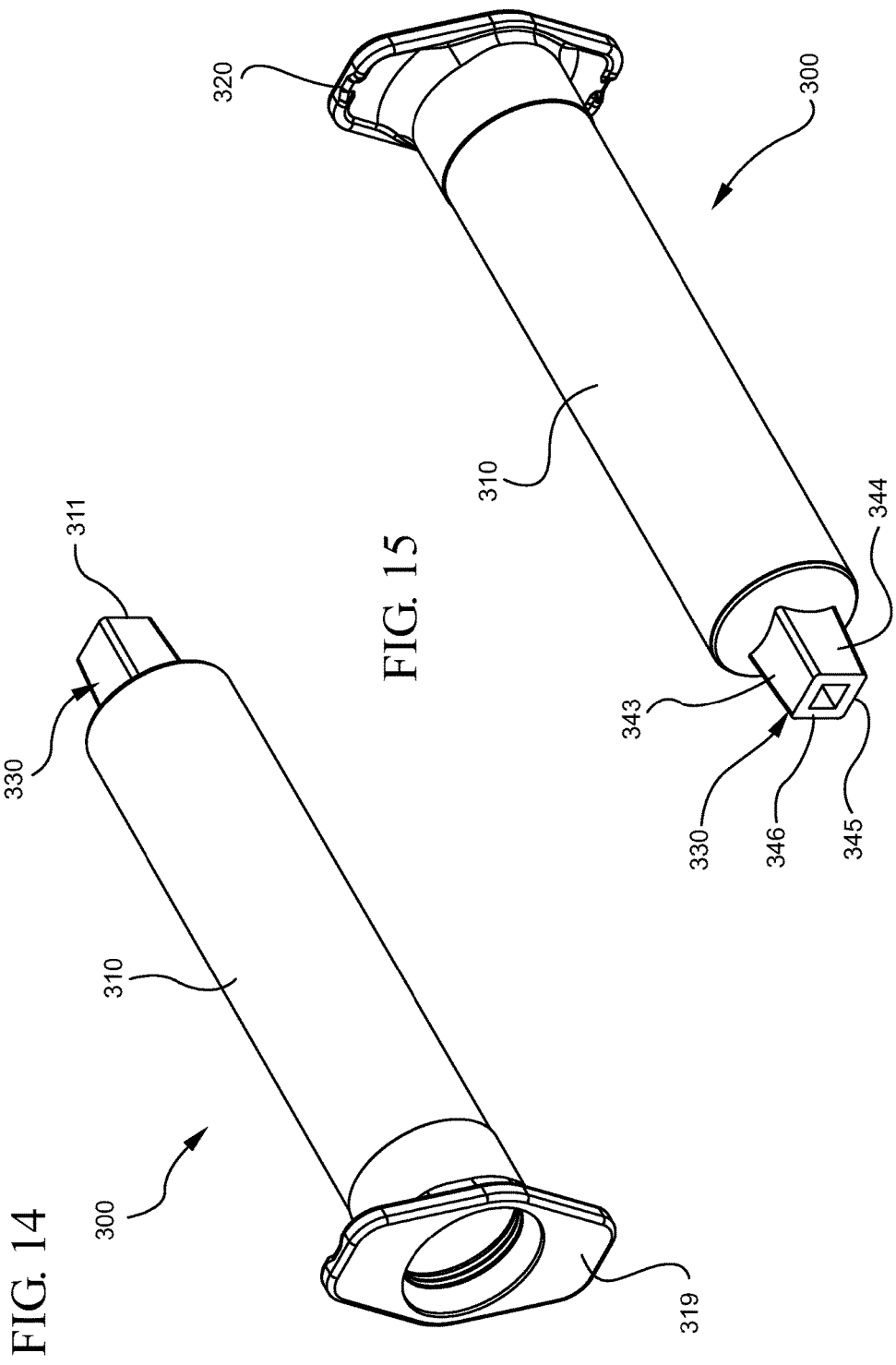

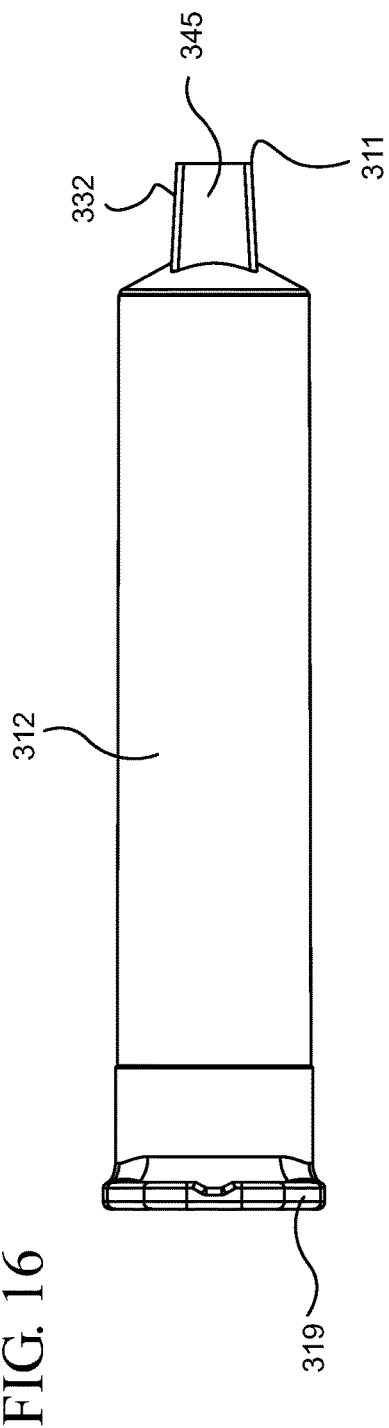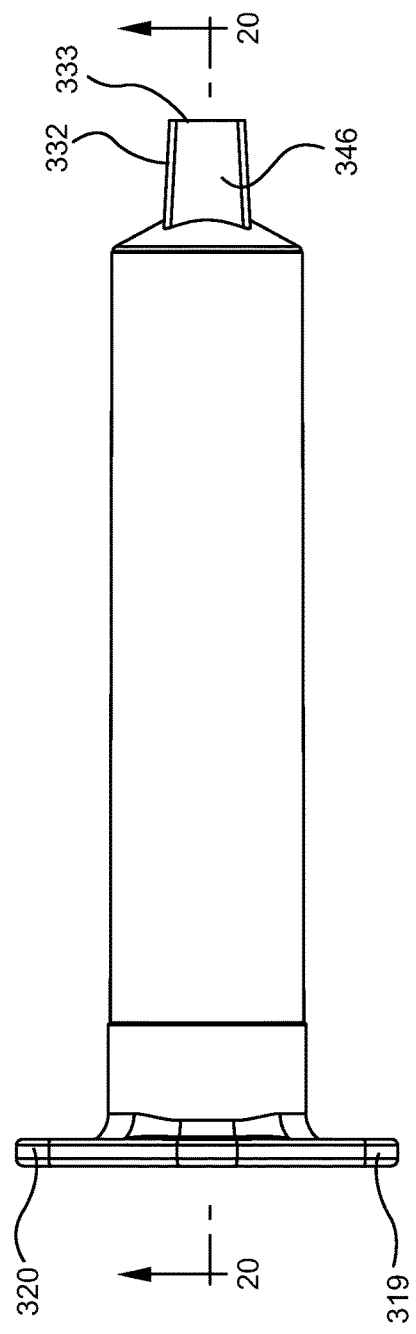

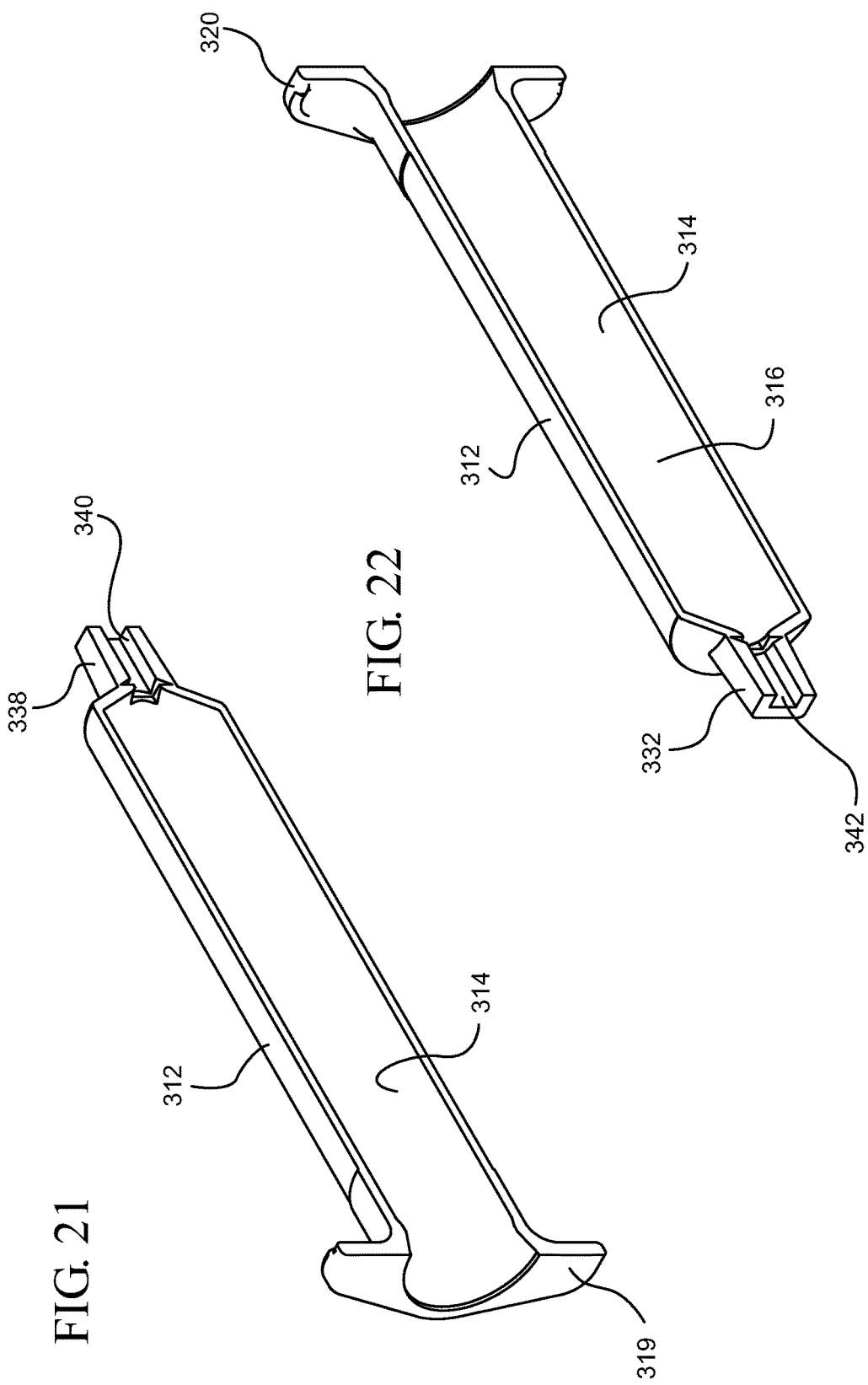

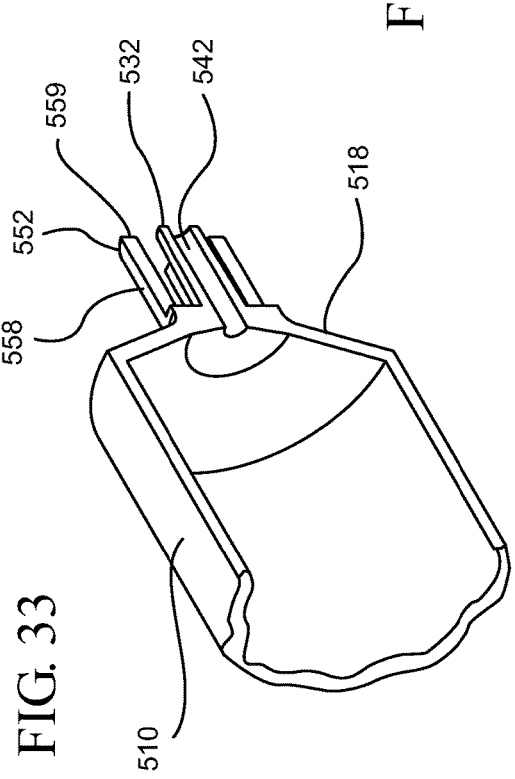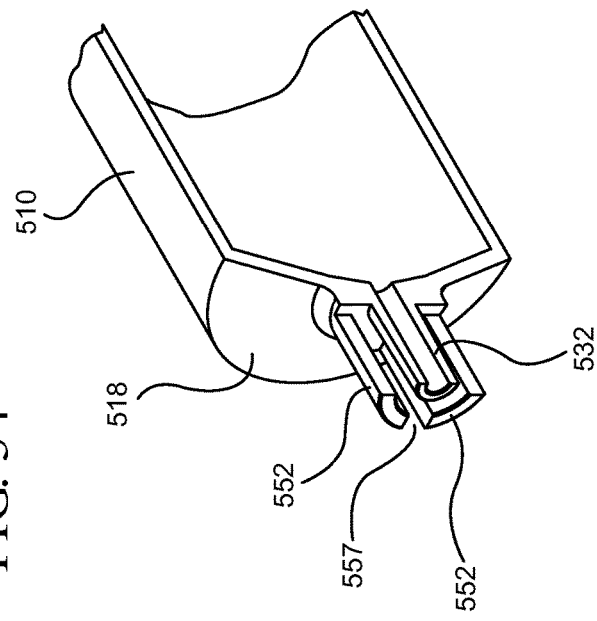

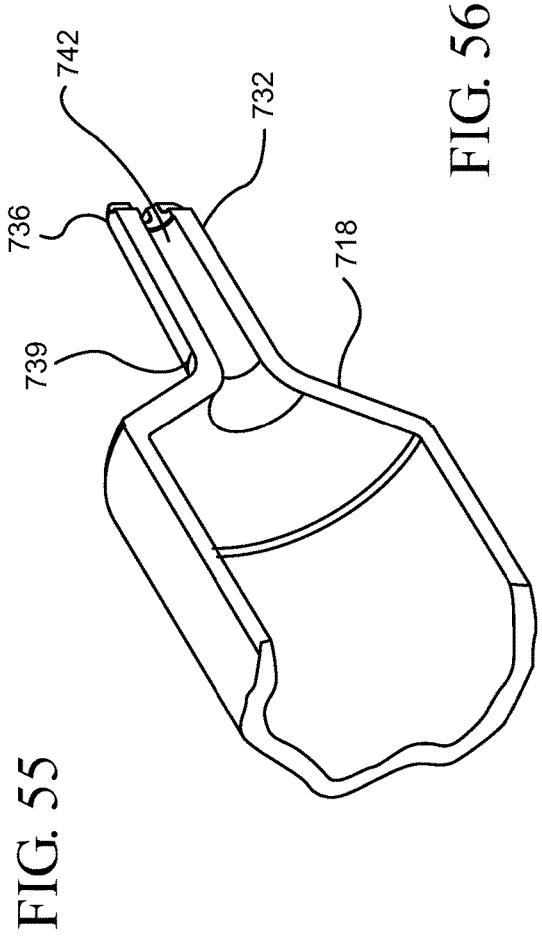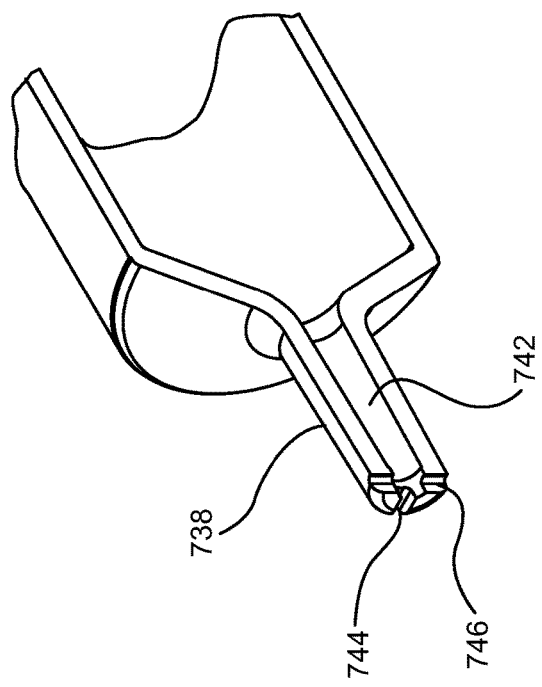

NON-LUER CONNECTORS

CROSS-REFERENCE TO RELATED APPLICATIONS

This application claims priority under 35 U.S.C. §119(e) to U.S. Provisional Application No. 61/374,325, filed Aug. 17, 2010, the disclosures of which are incorporated herein by reference in their entirety.

TECHNICAL FIELD

Aspects of the present invention relate to non-luer connectors for use with drug delivery systems that prevent misconnection with standard male and female luer connectors.

BACKGROUND

Connectors used with drug delivery devices typically share a common ISO standard luer connection. A standard luer tip or standard male connector has specifications as provided by the International Organization for Standardization (ISO) in ISO 594-1:1986 and 594-2:1998, including a 6% taper that increases from the open distal end to the proximal end and an outer cross-sectional diameter at the distal end of the tip measuring between about 0.1545 inches (3.925 mm) and about 0.1570 inches (3.990 mm) for rigid material and between about 0.1545 inches (3.925 mm) and about 0.1585 inches (4.027 mm) for semi-rigid material. A standard luer hub or standard female luer connector may have a 6% taper that decreases from the open proximal end to the distal end and an inner cross-sectional dimension at the open proximal end measuring between about 0.168 inches (4.270 mm) to about 0.170 inches (4.315 mm). In embodiments of standard female luer connectors that incorporate tabs or lugs for connection to a corresponding male luer lock connector, the outer cross-sectional dimension of the standard female luer connector, including the lugs, is in the range from about 0.307 inches (7.80 mm) to about 0.308 inches (7.83 mm). In embodiments of standard female luer connectors that do not incorporate tabs or lugs for connection to a corresponding male luer lock connector, the outer cross-sectional dimension may be about 0.224 inches (5.700 mm) for rigid connectors and about 0.265 inches (6.730 mm) for semi-rigid connectors, based on the maximum outside diameter of the standard female luer connector at the base of the lugs of ISO 594-2. The minimum length of the standard luer tip and/or the standard luer hub is 0.295 inches (7.500 mm), according to ISO 594-1. As used herein, the phrases "standard male luer connector" and "standard female luer connector" shall refer to connectors having the above dimensions.

Standard luer male connectors and standard female connectors, collectively referred to herein as standard luer connectors, may be used in intravascular, anesthesia and enteral delivery systems and may include structure that allows a drug delivery device for one system to be to be compatible with other systems. For example, some neuraxial drug delivery systems may use the same type of standard luer connector as the connectors used with other delivery applications, for example, central intravenous catheters, central venous pressure parts, infusion ports, balloon ports, introducer ports, IV luer connectors, peritoneal dialysis catheters, distal port for a pulmonary artery catheter, and many other connectors. An unintended consequence of connecting a drug delivery system for one type of delivery system to connectors for use with other types of delivery systems is that such connection would provide a link between two unrelated systems, i.e., neuraxial to intravenous (IV). Each delivery system is intended to provide unique methods of delivery, with distinctly different purposes and different medications, which the interchangeability of known drug delivery systems can circumvent. Such circumvention can lead to harm and/or serious injury to the patient.

Limiting the use of standard luer connectors for vascular access or systems is one consensus accepted by device manufacturers and regulatory bodies. Accordingly, there has been a need to modify all other devices so they have a different type of connector that cannot physically connect with a standard luer connector or incompatible devices. New proposed standards for small bore connectors, for example ISO 80369-6 for neuraxial applications, have also propelled the need for suitable non-luer connectors. These new proposed standards include connectors with a 5% taper, instead of a 6% taper that is currently used with standard luer connectors. In addition, the new standards propose connectors with smaller inner and outer cross-sectional dimensions and longer lengths than standard luer connectors.

Attempts to prevent or minimize misconnections between drug delivery systems include educating practitioners about misconnections, labeling and color-coding. However, these attempts offer only temporary solutions. The use of adapters which provide a removable non-luer adapter also does not provide a permanent solution that is free of or reduces human error. Other solutions require the use of adapters to enable users to fill the medication to be administered into the drug delivery system because the drug delivery system is not compatible with standard ampoules, vials or other containers.

There is a need for non-luer connectors for use with drug delivery systems that prevent misconnection with standard luer connectors and other unintended drug delivery systems.

SUMMARY

In this disclosure, a convention is followed wherein the distal end of the device is the end closest to a patient and the proximal end of the device is the end away from the patient and closest to a practitioner.

As used herein, the term "dimension" shall include the length, diameter or width of a geometric shape or the geometrically shaped components described herein. The term "cross-sectional dimension" shall include the measurement of the longest distance or greatest distance between two points on an edge of a cross-section of an object or component with a circular or non-circular cross-section. The two points may be located on the inside surface or outside surface of the edge of the cross-section of the object. The cross-sectional dimension of two points located on the inside surface of the edge of the cross-section of the object shall be referred to as the "inside cross-sectional dimension" and the cross-sectional dimension of two points located on the outside surface of the edge of the cross-section of an object shall be referred to as the "outside cross-sectional dimension." It should be recognized that "cross-sectional dimension" of objects having a circular cross-section may be referred to as the "diameter" of the object. The terms "cross-sectional dimension" and "diameter" may be used interchangeably for objects having a circular cross-section.

The drug delivery systems of one or more embodiments described herein may be used for neuraxial, anesthesia, intravascular or other drug delivery applications.

A first aspect of the present invention pertains to a non-luer connector for connection to a second non-luer connector. In one or more embodiments, the non-luer connector includes a container including an open distal end including a distal wall and a sidewall extending in a proximal direction from the distal wall. The sidewall includes an inside surface defining a fluid chamber for retaining fluids. The container also includes an elongate tip extending in a distal direction from the distal wall. The elongate tip includes an opening providing access to the chamber, an outside surface and a distal end.

In one or more embodiments, the outside surface of the elongate tip includes an outer cross-sectional dimension measured at the distal end of the tip of 0.1545 inches or less. In one or more specific embodiments, the outer cross-sectional dimension of the elongate tip measured at the distal end of the tip is in the range from about 0.100 inches to about 0.145 inches. In an even more specific embodiment, the outer cross-sectional dimension of the elongate tip measured at the distal end of the elongate tip is in the range from about 0.1306 inches to about 0.1326 inches.

The elongate tip of one or more embodiments may have a length, measured from the distal wall of the container to the distal end of the elongate tip in the range from about 0.200 inches to about 0.500 inches.

The outside surface of the elongate tip may have a taper of less than 6% that decreases in a proximal to distal direction. In one or more specific embodiments, the taper of the outside surface may be in the range from about 3% to about 5.9%.

In one or more embodiments, the outside surface of the elongate tip may have a taper of more than 6% that decreases in a proximal to distal direction.

The non-luer connector of one or more embodiments may further include a female non-luer connector that is removably attached to the elongate tip of the container. In one or more embodiments, the female non-luer connector includes a hub body with an open proximal end and an interior surface defining a cavity. The hub body may optionally include a needle cannula attached thereto. The needle cannula may include an open proximal end in fluid communication with the opening of the container.

In one or more embodiments, the cavity of the hub body may have an inner cross-sectional dimension measured at the open proximal end of less than 0.168 inches, measured at the open proximal end. In one or more specific embodiments, the cavity of the hub body may have an inner cross-sectional dimension at a proximal end in the range from about 0.110 inches to about 0.150 inches. In an even more specific embodiment, the cavity of the hub body has an inner cross-sectional dimension measured at the open proximal end in the range from about 0.1417 inches to about 0.1437 inches.

The cavity of one or more embodiments of the female non-luer connector may have a length in the range from about 0.250 inches to about 0.500 inches.

In one or more embodiments, the interior surface of the cavity has taper of less than 6% decreasing in a proximal to distal direction. In one or more specific embodiments, the interior surface of the cavity has a taper decreasing in a proximal to distal direction in the range from about 3% to about 5.9%, or alternatively, in the range from about 0.5% to about 2.9%.

In one or more embodiments, the interior surface of the cavity has taper of more than 6% decreasing in a proximal to distal direction.

In one or more embodiments, the elongate tip of the container may include a square cross-sectional shape. In one or more specific embodiments, the outside surface of the elongate tip may include a square cross-sectional shape. The cavity of the female non-luer connector of one or more embodiments may have an interior surface having a square cross-sectional shape. The female non-luer connector may also have an inner cross-sectional dimension selected to form a fluid-tight seal with the elongate tip, or more specifically, the outside surface of the elongate tip. In one or more alternative embodiments, the elongate tip may have a circular cross-sectional shape. The cavity of the female non-luer connector may have an inner cross-sectional dimension selected to form a fluid-tight seal with the elongate tip. Specifically, the shape and/or size of the inner cross-sectional dimension of the cavity may be selected to form a fluid-tight seal with the outside surface of the elongate tip.

A second aspect of the present invention pertains to a non-luer connector for connection to a female non-luer connector that includes a non-luer element. In one or more embodiments, the non-luer connector includes a container having an open distal end including a distal wall and a sidewall that extends in a proximal direction from the distal wall. The sidewall may include an inside surface that defines a fluid chamber for retaining fluids. The container may also include an elongate tip that extends in a distal direction from the distal wall. The elongate tip includes an opening for providing access to the chamber. In one or more embodiments, a non-luer element is disposed at the open distal end of the container for preventing fluid-tight connection of a standard luer connector to the container.

In one or more embodiments, the elongate tip includes an outside surface on which the non-luer element may be disposed. The non-luer element of one or more variants may include an exterior surface with an outer cross-sectional dimension that is greater than the outer cross-sectional dimension of the elongate tip. The outer cross-sectional dimension of the non-luer element may also be greater than an inner cross-sectional dimension of a standard female luer connector. The outer cross-sectional dimension of the non-luer element may prevent connection of a standard female luer connector to the elongate tip. In one or more alternative embodiments, the exterior surface of the non-luer element has one of a circular cross-sectional shape, a square cross-sectional shape and a triangular cross-sectional shape.

Embodiments of the non-luer connector according to the second aspect may include a female non-luer connector being removably attached to the elongate tip of the container, as otherwise described herein. In one or more embodiments, the female non-luer connector may have a cavity with cross-sectional dimension selected to form a fluid-tight seal with the elongate tip or, more specifically, with the outside surface of the tip.

In one or more embodiments, the non-luer element extends in a distal direction from the distal wall of the container. The non-luer element may be disposed coaxially around the elongate tip and form a channel between the elongate tip and the non-luer element for receiving a portion of a female non-luer connector. In one or more variants, the inner cross-sectional dimension of the non-luer element may be greater than an inner cross-sectional dimension of a standard female luer connector and less than an outer cross-sectional dimension of the standard female luer connector. In one or more alternative embodiments, the non-luer element has one of a circular cross-section, a square cross-section and a triangular cross-section. The non-luer element of one or more embodiments may include at least one aperture that provides access to the channel. In one variant, the non-luer element includes at least two apertures and includes a curved cross-sectional shape between the two apertures. In another variant, the non-luer element includes a distal end and a proximal end and the at least one or two apertures extends from the distal end to the proximal end of the non-luer element. In yet another variant, the at least one or two apertures extends from the distal end to a distance partially between the distal end and the proximal end of the non-luer element. The aperture or apertures provided in one or more embodiments may provide visual indication of whether the non-luer connector comprises a luer slip fitting or a luer lock fitting. The non-luer connector of one or more embodiments may incorporate an at least one aperture that has a dimension selected to prevent formation of a fluid-tight seal between the non-luer element and a standard female luer connector. In one variant, the distal end of the non-luer element extends distally past the elongate tip. In another variant, the elongate tip includes a distal end that extends distally past the distal end of the non-luer connector.

In one or more embodiments in which the non-luer element is disposed coaxially around the elongate tip, the non-luer connector may include a female non-luer connector removably attached to the elongate tip of the container, as described herein. In one or more embodiments, the female non-luer connector may include a hub body and a cavity dimensioned for fluid-tight connection of the female non-luer connector to the elongate tip. In one or more embodiments, the cavity of the female non-luer connector may have a cross-sectional dimension selected to form a fluid-tight seal with the elongate tip.

In one or more embodiments, the non-luer element may be provided on the non-luer connector at a distal end of the elongate tip. The non-luer element may be disposed at the distal end of the elongate tip for preventing the formation of a fluid tight seal between the elongate tip and a standard female luer connector. In one or more embodiments, the elongate tip may include a body wall with an outside surface extending from the distal end to the distal wall of the container and the non-luer element includes a notch in fluid communication with the opening of the elongate tip for extending the opening across the distal end of the elongate tip to the outside surface of the body wall of the elongate tip. In one or more specific embodiments, the non-luer element includes a plurality of notches disposed on the distal end of the elongate tip. The plurality of notches may be disposed adjacent to one another along the circumference of the distal end of the tip and may surround the opening of the tip. In one or more variants, the plurality of notches having a wedge shape that extends into the distal end of the elongate tip. The length of the elongate tip may vary along the plurality of notches. Specifically, the elongate tip may have a length that increases along the distal end from the opening of the tip to the outside surface of the tip. In one or more embodiments, the outside surface of the elongate tip has a taper of 5% decreasing in a proximal to distal direction. The tip may also have an outer cross-sectional dimension sized to prevent connection of a standard female luer connector to the container.

Embodiments of the non-luer connector that includes a notch, notches or a plurality of notches may include a female non-luer connector being removably attached to the elongate tip, as otherwise described above. The female non-luer connector may include an interior surface defining a cavity dimensioned for fluid-tight connection of the female non-luer connector to the elongate tip. In one or more embodiments, upon attachment of the female non-luer connector to the container, the notch may be in contact with the interior surface of the hub body and a fluid-tight seal is formed between the distal end of the elongate tip and the female non-luer connector. In one or more alternative embodiments, upon attachment of a standard female luer connector to the container, the notch is disposed at a distance from an inside surface of the standard female luer connector, preventing formation of a fluid-tight seal between the distal end of the elongate tip and the standard female luer connector. The interior surface of the female non-luer connector may have a 5% taper that decreases in a proximal to distal direction. In one or more alternative embodiments, the non-luer element further includes at least one aperture that provides access to the channel.

A third aspect of the present invention pertains to a drug delivery device that includes a container and a female non-luer connector. In one or more embodiments, the container includes an open distal end including a distal wall and a sidewall extending in the proximal direction from the distal wall. The sidewall includes an inside surface defining a fluid chamber for retaining fluids. An elongate tip is disposed on the distal wall and extends in a distal direction from the distal wall. The elongate tip includes an opening for providing access to the chamber and an inside surface including a taper of less than 6% decreasing in a proximal to distal direction. The elongate tip may have an outer cross-sectional dimension sized to prevent connection of a standard female luer connector to the container. The female non-luer connector may include a hub body including an open proximal end and an interior surface defining a cavity. The interior surface of the hub body may have a taper of less than 6% decreasing in a proximal to distal direction. The cavity may have an inner cross-sectional dimension that is sized to prevent connection of the female non-luer connector to a standard female luer connector. The hub body may optionally include a needle cannula attached to the hub body that includes an open distal end in fluid communication with the opening of the container.

The drug delivery device of one or more embodiments may include a visual indicator for providing indication that a fluid-tight seal is formed between the female non-luer connector and the container and the needle cannula is in fluid communication with the opening of the container.

BRIEF DESCRIPTION OF THE DRAWINGS

FIG. 14 illustrates a perspective view from a proximal end of a container according to one or more embodiments of the present invention;

FIG. 15 illustrates a perspective view from a distal end of the container shown in FIG. 14;

FIG. 16 illustrates a side elevational view of the container shown in FIG. 14;

FIG. 17 illustrates a side elevational view of the container shown in FIG. 16, after rotating the container 90 degrees;

FIG. 21 illustrates a perspective view of the container shown in FIG. 17 taken from the proximal end;

FIG. 22 shows a perspective view of the container shown in FIG. 17 taken from the distal end;

FIG. 33 illustrates a perspective view of the container shown in FIG. 37 taken from the proximal end;

FIG. 34 illustrates a partial enlarged view of the distal end container of FIG. 33;

FIG. 55 illustrates a perspective view of the container shown in FIG. 54 taken from the proximal end;

FIG. 56 shows a perspective view of the container shown in FIG. 54 taken from the distal end;

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Figure 1:
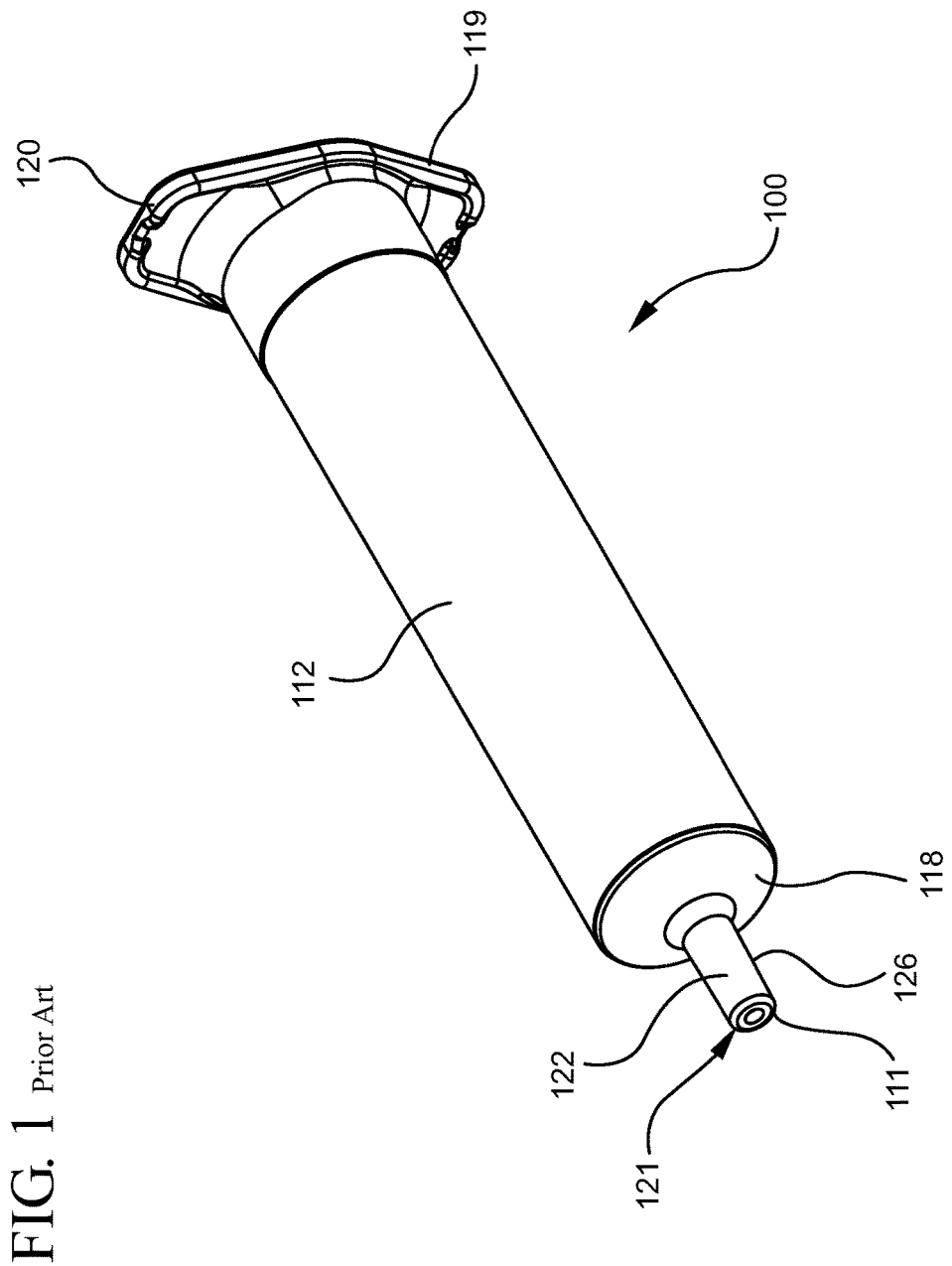
FIG. 1 shows a perspective view of the syringe barrel having a standard male luer connector according to the prior art.
Figure 2:
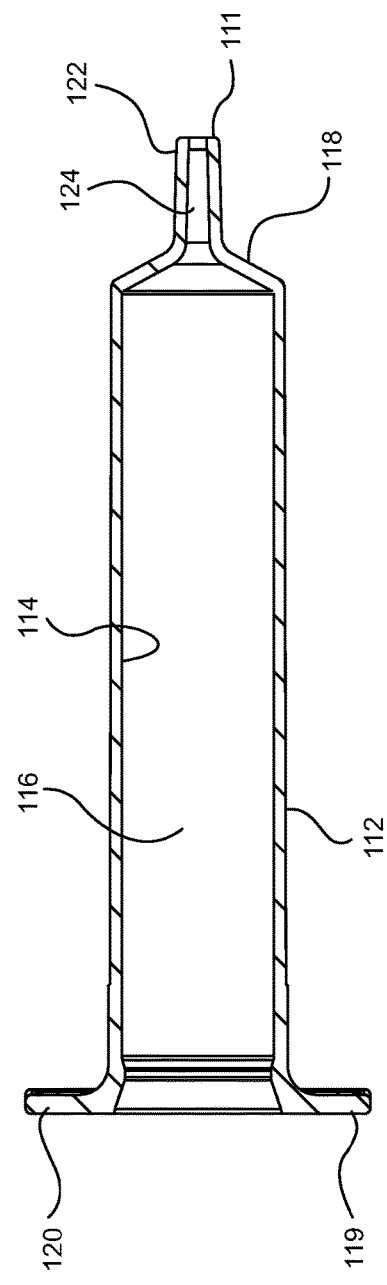
FIG. 2 illustrates a cross-sectional side view of the syringe barrel and standard male luer connector of FIG. 1.
Figure 3:
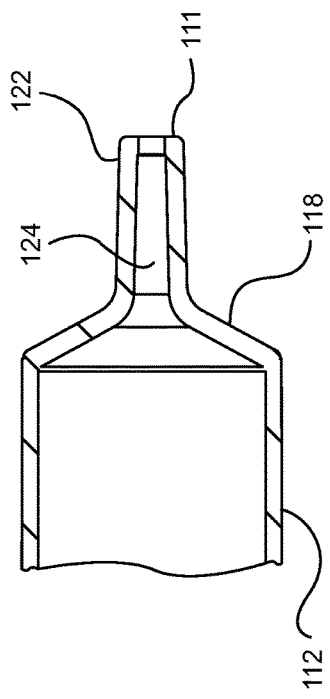
FIG. 3 illustrates an enlarged view of the standard male luer connector of FIG. 2.

Aspects of the present invention pertain to non-luer connectors that prevent misconnection to other incompatible or unintended standard luer connectors. A non-luer connector shall be defined herein as a connector that has a shape, dimension or structure that differs from standard luer connectors, as defined above. A non-luer connector shall also include a connector that has a shape, dimension or structure that prevents it from being characterized or defined as a luer connector as defined above or according ISO 594-1:1986 or ISO 594-2:1998. In one or more specific embodiments, a non-luer connector has a length and/or cross-sectional dimension that differs from a luer connector as defined above or according ISO 594-1:1986 or ISO 594-2:1998. In a more specific embodiment, a non-luer connector has a taper that differs from a luer connector as defined above or according ISO 594-1:1986 or ISO 594-2:1998. In an even more specific embodiment, a non-luer connector has a more gentle taper than a luer connector as defined above or according ISO 594-1:1986 or ISO 594-2:1998, a cross-sectional dimension that is smaller than a luer connector as defined above or according ISO 594-1:1986 or ISO 594-2:1998 and a longer length than a luer connector as defined above or according ISO 594-1:1986 or ISO 594-2:1998. Specifically, the embodiments of the non-luer connectors described herein incorporate features that prevent connection of standard luer connectors to the non-luer connectors. Standard luer connectors, as used herein, may include needle hubs, syringes or other delivery components that incorporate a standard luer connector. Exemplary standard luer connectors are shown in FIGS. 1-4. FIG. 1 illustrates a syringe barrel 100 having distal end 111 and a proximal end 119. The syringe barrel 100 includes a sidewall 112 that extends from the distal end 111 to the proximal end 119 and includes an inside surface 114 defining a chamber 116 for retaining fluids. The syringe barrel 100 also includes a distal wall 118 adjacent to the distal end 111 and a flange 120 disposed at the proximal end 119 of the syringe barrel. A luer connector 121 is provided in the form of an open tip 122 that extends from the distal wall 118 and includes a passageway 124 in fluid communication with the chamber 116. The tip 122 includes an outside surface 126 that defines an outer cross-sectional dimension and length that is typical of standard male luer connectors.

Figure 4:
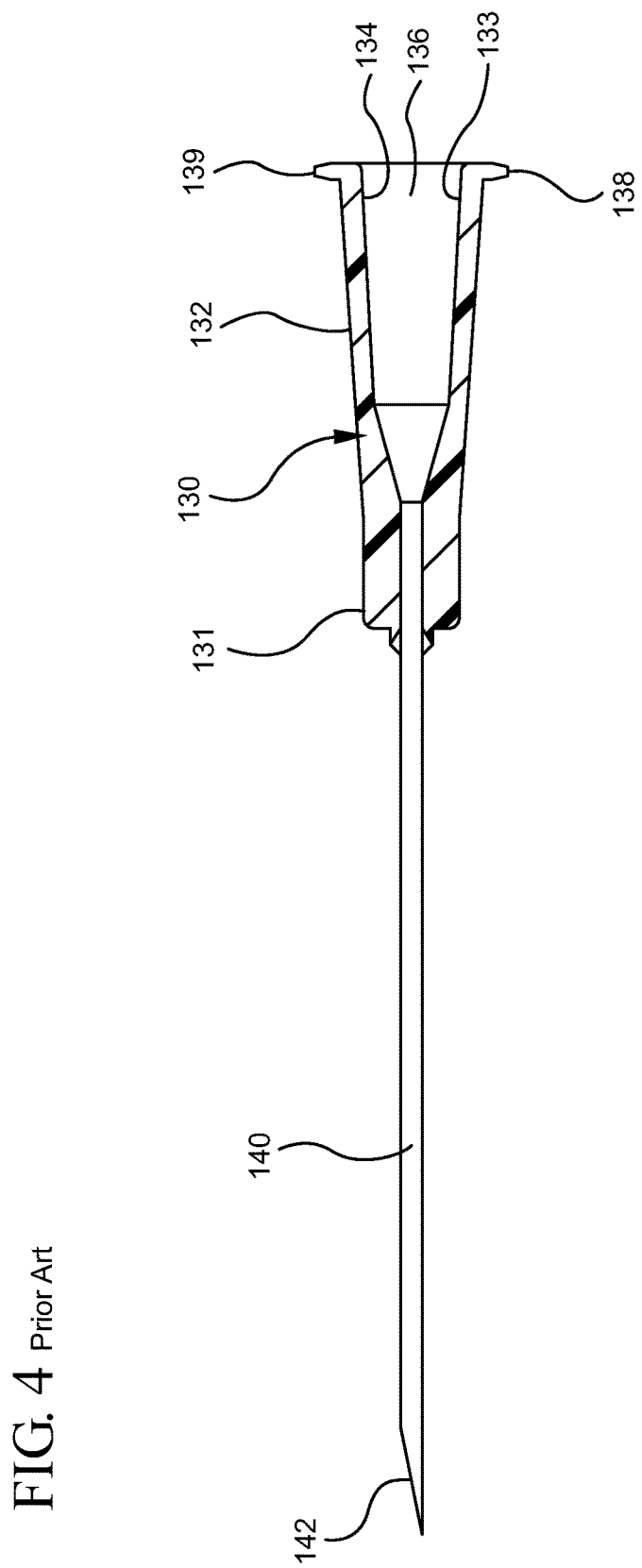
FIG. 4 illustrates a cross-sectional side view of a needle hub having a standard female luer connector according to the prior art.

An exemplary standard needle hub 130 having a standard female luer connector is shown in FIG. 4. The needle hub 130 includes an open distal end 131 and an open proximal end 139. A hub body 132 extends from the distal end 131 to the proximal end 139. In the embodiment shown, the luer connector 133 is provided in the form of a hub body 132 that includes an inside surface 134 defining a cavity 136. The cavity 136 is sized and has a shape to permit fluid-tight engagement with the tip 122 of the syringe barrel. The needle hub 130 shown in FIG. 4 also includes a needle cannula 140 attached to the open distal end 111. The needle cannula 140 includes an open distal end 142 in fluid communication with the cavity 136. The inside surface 134 of the hub body 132 has an inner cross-sectional dimension and length that is typical of standard female luer connectors.

Both of the standard luer connectors of the syringe barrel 100 and the needle hub 130 are sized and shaped form an interference fit connection and/or fluid-tight engagement with each other. Specifically, the outside surface of the tip 122 has a taper, length and shape that is typical of standard male luer connectors, as described above, that permits the tip 122 to form an interference fit connection with the inside surface of the needle hub 130, which also has a taper, length and shape that is typical of standard female luer connectors, as also described above. In one or more alternative embodiments, the syringe barrel 100 may include a standard male luer connector in the form of a luer lock connector (not shown), which includes a threaded portion that engages a cooperating structure of the needle hub 130, for example, as shown in FIG. 4, the outwardly extending tab 138, to attach the needle hub 130 to the syringe barrel 100.

A first aspect of the present invention pertains to non-luer connectors which have a dimension and/or shape or incorporate a feature that prevent connection of the non-luer connectors to standard luer connectors. A second aspect of the present invention includes non-luer connectors that utilize a non-luer element to prevent connection to standard luer connectors. A third aspect of the present invention includes non-luer connectors that prevent the formation of a fluid-tight connection between the non-luer connectors and a standard luer connector thereby causing leakage or increasing the possibility of leakage of liquid at the connection.

One or more embodiments of a female non-luer connector 200 are shown in FIGS. 5-13 that may be utilized as part of the drug delivery devices according to the first aspect, second aspect and the third aspects of the present invention. Specifically, the female non-luer connector 200 includes a non-luer portion 230 that may be connected to a non-luer connector of the containers that will be described below.

The female non-luer connector 200 includes an open distal end 201 and an open proximal end 209. The female non-luer connector 200 also includes a non-luer portion 230 for forming an interference fit connection with a corresponding non-luer connector. The non-luer portion 230 is an integral component of the female non-luer connector 200 and is provided in the embodiment shown in FIGS. 5-13 as a wall 212 that extends distally from the open proximal end 209 of the female non-luer connector 200. The wall 212 includes an inside surface 214 defining a cavity 216 for receiving at least a portion of a corresponding non-luer connector. The female non-luer connector 200 includes an outside surface 203 with a radially outwardly extending rim 218 is disposed along the entire circumference of the outside surface 203 at the distal end 201 of the female non-luer connector 200. The rim 218 in the embodiment shown in FIGS. 5-13 includes a radially outwardly extending tab 220 disposed along at least a portion of the rim 218 for engaging corresponding non-luer connectors with a locking feature or threaded component. The tab 220 may include two tapered ends for facilitating engagement with the locking feature or threaded component. The rim 218 includes an inside surface 219 that has a cross-sectional diameter that is greater than the cross-sectional diameter of the remainder of the female non-luer connector 200.

The inside surface 214 of the wall 212 that has a dimension and/or shape that enables engagement or attachment of the female non-luer connector 200 with other corresponding non-luer connectors. As will be described below, corresponding non-luer connectors include an outside surface with an outer cross-sectional dimension that is smaller or larger than the inner cross-sectional dimension measured at the inside surface 134 of standard female luer connectors. The outer cross-sectional dimension of the corresponding non-luer connectors, however, is sized and/or shaped to properly engage the inside surface 214 of the female non-luer connector 200 shown in FIGS. 5-13 to produce a fluid-tight connection.

In one or more embodiments, the inside surface 214 of the wall 212 may be shaped to form a fluid-tight engagement with a corresponding non-luer connector having a non-circular cross-section. Specifically, the inside surface 214 of the wall 212 may have a square, triangular or other non-circular cross-section that permits the formation of an interference fit connection and/or fluid-tight engagement with a non-luer connector with an outside surface having a square, triangular or other non-circular cross-section.

In addition, the inside surface 214 of the wall 212 has a dimension and/or shape that prevents engagement of the female non-luer connector 200 to a standard male luer connector. Specifically, the inside surface 214 of the wall 212 may have a square, triangular or other non-circular cross-section that prevents the formation of an interference fit connection and/or fluid-tight engagement with a standard male luer connector, for example, the tip 122 having an outside surface 126 with a circular cross-section. In embodiments where the inner cross-sectional dimension of the wall 212 is sized to permit the tip 122 or standard male connector of a typical luer connector to be disposed within the cavity 216, the non-circular cross-sectional shape of the wall 212 at the inside surface 214 prevents sufficient contact between the outside surface 126 of the tip and, thereby, prevents formation of an interference fit connection and/or fluid-tight engagement there between. In one or more embodiments, the inner cross-sectional dimension of the wall 212 may be greater than the outer cross-sectional dimension of the tip 122 or other standard male luer connector, which also prevents sufficient contact between the outside surface 126 of the tip or other luer connector and, thereby, prevents formation of an interference fit connection and/or fluid-tight engagement there between.

In the embodiment shown, the attachment end 210 also includes a first narrowed wall 222 extending from the wall 212 to a second narrowed wall 224 disposed distally adjacent to the first narrowed wall 222. A third narrowed wall 226 is disposed distally adjacent to the second narrowed wall 224 and extends to the proximal end 209 of the female non-luer connector 200. The inner cross-sectional dimension of the first narrowed wall 222 is less than the inner cross-sectional dimension of the wall 212 measured at its inside surface. The first narrowed wall 222 may have a taper or an inner cross-sectional dimension that decreases in the distal direction. The inner cross-sectional dimension or shape of the first narrowed wall 222 may also prevent attachment of the female non-luer connector 200 to a standard male luer connector.

Figure 11:
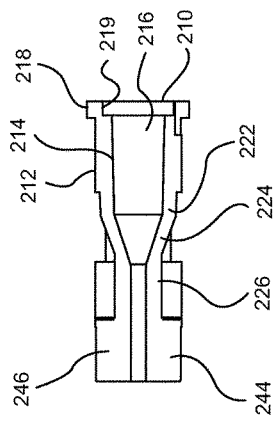
FIG. 11 illustrates a cross-sectional view of the female non-luer connector shown in FIG. 7 taken along line 11-11.
Figure 19:
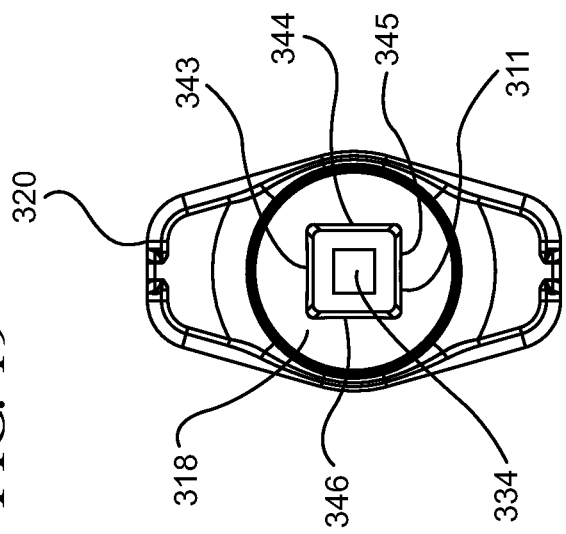
FIG. 19 illustrates a front elevational view of the container shown in FIG. 16.
Figure 18:
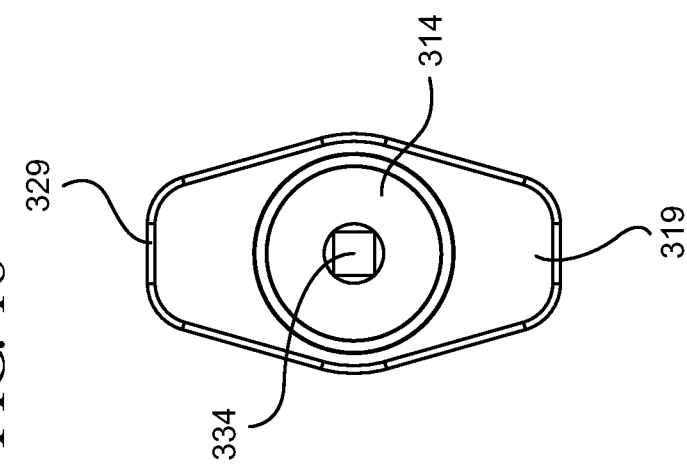
FIG. 18 illustrates a rear elevational view of the container shown in FIG. 16.
Figure 20:
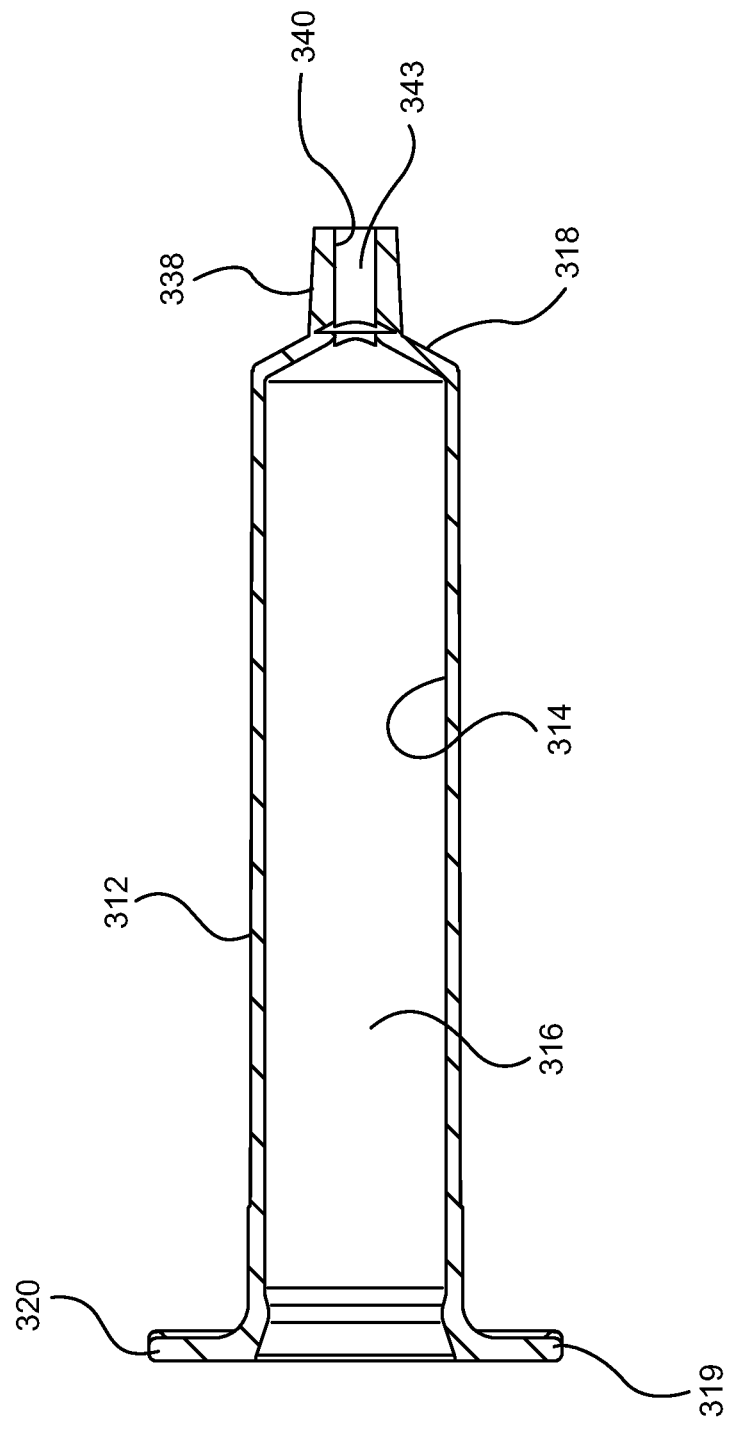
FIG. 20 illustrates a cross-sectional view of the container shown in FIG. 17 taken along line 20-20.
Figure 23:
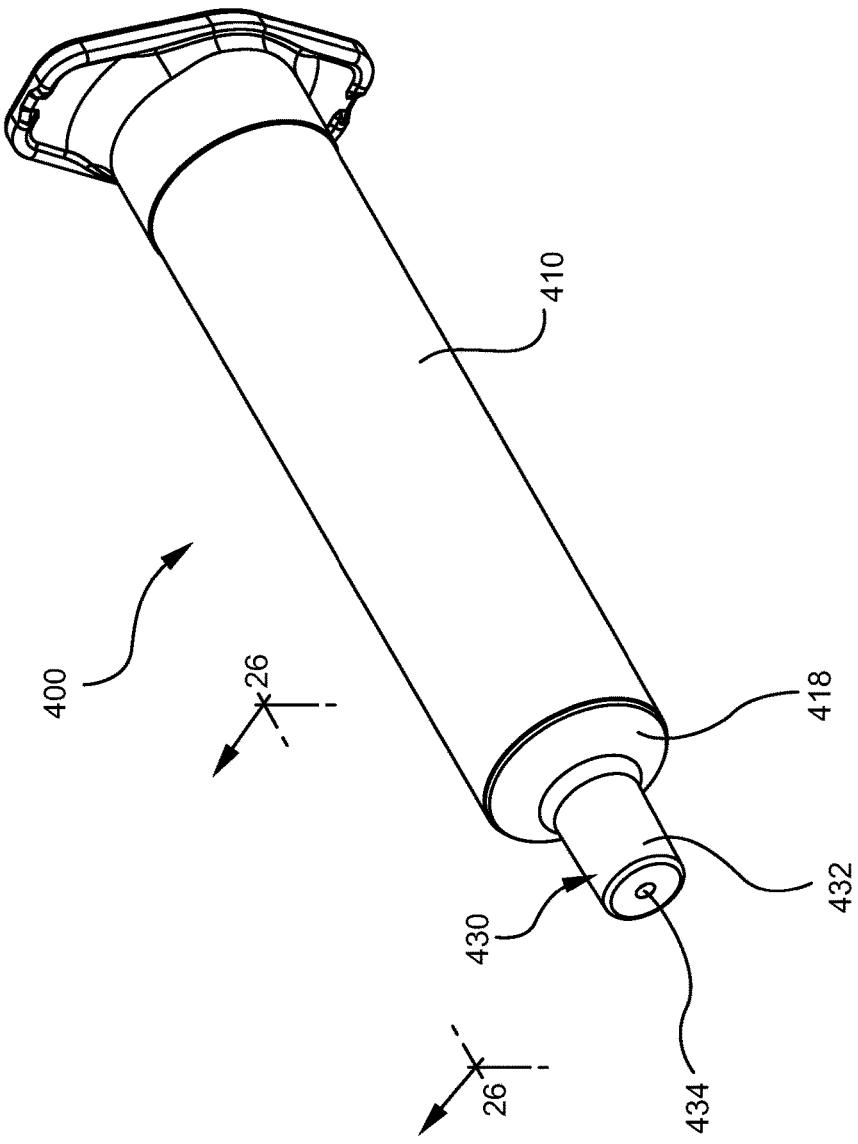
FIG. 23 illustrates a perspective view from a distal end of a container according to one or more embodiments of the present invention.
Figure 25:
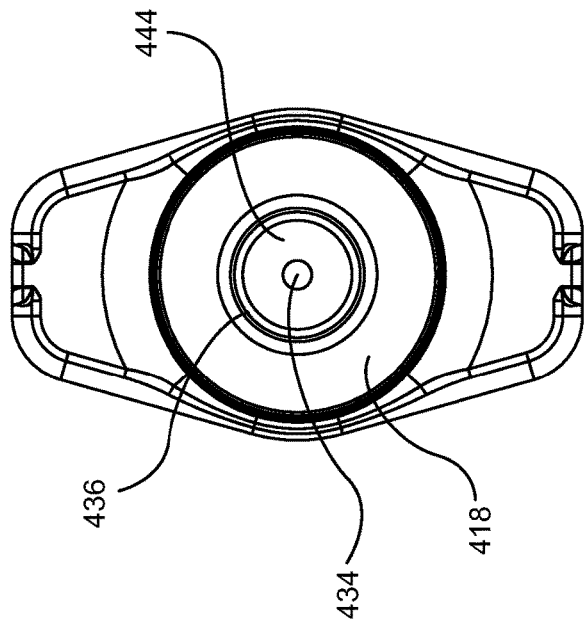
FIG. 25 illustrates a front elevational view of the container shown in FIG. 23.
Figure 24:
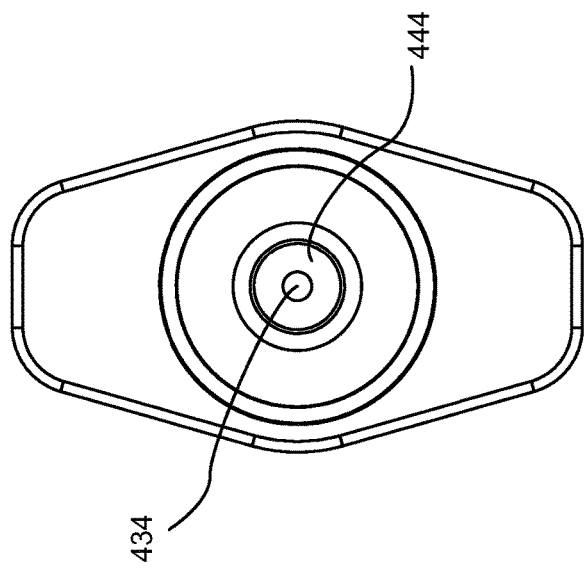
FIG. 24 illustrates a rear elevational view of the container shown in FIG. 23.
Figure 26:
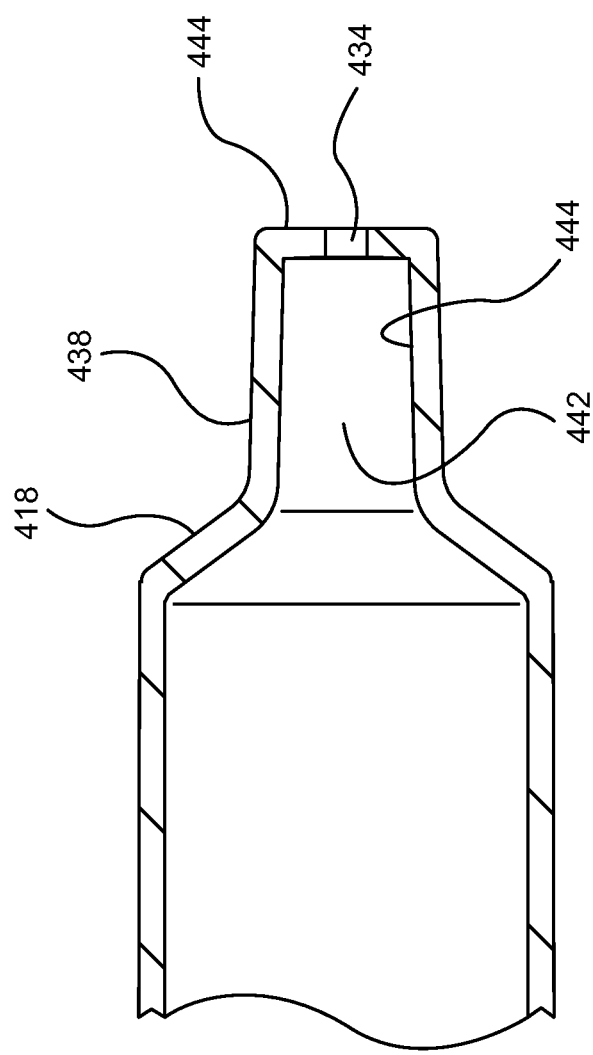
FIG. 26 illustrates an enlarged partial cross-sectional view of the container shown in FIG. 23 taken along line 26-26.
Figure 28:
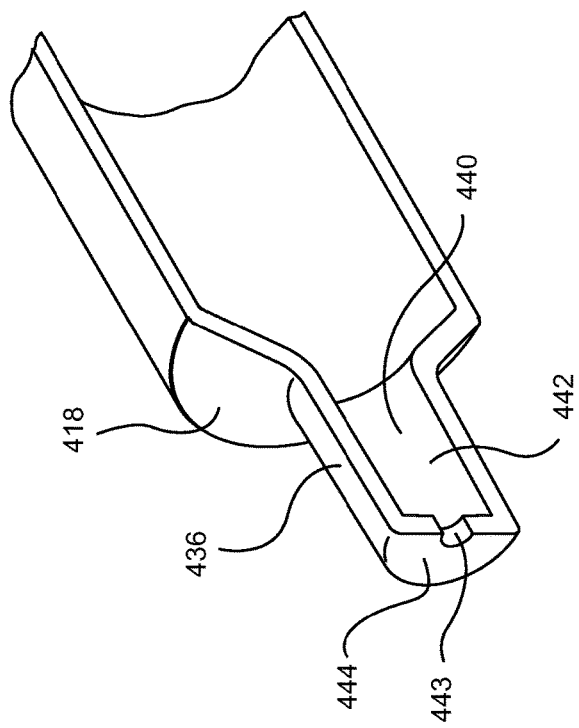
FIG. 28 shows a perspective view of the container shown in FIG. 26 taken from the distal end.
Figure 27:
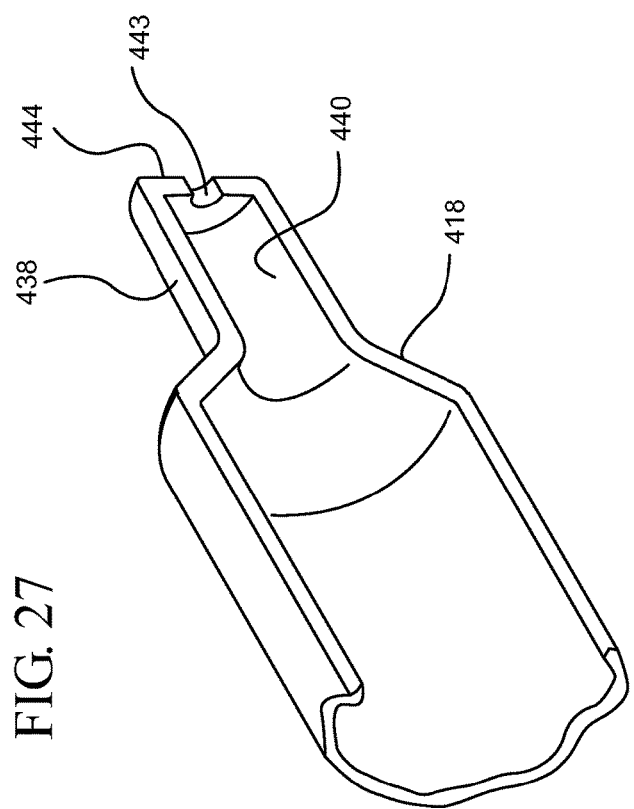
FIG. 27 illustrates a perspective view of the container shown in FIG. 26 taken from the proximal end.

The second narrowed wall 224 has an inner cross-sectional dimension that is less than the inner cross-sectional dimension of the first narrowed wall 222 and the inner cross-sectional dimension of the wall 212. As shown in FIG. 11, the second narrowed wall 224 may have a taper wherein its inner cross-sectional dimension decreases in the distal direction. In the embodiment shown in FIG. 11, the taper or decrease in the inner cross-sectional dimension of the second narrowed wall 224 is severe or drastic. In one or more alternative embodiments, the taper or decrease in the inner cross-sectional dimension of the second narrowed wall 224 may be gradual and/or the second narrowed portion may have a constant inner cross-sectional dimension. The third narrowed wall 226 has an inner cross-sectional dimension that is less than the inner cross-sectional dimensions of the wall 212, the first narrowed wall 222 and the second narrowed wall 224. The third narrowed wall 226 may have a constant inner cross-sectional dimension or, as shown in FIG. 11, include a proximal portion with a tapered inner cross-sectional dimension that decreases in the distal direction and a distal portion with a constant inner cross-sectional dimension. The third narrowed wall 226 is shaped and sized to support a needle cannula within the cavity 216, which extends from the open proximal end 209 of the female non-luer connector to the open distal end of the hub, including from the wall 212 to the third narrowed wall 226.

In one or more embodiments, the cavity 216 has an inner cross-sectional dimension measured at the proximal end 209 of less than 0.168 inches. In one or more specific embodiments, the cavity 216 has an inner cross-section dimension measured at the proximal end 209 in the range from about 0.100 inches to about 0.1600 inches, or more specifically in the range from about 0.1300 inches to about 0.1500 inches. In an even more specific embodiment, the cavity 216 has an inner cross-section dimension measured at the proximal end 209 in the range from about 0.1417 inches to about 0.1437 inches. The lower limit of the inner cross-sectional dimension of the cavity 216 at the proximal end 209 may include 0.1400 inches, 0.1404 inches, 0.1408 inches, 0.1412 inches and 0.1416 inches. The upper limit of the inner cross-sectional dimension of the cavity 216 at the proximal end 209 may include 0.1439 inches, 0.1443 inches, 0.1447 inches, 0.1451 inches and 0.1455 inches. In one or more embodiments, the inner cross-sectional dimension of the cavity 216 may be in the range from about 0.100 inches to 0.119 inches, from about 0.130 inches to about 0.139 inches, from about 0.140 inches to about 0.149 inches, from about 0.150 inches to about 0.159 inches, or from about 0.159 inches to about 0.167 inches.

In one or more embodiments, the inside surface 214 of the wall 212 may have a taper of less than 6% decreasing in a proximal to distal direction or an inner cross-section dimension that decreases from the proximal end 209 toward the distal end 201 at a rate of less than 6%. In one or more specific embodiments, the inside surface 214 of the wall 212 has a taper decreasing in a proximal to distal direction in the range from about 3% to about 5.9%. In one or more embodiments, the taper of the inside surface 214 of the wall 212 may be in the range from about 0.5% to about 2.9% decreasing in a proximal to distal direction. In a specific embodiment, the taper of the inside surface 214 of the wall 212 is about 5% decreasing in a proximal to distal direction. The lower limit of the taper of the inside surface 214 of the wall 212 decreasing in a proximal to distal direction may include 4.2%, 4.4%, 4.6%, 4.8%. The upper limit of the taper of the inside surface 214 of the wall 212 decreasing in a proximal to distal direction may include 5.2%, 5.4%, 5.6%, 5.8%. In one or more embodiments, the inside surface 214 of the wall 212 may have a taper of more than 6% decreasing in a proximal to distal direction or an inner cross-section dimension that decreases from the proximal end 209 toward the distal end 201 at a rate of more than 6%.

In one or more embodiments, the length of the cavity 216 measured from the proximal end 209 to the end of the second narrowed wall 224, but not including the second narrowed wall, may be in the range from about 0.200 inches to about 0.500 inches. In a more specific embodiment, the length of the cavity 216 from the proximal end 209 to the end of the second narrowed wall 224, but not including the second narrowed wall 224, may be in the range from about 0.295 inches to about 0.400 inches. In an even more specific embodiment, the length of the cavity 216 may be about 0.303 inches.

The outside surface 203 of the female non-luer connector includes at least one arm that extends from the first narrowed wall 222 to a location adjacent to the open distal end 201 of the hub. In the embodiment shown in FIGS. 5-13, the female non-luer connector 200 includes two arms 231, 232 that are disposed on opposite sides of the female non-luer connector 200 and extend from the first narrowed wall 222 to a location adjacent to the open distal end 201. The arms 231, 232 define spaces 234, 236 between the outside surface 203 of the female non-luer connector and the arms 231, 232. The arms 231, 232 provide a finger grip area or a gripping surface on which to grasp the female non-luer connector 200 during use. The arms 231, 232 may have any shape known to provide such a finger grip area. In one or more alternative embodiments, the female non-luer connector 200 may be free of any structure on its outside surface 203.

Figure 12:
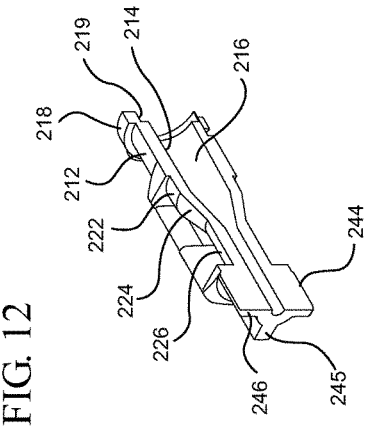
FIG. 12 illustrates a perspective view of the female non-luer connector shown in FIG. 11 taken from the proximal end.
Figure 13:
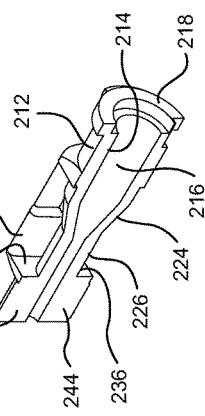
FIG. 13 shows a perspective view of the female non-luer connector shown in FIG. 11 taken from the distal end.

Adjacent to the open distal end 201, the female non-luer connector includes an annular disc 240 disposed adjacent to the two arms 231, 232 that extends radially outwardly from the outside surface 203 of the hub. Four discrete protrusions 243, 244, 245, 246 extend radially outwardly from the outside surface 203 and extend from the annular disc 240 to the open distal end 201 along the same axis. The four discrete protrusions 243, 244, 245, 246 are located along the third narrowed wall 222, as shown in FIGS. 11 and 12.

Figure 6:
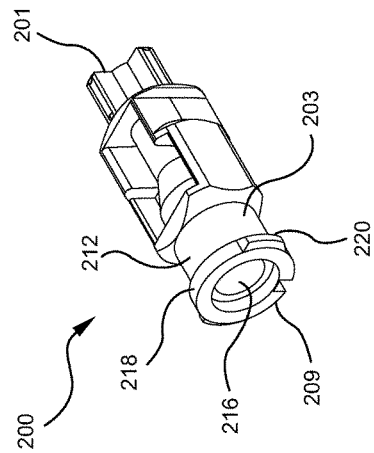
FIG. 6 illustrates a perspective view from a proximal end of the non-luer hub shown in FIG. 5.
Figure 5:
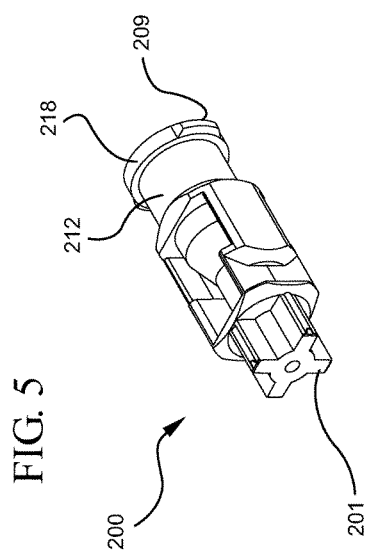
FIG. 5 illustrates a perspective view of a female non-luer connector according to one or more embodiments of the present invention.
Figure 8:
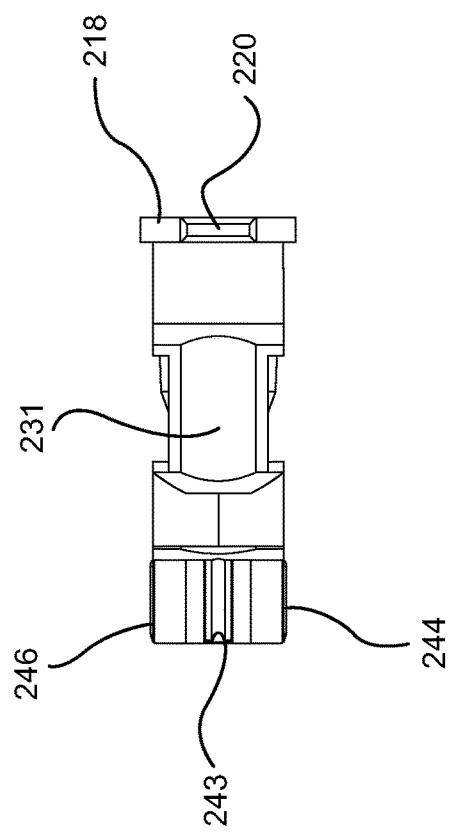
FIG. 8 illustrates a side elevational view of the female non-luer connector shown in FIG. 7, after rotating the connector 90 degrees.
Figure 7:
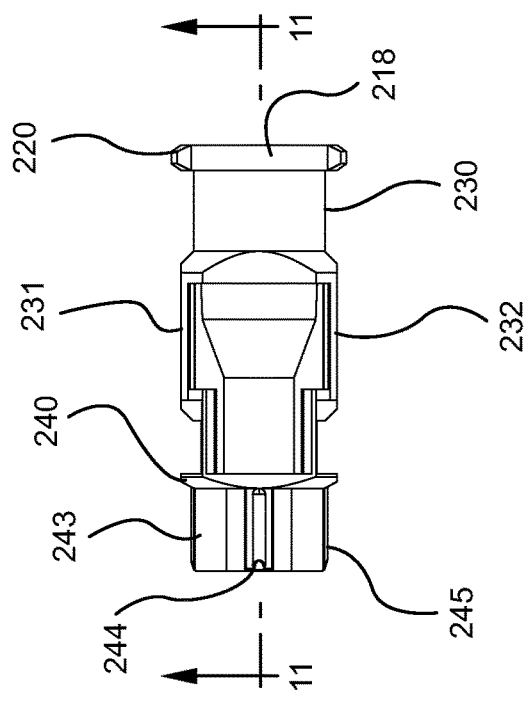
FIG. 7 illustrates a side elevational view of the female non-luer connector shown in FIG. 5.
Figure 10:
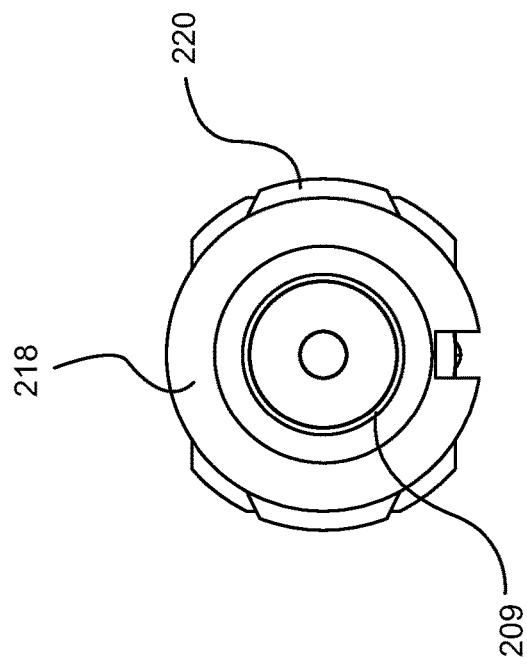
FIG. 10 illustrates a rear elevational view of the female non-luer connector shown in FIG. 7.
Figure 9:
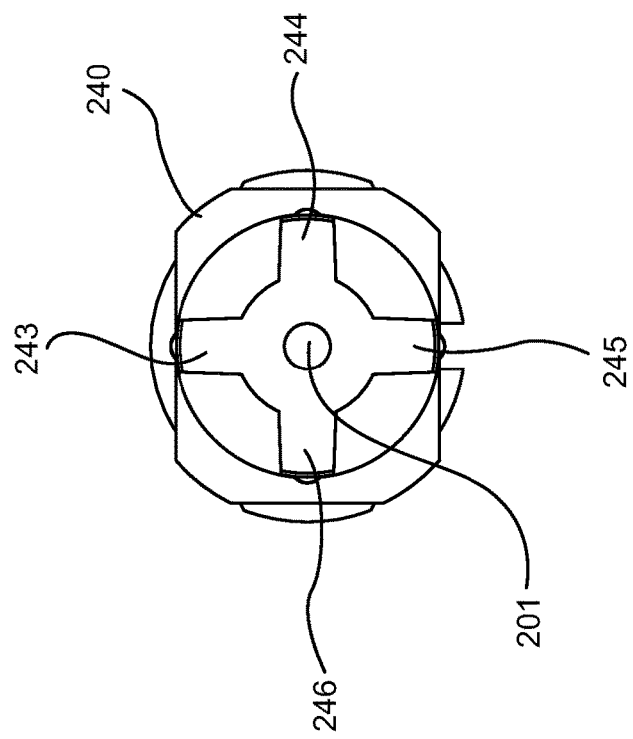
FIG. 9 illustrates a front elevational view of the female non-luer connector shown in FIG. 7.

As shown more clearly in FIG. 6, the rim 218 may include an indentation for use with a stylet and a spinal needle. In one or more alternative embodiments, the indentation provides a needle bevel orientation indicator in which the indentation is aligned with the bevel of a needle cannula.

One or more embodiments of a non-luer connector for use in a drug delivery device according to the first aspect of the present invention are shown in FIGS. 14-22. FIGS. 14-22 illustrate a non-luer connector 300 that includes a non-luer portion 330 for attachment to another non-luer connector, for example, the female non-luer connector 200 described above. The non-luer connector 300 of FIGS. 14-22 is shown integrally formed to a container in the form of a syringe barrel 310. The container may be provided in other forms, for example, a drug bag, an epidural pump and other containers known in the art. The syringe barrel 310 shown in FIGS. 14-22 includes a distal end 311, an open proximal end 319 and a sidewall 312 extending between the distal end 311 to the open proximal end 319. The sidewall 312 includes an inside surface 314 that defines a chamber 316 for retaining fluids, which may include liquid medication and/or other liquids. The open proximal end 319 may include an option flange 320 and the distal end 311 includes a distal wall 318. The non-luer portion 330 is integrally formed or provided in the container. Specifically, in the embodiment shown in FIGS. 14-22, the non-luer portion 330 is provided in the form of a tip 332 that extends in the distal direction from the distal wall 318 and includes an opening 334. The tip 332 extends from the distal wall 318 to a distal end 333 of the tip. The tip 332 includes an outside surface 338 and an inside surface 340 that defines a passageway 342 permitting fluid communication between the chamber 316 and the opening 334.

In the embodiment shown, the tip 332 has a dimension and/or shape that prevent the connection of a standard female luer connector, for example, the needle hub 130 shown in FIG. 4, to the syringe barrel 310. Specifically, the non-luer portion 330 has a square cross-section and/or an outer cross-sectional dimension that is not compatible with typical luer connectors which have a circular cross-section and/or smaller or larger outer cross-sectional dimension. In the embodiment shown, the tip 332 is shown in the form of four discrete walls 343, 344, 345, 346 that are connected to form an enclosure around the passageway 342 of the tip 332 having a square cross-section. In one or more embodiments, the outer cross-sectional dimension of the tip 332, measured from the outside surface 338 of the tip 332 at the intersection of walls 343 and 346 and the intersection of walls 345 and 344 is greater than the inner cross-sectional dimension of the inside surface 134 of the hub body 132 of luer connector 133 of the needle hub 130. Accordingly, the hub body 132 cannot fit or slide over the tip 332 such that the tip 332 is disposed within the cavity 136 and the inside surface 134 of the hub body 132 cannot form an interference fit connection and/or fluid-tight engagement with the outside surface 338 of the tip 332. Accordingly, the non-luer portion 330 prevents connection of a standard female luer connector, for example, the luer connector 133 of needle hub 130. As will be described below, the non-luer portion 330 has a dimension and/or shape that permit connection to another corresponding non-luer connector.

In one or more alternative embodiments, the tip 332 may have an outer cross-sectional dimension that is smaller than the inner cross-sectional dimension of a standard female luer connector. In such embodiments, the smaller outer cross-sectional dimension of the tip 332 prevents sufficient contact between the inside surface 134 of the luer connector and the outside surface 338 of the tip to form an interference fit connection and/or fluid-tight engagement there between.

In one or more embodiments, even if the inside surface 134 of the hub body 132 had a inner cross-sectional dimension large enough to permit the hub body 132 to slide over the outside surface 338 of the tip 332 such that the tip 332 is disposed within the cavity 136, the square cross-section of the tip 332 prevents the inside surface 134 of the hub body 132 from having sufficient contact with the outside surface 338 of the tip 332 to form an interference fit connection and/or a fluid-tight seal with the outside surface 338 of the tip 332. This is because the inside surface 134 is curved and would not contact the outside surface 338 of the tip 332. In other words, the corners of the tip 332 having a square cross-section would not be in contact with the inside surface of a hub with a circular cross-section, for example needle hub 130. In one or more alternative embodiments, the tip 332 may have a triangular cross-section, or other cross-section that prevents sufficient contact with the inside surface of a standard female luer connector, for example the inside surface 134 of luer connector 133, thereby preventing the formation of an interference fit connection and/or fluid-tight seal there between.

The tip 332 may also have a length that prevents formation of an interference fit connection and/or fluid-tight engagement with a standard female luer connector. Specifically, the length of the tip 332 may be too long or too short to permit the respective taper of the tip 332 and the inside surface 134 of the luer connector to align to form an interference fit connection and/or fluid-tight engagement there between.

In one or more embodiments, the tip 332 has an outer cross-sectional dimension of 0.1545 inches or less at the distal end 333. In a more specific embodiment, the tip 332 has an outer cross-sectional dimension in the range from about 0.1200 inches to about 0.1500 inches at the distal end 333, or more specifically, in the range from about 0.1300 inches to about 0.1400 inches. In an even more specific embodiment, the tip 332 may have an outer cross-sectional dimension at the distal end 333 in the range from about 0.1306 inches to about 0.1326 inches. In one or more specific embodiments, the outer cross-sectional dimension of the tip 332 at the distal end 333 is in the range from about 0.100 inches to about 0.119 inches, from about 0.120 inches to about 0.129 inches, from about 0.130 inches to about 0.139 inches, from about 0.140 inches to about 0.149 inches, or from about 0.150 inches to about 0.154 inches. The upper limit of the outer cross-sectional dimension of the tip 332 at the distal end 333 may include 0.1328 inches, 0.1330 inches, 0.1332 inches, 0.13334 inches, 0.1336 inches and 0.1338 inches. The lower limit of the outer cross-sectional dimension of the tip 332 at the distal end 333 may include 0.1304 inches, 0.1302 inches, 0.1298 inches, 0.1296 inches, 0.1294 inches, 0.1292 inches and 0.1290 inches.

In one or more embodiments, the outside surface 338 of the tip 332 may have a taper of less than 6% decreasing in a proximal to distal direction or an outer cross-sectional dimension that decreases in a proximal to distal direction at a rate of less than 6%. In one or more specific embodiments, the outside surface 338 of the tip 332 may have a taper decreasing in a proximal to distal direction in the range from about 3% to about 5.9% or from about 0.5% to about 2.9%. In a specific embodiment, the outside surface 338 of the tip 332 has a 5% taper decreasing in the proximal to distal direction.

In one or more embodiments, the outside surface 338 of the tip 332 may have a taper of more than 6% decreasing in a proximal to distal direction or an outer cross-sectional dimension that decreases in a proximal to distal direction at a rate of more than 6%.

In one or more embodiments, the length of the tip 332 from the distal wall 318 to the distal end 333 of the tip may be in the range from about 0.200 inches to about 0.500 inches. In one or more specific embodiments, the length of the tip 332 may be in the range from about 0.250 inches to about 0.450 inches, or more specifically, in the range from about 0.295 inches to about 0.400 inches. In an even more specific embodiment, the length of the tip 332 may be about 0.300 inches.

In use with a corresponding non-luer connector, for example, the female non-luer connector 200 of FIGS. 5-13, the tip 332 is inserted into the cavity 216 of the female non-luer connector 200. A force is applied to the syringe barrel 310 in the distal direction and/or to the female non-luer connector 200 in the proximal direction to cause the inside surface 214 of the wall 212 of the female non-luer connector to engage the outside surface 338 of the tip 332 in an interference fit connection and/or fluid-tight engagement. To remove the female non-luer connector 200 from the syringe barrel 310, a force is applied to the container in the proximal direction and/or to the female non-luer connector 200 in the distal direction to disengage the interference fit connection and/or the fluid-tight engagement of there between.

FIGS. 23-28 illustrate another embodiment of a non-luer connector 400 for use in a drug delivery device according to the first aspect of the present invention. Specifically, FIGS. 23-28 illustrate a non-luer connector 400 that includes a non-luer portion 430 for attachment to a non-luer connector, for example, the female non-luer connector 200 described above. The non-luer connector 400 is shown integrally formed to a container in the form of a syringe barrel 410, as described above with reference to FIGS. 14-22. As mentioned above with respect to FIGS. 14-22, the container may be provided in other forms, for example, a drug bag, an epidural pump and other containers known in the art. The syringe barrel 410 shown in FIGS. 23-28 includes a distal wall 418. The non-luer portion 430 is integrally formed or provided in the container. Specifically, in the embodiment shown in FIGS. 23-28, the non-luer portion 430 is provided in the form of a tip 432 that extends in the distal direction from a distal wall 418 of the syringe barrel 410 and includes an opening 434. The tip 432 includes a body wall 436 that extends from the distal wall 418 to a distal end 433 of the tip. The body wall 436 that includes an outside surface 438 and an inside surface 440 that define a passageway 442 permitting fluid communication between the chamber of the syringe barrel 410 and the opening 434. The distal end 433 of the tip 432 also includes an end wall 444 that extends inwardly from the outside surface 438 of the body wall 436 to the opening 434.

In the embodiment shown, the body wall 436 has a dimension and/or shape that prevent the connection of a standard female luer connector, for example, the needle hub 130 shown in FIG. 4, to the syringe barrel 410. Specifically, the body wall 436 of the non-luer portion 430 has an outer cross-sectional dimension and/or a thickness that is not compatible with typical luer connectors, which have smaller or larger inner cross-sectional dimension. In the embodiment shown, the body wall 436 is shown in the form of a continuous wall having a circular cross-section that forms an enclosure around the passageway 442 of the tip 432 having a square cross-section. In one or more embodiments, the outer cross-sectional dimension of the body wall 436 at the outside surface 438 is greater than the inner cross-sectional dimension of the inside surface 134 of the hub body 132 of luer connector 133 of the needle hub. Accordingly, the hub body 132 cannot fit or slide over the body wall 436 such that the tip 432 is disposed within the cavity 136 and the inside surface 134 of the hub body 132 cannot form an interference fit connection and/or fluid-tight engagement with the outside surface 438 of the body wall 436. Accordingly, the non-luer portion 430 prevents connection of a standard female luer connector, for example, needle hub 130. As will be described below, the non-luer portion 430 has an outer cross-sectional dimension that permits connection to another corresponding non-luer connector.

The thickness of the body wall 436 may also have a dimension that prevents connection of a standard female luer connector to the non-luer connector 430. Specifically, the body wall 436 may have a thickness that increases the outer cross-sectional dimension of the tip 432, which, as discussed above, prevents formation of an interference fit connection and/or fluid-tight engagement of with a standard female luer connector. The thickness of the body wall 436 may also be modified by decreasing the cross-sectional dimension of the passageway 442 and maintaining the outer cross-sectional dimension of the tip 432.

In one or more alternative embodiments, the tip 432 may have an outer cross-sectional dimension that is smaller than the inner cross-sectional dimension of a standard female luer connector, for example, the luer connector 133 of needle hub 130, shown in FIG. 4. In such embodiments, the smaller outer cross-sectional dimension of the body wall 436 prevents sufficient contact between the inside surface 134 of the luer connector and the outside surface 438 of the body wall to form a interference fit connection and/or fluid-tight engagement there between. The non-luer portion 430 or the tip 432 may also have a length that prevents formation of an interference fit connection and/or fluid-tight engagement with a standard female luer connector, for example the luer connector 133 of FIG. 4. Specifically, the length of the body wall 436 may be too long or too short to permit the respective taper of the body wall 436 and the inside surface 134 of the luer connector to align to form an interference fit connection and/or fluid-tight engagement there between.

In one or more embodiments, the tip 432 has an outer cross-sectional dimension of less than 0.1545 inches at the distal end 433 of the tip or at the end wall 444. It will be understood that the outer cross-sectional dimension of the tip 432 includes the longest distance between two points on the outer surface 438 of the tip. In a more specific embodiment, the tip 432 has an outer cross-sectional dimension in the range from about 0.1200 inches to about 0.1500 inches, or more specifically, in the range from about 0.1300 inches to about 0.1400 inches at the distal end 433 of the tip or at the end wall 444. In an even more specific embodiment, the tip 432 may have an outer cross-sectional dimension in the range from about 0.1306 inches to about 0.1326 inches at the end wall 444 or at the distal end of the tip. In one or more specific embodiments, the outer cross-sectional dimension of the tip 432 at the end wall 444 or at the distal end 433 of the tip is in the range from about 0.100 inches to about 0.119 inches, from about 0.120 inches to about 0.129 inches, from about 0.130 inches to about 0.139 inches, from about 0.140 inches to about 0.149 inches, or from about 0.150 inches to about 0.154 inches. The upper limit of the outer cross-sectional dimension of the tip 432 at the end wall 444 or distal end 433 of the tip may include 0.1328 inches, 0.1326 inches, 0.1330 inches, 0.1332 inches, 0.13334 inches, 0.1336 inches and 0.1338 inches. The lower limit of the outer cross-sectional dimension of the tip 432 at the end wall 444 or at the distal end 433 of the tip may include 0.1306 inches, 0.1304 inches, 0.1302 inches, 0.1298 inches, 0.1296 inches, 0.1294 inches, 0.1292 inches and 0.1290 inches.

In one or more embodiments, the outside surface 438 of the tip 432 may have a taper of less than 6% decreasing in a proximal to distal direction or an outer cross-section dimension that decreases in a proximal to distal direction at a rate of less than 6%. In one or more specific embodiments, the outside surface 438 of the tip 432 may have a taper decreasing in a proximal to distal direction in the range from about 3% to about 5.9% or from about 0.5% to about 2.9%. In a specific embodiment the outside surface 438 of the tip 432 may have a taper of 5% decreasing in the proximal to distal direction.

In one or more embodiments, the length of the tip 432 from the distal wall 418 to the distal end 433 of the tip or at the end wall 444 may be in the range from about 0.200 inches to about 0.500 inches. In one or more specific embodiments, the length of the tip 432 from the distal wall 418 to the distal end 433 of the tip or at the end wall 444 may be in the range from about 0.250 inches to about 0.450 inches, or more specifically, in the range from about 0.295 inches to about 0.400 inches. In an even more specific embodiment, the length of the tip 432 from the distal wall 418 to the distal end 433 of the tip or at the end wall 444 may be about 0.300 inches.

In use with a corresponding non-luer connector, for example, the female non-luer connector 200 of FIGS. 5-13, the tip 432 is inserted into the cavity 216 of the female non-luer connector 200. A force is applied to the syringe barrel 410 in the distal direction and/or to the female non-luer connector 200 in the proximal direction to cause the inside surface 214 of the wall 212 of the female non-luer connector to engage the outside surface 438 of the tip 432 in an interference fit connection and/or fluid-tight engagement. To remove the female non-luer connector 200 from the syringe barrel 410, a force is applied to the container in the proximal direction and/or to the female non-luer connector 200 in the distal direction to disengage the interference fit connection and/or the fluid-tight engagement of there between.

One or more embodiments of a non-luer connector 500 for use in a drug delivery device according to the second aspect of the present invention are shown in FIGS. 29-34. FIGS. 29-34 illustrate a non-luer connector 500 that includes a non-luer element 550 that prevents attachment of a standard female luer connector, for example, needle hub 130 described above, thereto. The non-luer connector 500 of FIGS. 29-34 is shown integrally formed to a container in the form of a syringe barrel 510, as described above with reference to FIGS. 14-22. The container may be provided in other forms, for example, a drug bag, epidural pump and other containers known in the art. The syringe barrel 510 shown in FIGS. 29-34 includes a distal wall 518. A tip 532 extends in the distal direction from a distal wall 518 of the syringe barrel 510 and includes a passageway 542 and an opening 534 in fluid communication with the chamber of the syringe barrel.

The outside surface 538 of the tip may have a dimension and/or shape that forms an interference fit connection and/or fluid-tight engagement with the inside surface of a corresponding non-luer connector. In one or more embodiments, the outside surface 538 of the tip has a dimension and/or shape that may permit a user to force an incorrect interference fit connection and/or an incorrect fluid-tight engagement of the non-luer connector 500 with a standard female luer connector. As will be described below, the non-luer element prevents such incorrect connection or engagement. In one or more embodiments, the outside surface 538 of the tip has a dimension and/or shape that prevents formation of an interference fit connection and/or fluid-tight engagement with a standard female luer connector and, instead, permits such connection and/or engagement with a corresponding non-luer connector.

In one or more embodiments, the tip 532 has an outer cross-sectional dimension of less than 0.1545 inches, measured at a distal end 536 of the tip. In a more specific embodiment, the tip has an outer cross-sectional dimension measured at the distal end 536 in the range from about 0.1200 inches to about 0.1500 inches, or more specifically, in the range from about 0.1300 inches to about 0.1400 inches. In an even more specific embodiment, the tip may have an outer cross-sectional dimension measured at the distal end 536 in the range from about 0.1306 inches to about 0.1326 inches. In one or more specific embodiments, the outer cross-sectional dimension of the tip 532 measured at the distal end 536 is in the range from about 0.100 inches to about 0.119 inches, from about 0.120 inches to about 0.129 inches, from about 0.130 inches to about 0.139 inches, from about 0.140 inches to about 0.149 inches, or from about 0.150 inches to about 0.154 inches. The upper limit of the outer cross-sectional dimension of the tip 532 measured at the distal end 536 may include 0.1328 inches, 0.1330 inches, 0.1332 inches, 0.13334 inches, 0.1336 inches, 0.1314 inches and 0.1338 inches. The lower limit of the outer cross-sectional dimension of the tip 532 measured at the distal end 536 may include 0.1304 inches, 0.1307 inches, 0.1302 inches, 0.1298 inches, 0.1296 inches, 0.1294 inches, 0.1292 inches and 0.1290 inches.

In one or more embodiments, the outside surface 538 of the tip 532 may have a taper of less than 6% decreasing in a proximal to distal direction or an outer cross-section dimension that decreases in a proximal to distal direction at a rate of less than 6%. In one or more specific embodiments, the outside surface 538 of the tip 532 may have a taper decreasing in a proximal to distal direction in the range from about 3% to about 5.9% or from about 0.5% to about 2.9%. In a specific embodiment, the outside surface 538 of the tip 532 has a 5% taper decreasing in a proximal to distal direction.

In one or more embodiments, the length of the tip 532 from the distal wall 518 to the distal end 536 of the tip may be in the range from about 0.200 inches to about 0.500 inches. In one or more specific embodiments, the length of the tip 532 from the distal wall 518 to the distal end 536 of the tip may be in the range from about 0.250 inches to about 0.450 inches, or more specifically, in the range from about 0.295 inches to about 0.400 inches. In an even more specific embodiment, the length of the tip 532 from the distal wall 518 to the distal end 536 of the tip may be about 0.300 inches.

The non-luer element 550 is integrally formed or provided in the container. Specifically, in the embodiment shown in FIGS. 29-34, the non-luer element 550 is integrally formed and disposed on the distal wall 518 of the syringe barrel and extends in the distal direction in a coaxial relationship with the tip 532. The non-luer element 550 forms a channel 560 between the tip 532 and the non-luer element 550. In the embodiment shown, the non-luer element 550 is shown as a plurality of barrier walls 552 that extend from the distal wall 518 in the distal direction. The barrier wall 552 includes a free or unattached distal end 558 and a proximal end 559. The barrier wall 552 may be described as cantilevered with respect to the distal wall 518.

The barrier wall 552 includes an inside surface 554 that faces the channel 560 and an outside surface 556. In the embodiment shown, the barrier wall 552 has a length that is equal to the length of the tip 532. In one or more alternative embodiments, the length of the barrier wall 552 may be less than or greater than the length of the tip 532. When the length of the barrier wall 552 is less than the length of the tip 532, it should not be so short that it fails to prevent the user from forcing an incorrect connection with a standard female luer connector. That is, the length of the barrier wall 552 is still sufficient to prevent such an incorrect connection. The length of the barrier wall 552 when it is longer than the tip 532 is not particularly limited except by practical considerations related to ease of manufacturing and ease of use. In one or more embodiments, the difference between the length of the barrier wall 552 and the length of the tip 532 is less than about 0.070 inches. In one or more specific embodiments, the difference between the length of the barrier wall 552 and the length of the tip 532 is in the range from about 0.00 inches to about 0.050 inches or from about 0.051 inches to about 0.070 inches.

The inside surface 554 of the barrier wall 552 may have a plurality of threads disposed thereon for engaging a corresponding structure of a non-luer connector. For example, when female non-luer connector 200 is attached to the non-luer connector 500, the tab 220 disposed on the outside surface 203 of the female non-luer connector engages the plurality of threads disposed on the inside surface 554 of the barrier wall 552. Engagement between the plurality of threads and the tab 220 is achieved by rotating the syringe barrel 510 and/or the non-luer connector 500 with respect to the female non-luer connector 200.

The barrier wall 552 of the embodiment shown in FIGS. 29-34 has a cross-section that has an outer cross-sectional dimension that is less than or equal to the inner cross-sectional dimension of a standard female luer connector, for example, the inner cross-sectional dimension of the hub body 132, of FIG. 4. The outer cross-sectional dimension of the barrier wall 552 may be sized to prevent the open proximal end of the luer connector, for example, the hub body 132 from entering the channel 560 and engaging the outside surface 538 of the tip 532. In one or more embodiments, the outer cross-sectional dimension of the barrier wall 552 may be less than the inner cross-sectional dimension of a standard luer connector and includes a feature that causes leakage between the standard luer connector and the barrier wall 552 when the standard luer connector is attached to the barrier wall 552. In one or more specific embodiments, the outer cross-sectional dimension of the barrier wall 552 may have a shape to prevent a standard female luer connector from entering the channel 560.

In one or more specific embodiments, the outer cross-sectional dimension of the barrier wall may larger than 0.170 inches. In one or more alternative embodiments, the thickness of the barrier wall 552 may be adjusted such that the inner cross-sectional dimension of the barrier wall 552 is less than 0.170 inches or is otherwise sized to prevent the standard female luer connector from entering the channel 560.

In embodiments in which the standard female luer connector incorporates lugs to engage a corresponding male luer lock connector, the outer cross-sectional dimension of the barrier wall 552 may be greater than about 0.307 inches. In embodiments, in which the female luer connector does not incorporate lugs, the outer cross-sectional dimension of the barrier wall 552 may be greater than about 0.224 inches.

In one or more embodiments, the outer cross-sectional dimension of the barrier wall 552 is in the range from about 0.175 inches to about 0.500 inches. In one or more specific embodiments, the outer cross-sectional dimension of the barrier wall 552 may be in the range from about 0.175 inches to about 0.264 inches, from about 0.265 inches to about 0.305 inches, from about 0.305 inches to about 0.500 inches. The upper limit of the outer cross-sectional dimension of the barrier wall 552 may include 0.300 inches, 0.302 inches, 0.304 inches, 0.306 inches, 0.308 inches, 0.310 inches and 0.312 inches. The lower limit of the outer cross-sectional dimension of the barrier wall may include 0.260 inches, 0.262 inches, 0.264 inches, 0.266 inches, 0.268 inches and 0.270 inches.

In one or more embodiments, the barrier wall 552 has an inner cross-sectional dimension in the range from about 0.200 inches to about 0.305 inches. In one or more specific embodiments, the inner cross-sectional dimension of the barrier wall 552 is in the range from about 0.200 inches to about 0.264 inches or from about 0.265 inches to about 0.305 inches. The lower limit of the inner cross-sectional dimension of the barrier wall 552 includes 0.260 inches, 0.262 inches, 0.264 inches, 0.266 inches, 0.268 inches and 0.270 inches. The upper limit of the outer cross-sectional dimension of the barrier wall 552 includes 0.300 inches, 0.302 inches, 0.304 inches, 0.306 inches, 0.308 inches, and 0.310 inches.

Figure 29A:
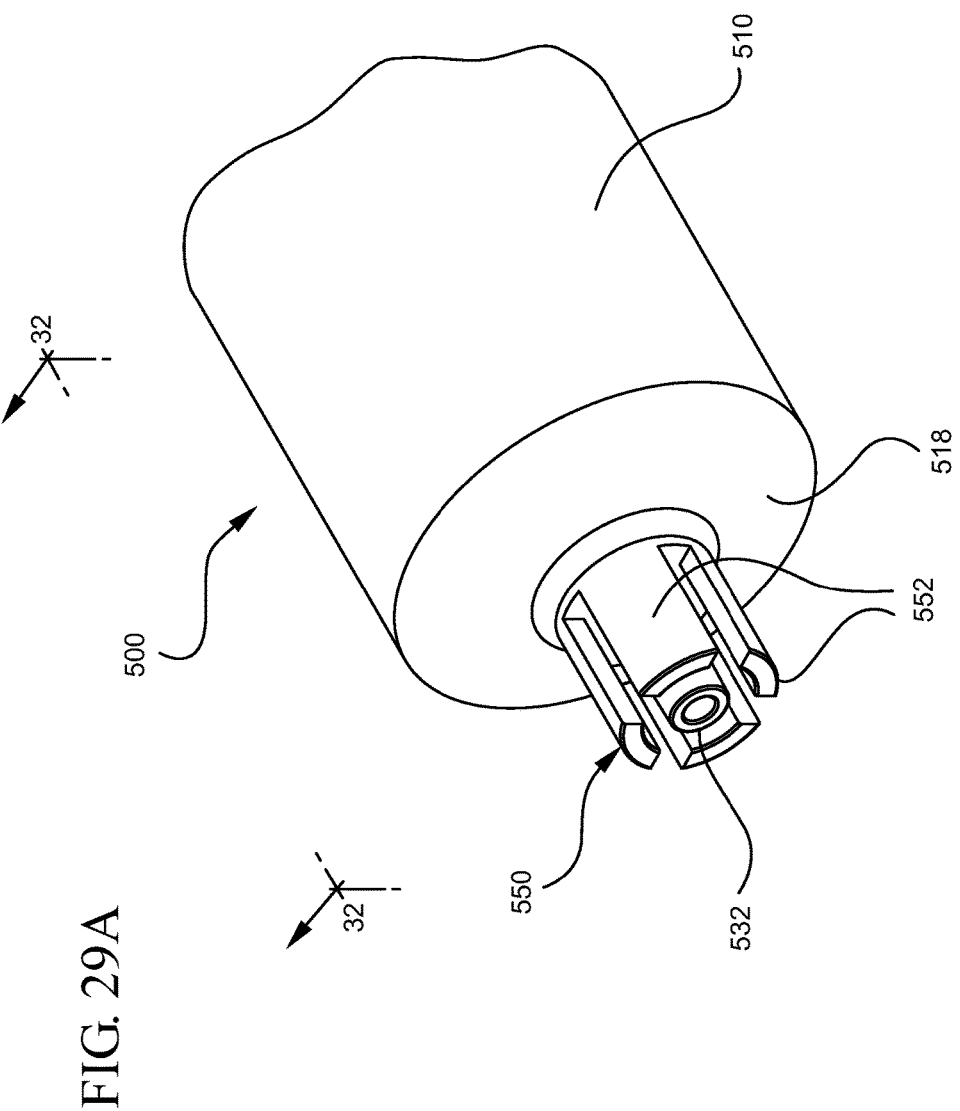
FIG. 29A illustrates a partial perspective view from a distal end of a container according to one or more embodiments of the present invention.
Figure 29B:
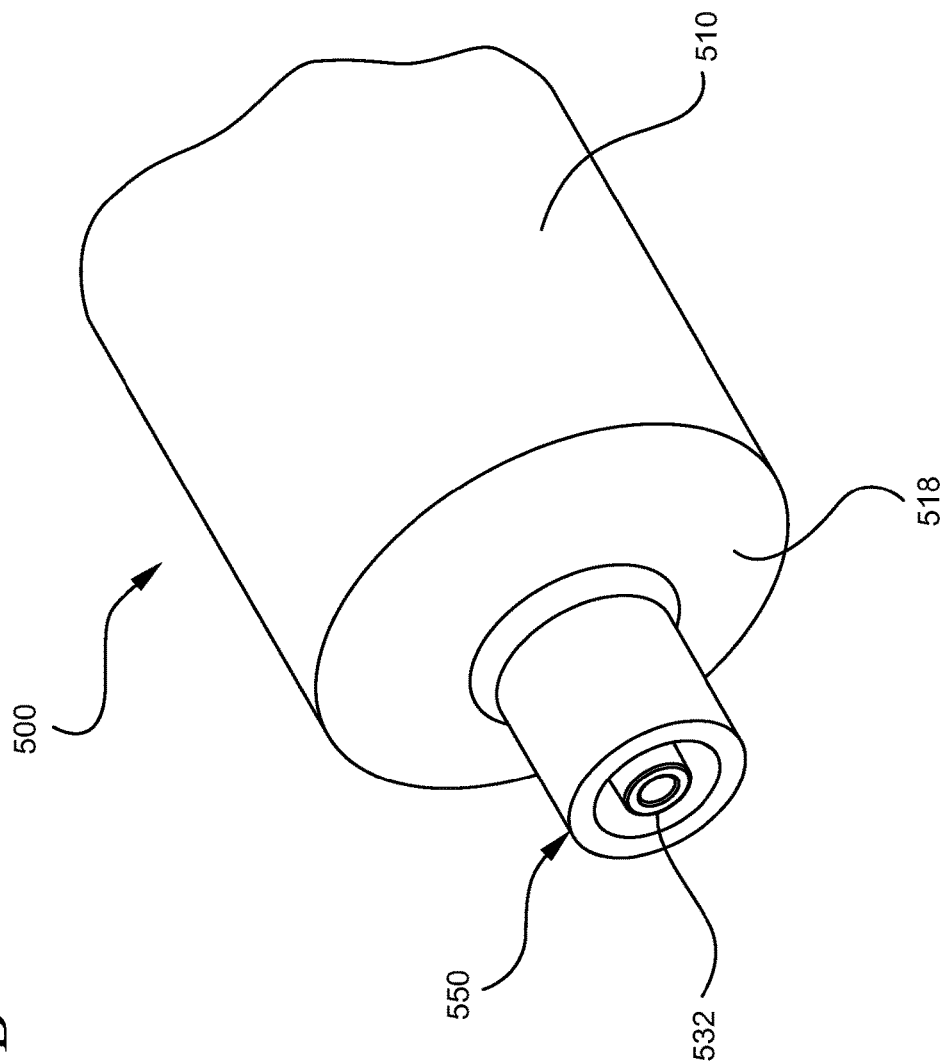
FIG. 29B illustrates a partial perspective view from a distal end of a container according to one or more embodiments of the present invention.
Figure 29C:
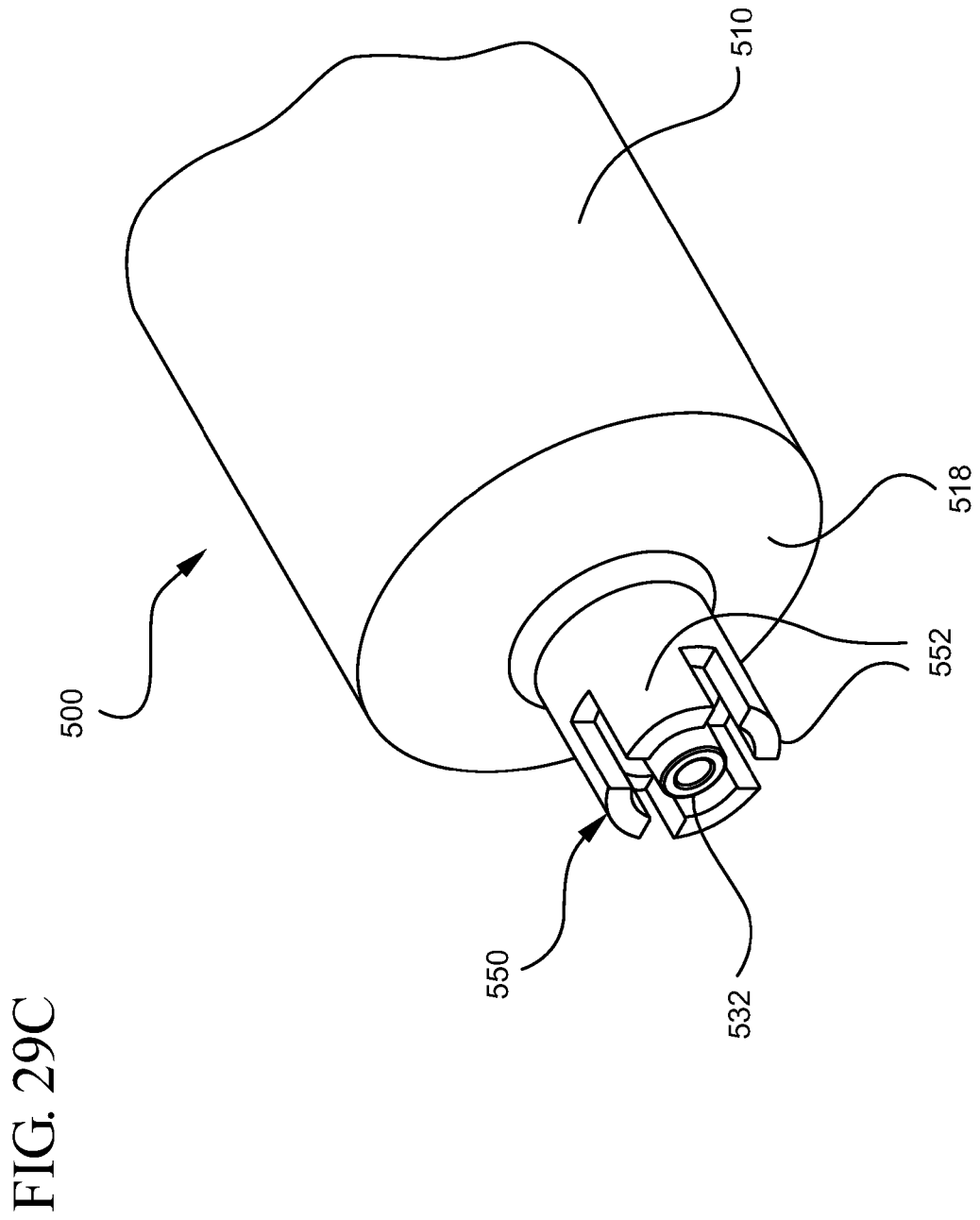
FIG. 29C illustrates a partial perspective view from a distal end of a container according to one or more embodiments of the present invention.
Figure 29D:
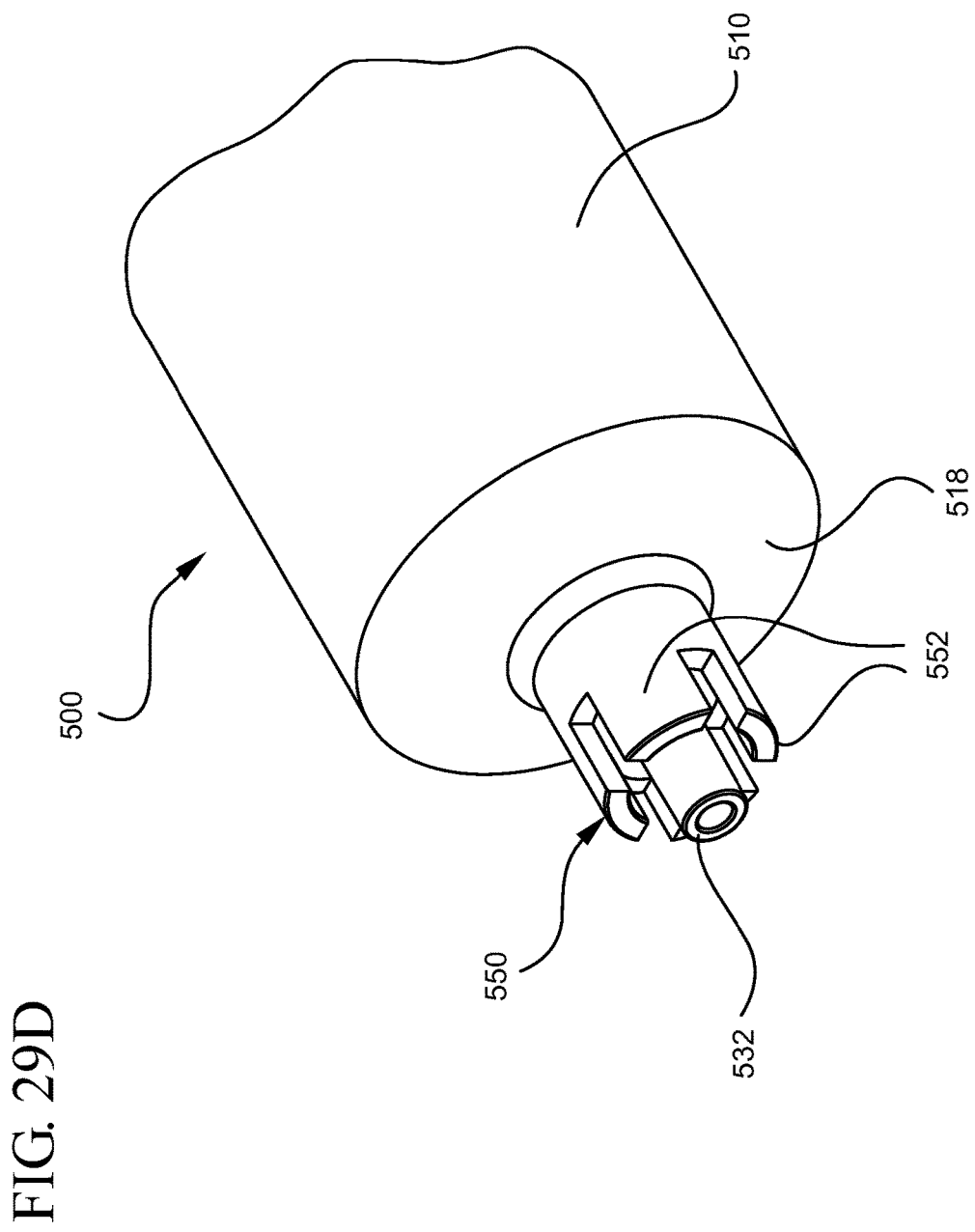
FIG. 29D illustrates a partial perspective view from a distal end of a container according to one or more embodiments of the present invention.
Figure 29E:
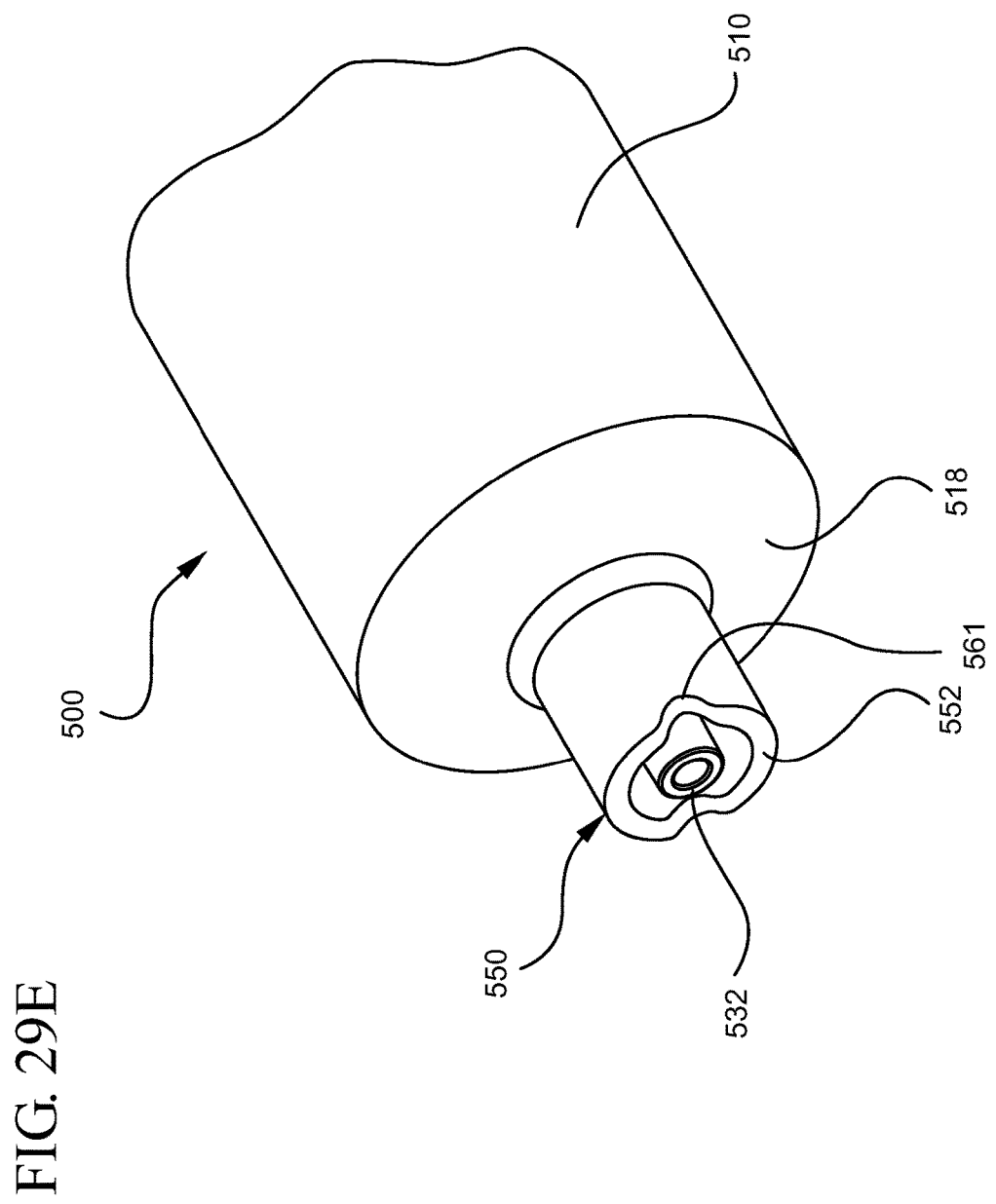
FIG. 29E illustrates a partial perspective view from a distal end of a container according to one or more embodiments of the present invention.
Figure 31:
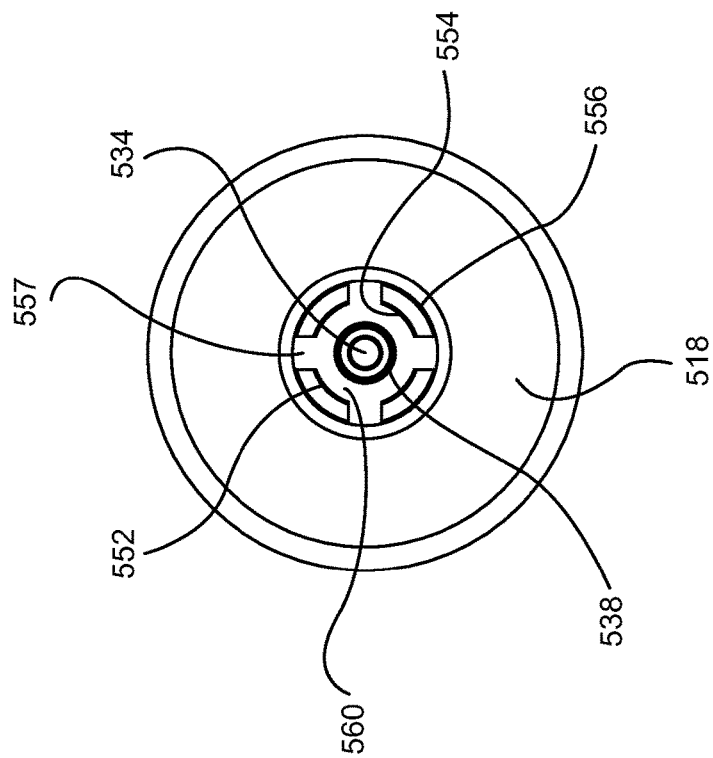
FIG. 31 illustrates a front elevational view of the container shown in FIG. 29.
Figure 30:
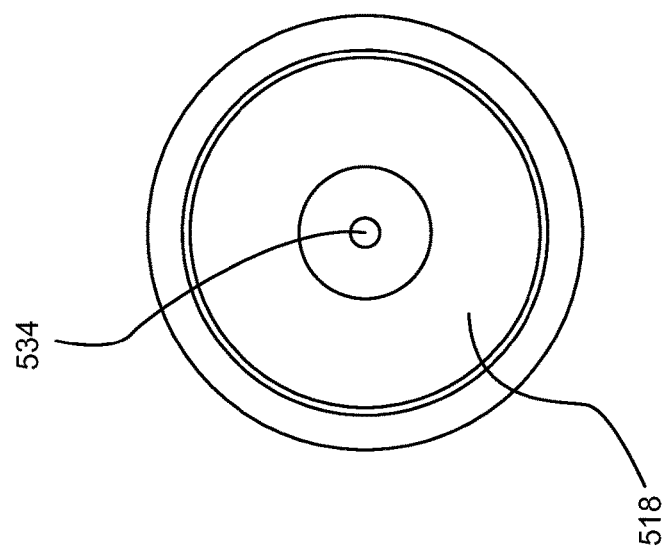
FIG. 30 illustrates a rear elevational view of the container shown in FIG. 29.
Figure 32:
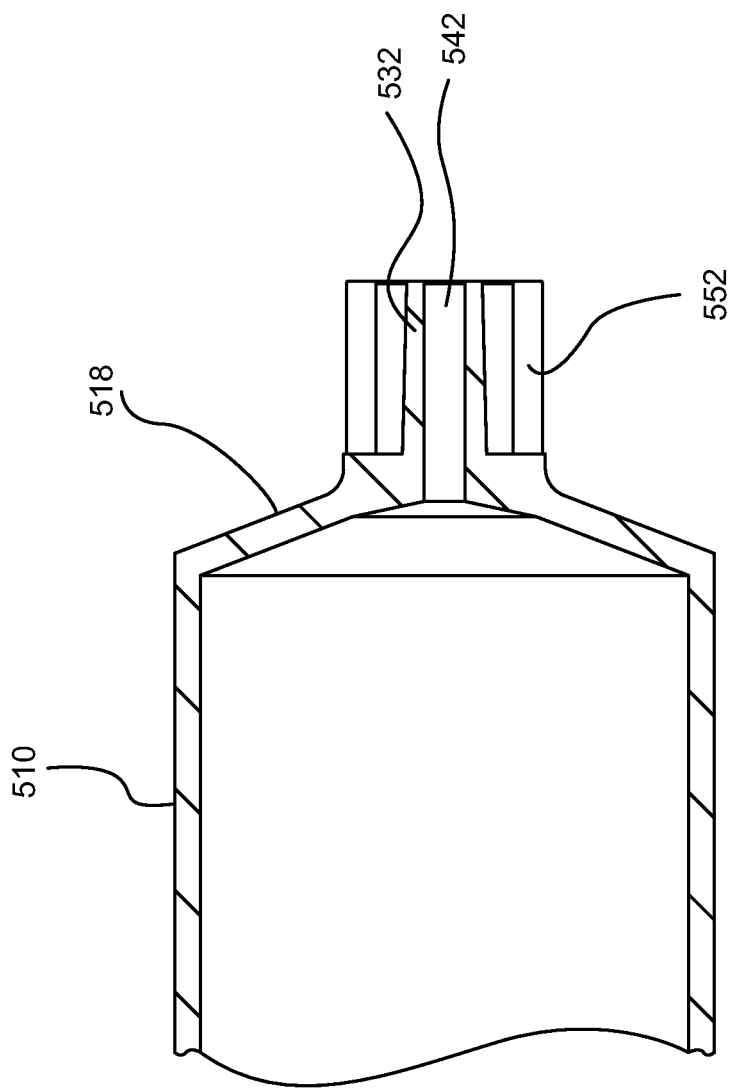
FIG. 32 illustrates an enlarged partial cross-sectional view of the container shown in FIG. 29 taken along line 32-32.
Figure 35:
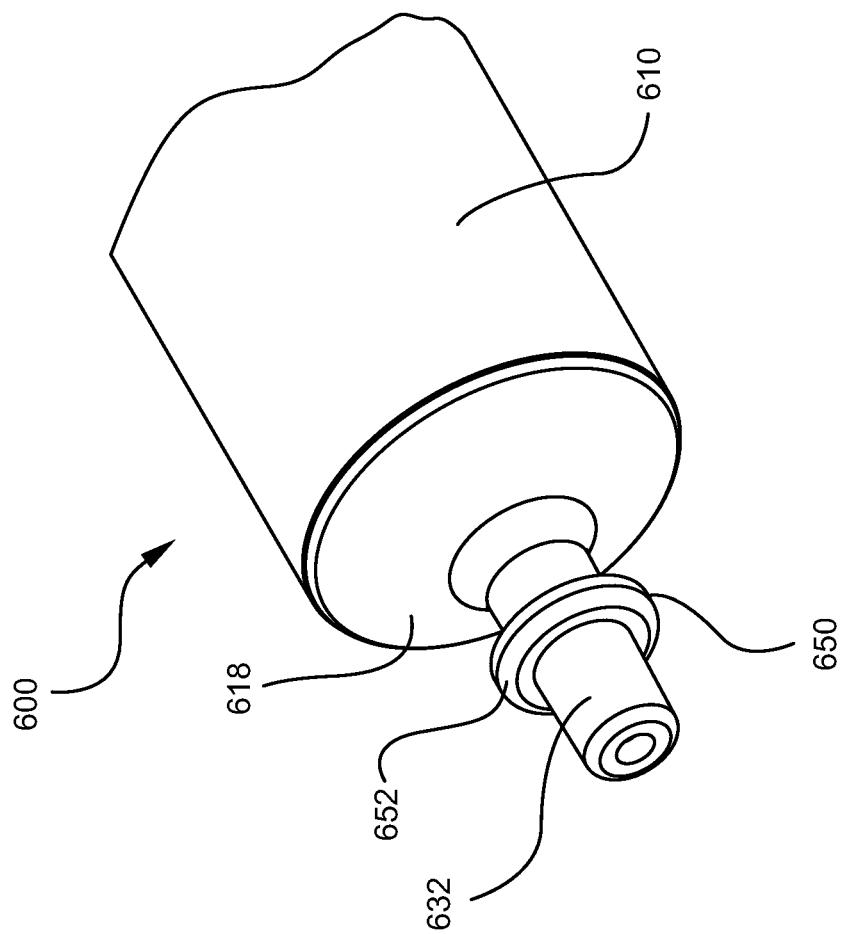
FIG. 35 illustrates a partial perspective view from a distal end of a container according to one or more embodiments of the present invention.
Figure 36:
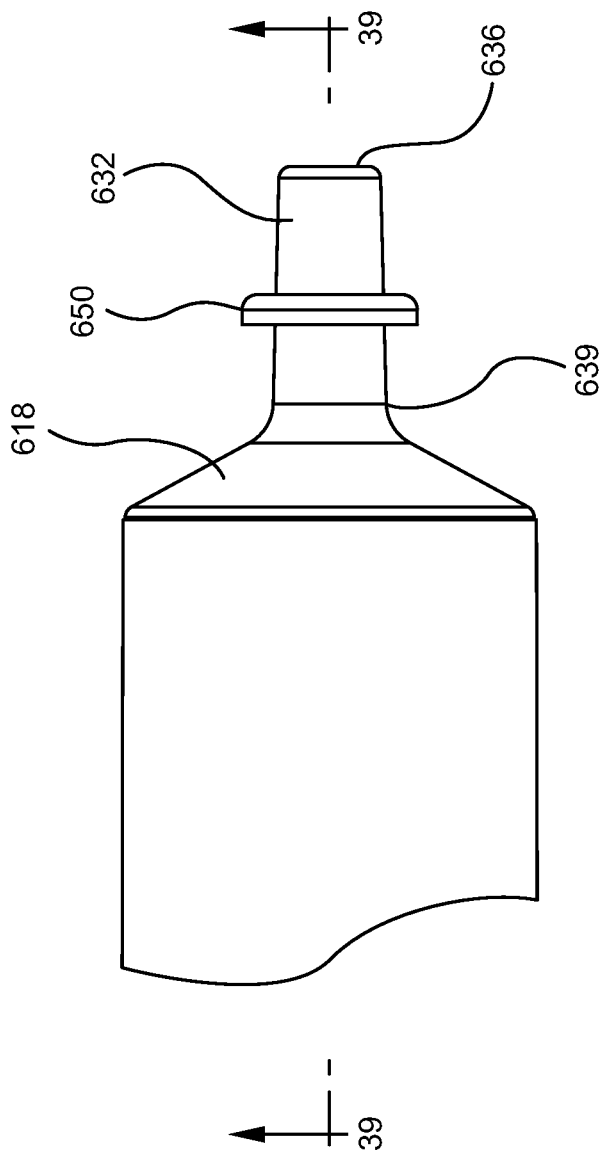
FIG. 36 illustrates a partial side elevational view of the container shown in FIG. 35.
Figure 38:
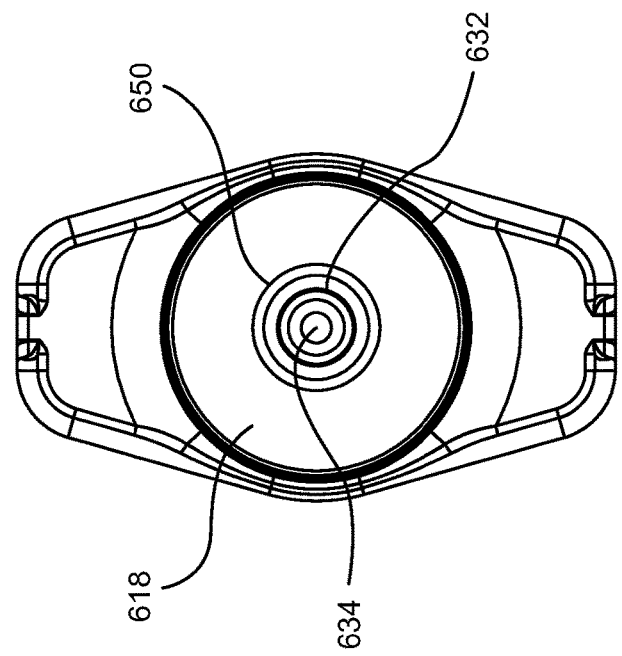
FIG. 38 illustrates a front elevational view of the container shown in FIG. 35.
Figure 37:
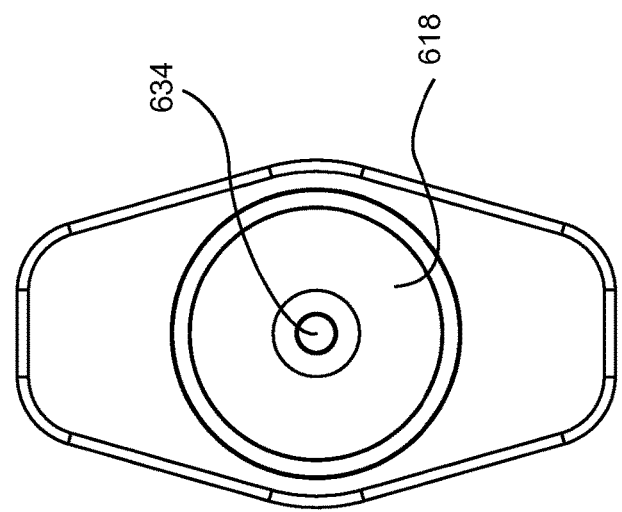
FIG. 37 illustrates a rear elevational view of the container shown in FIG. 35.
Figure 39:
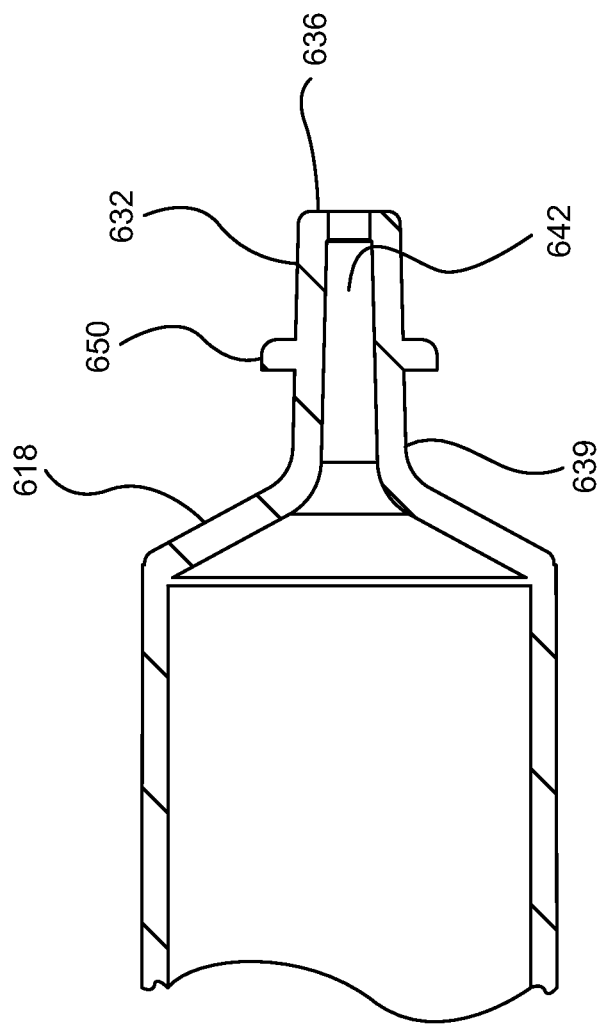
FIG. 39 illustrates an enlarged partial cross-sectional view of the container shown in FIG. 36 taken along line 39-39.
Figure 41:
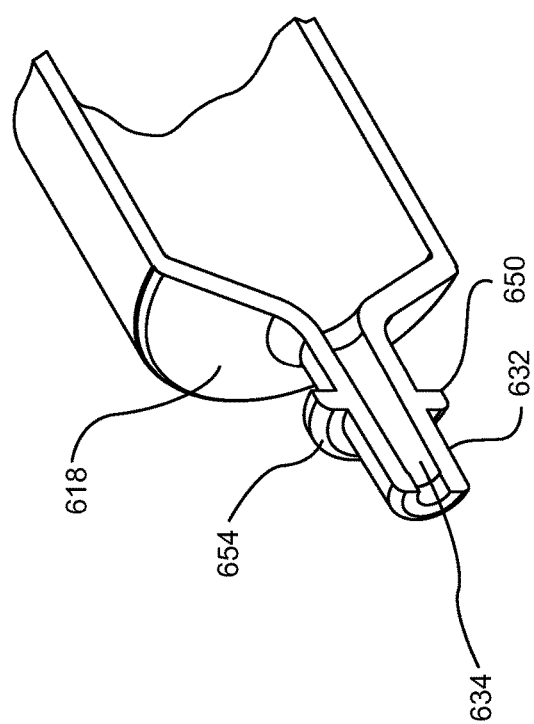
FIG. 41 shows a perspective view of the container shown in FIG. 39 taken from the distal end.
Figure 40:
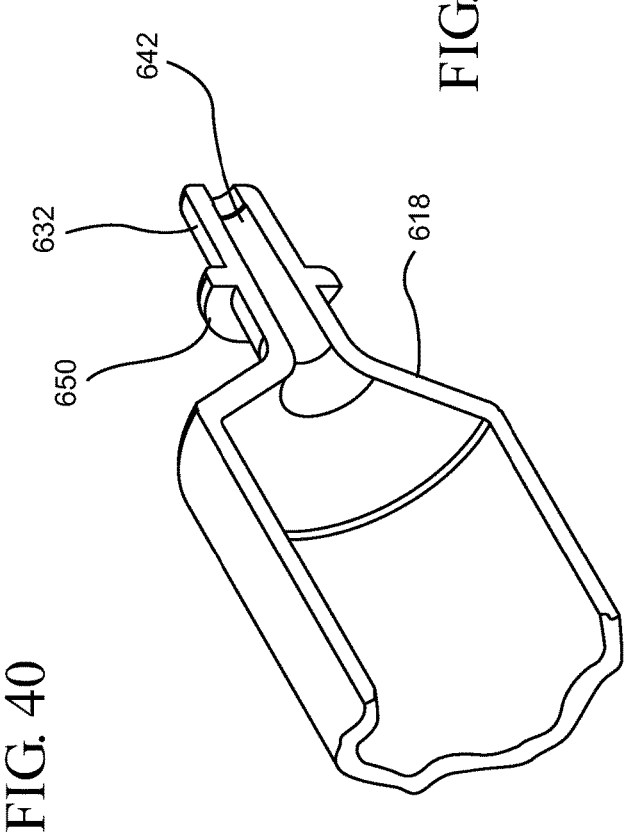
FIG. 40 illustrates a perspective view of the container shown in FIG. 39 taken from the proximal end.
Figure 42:
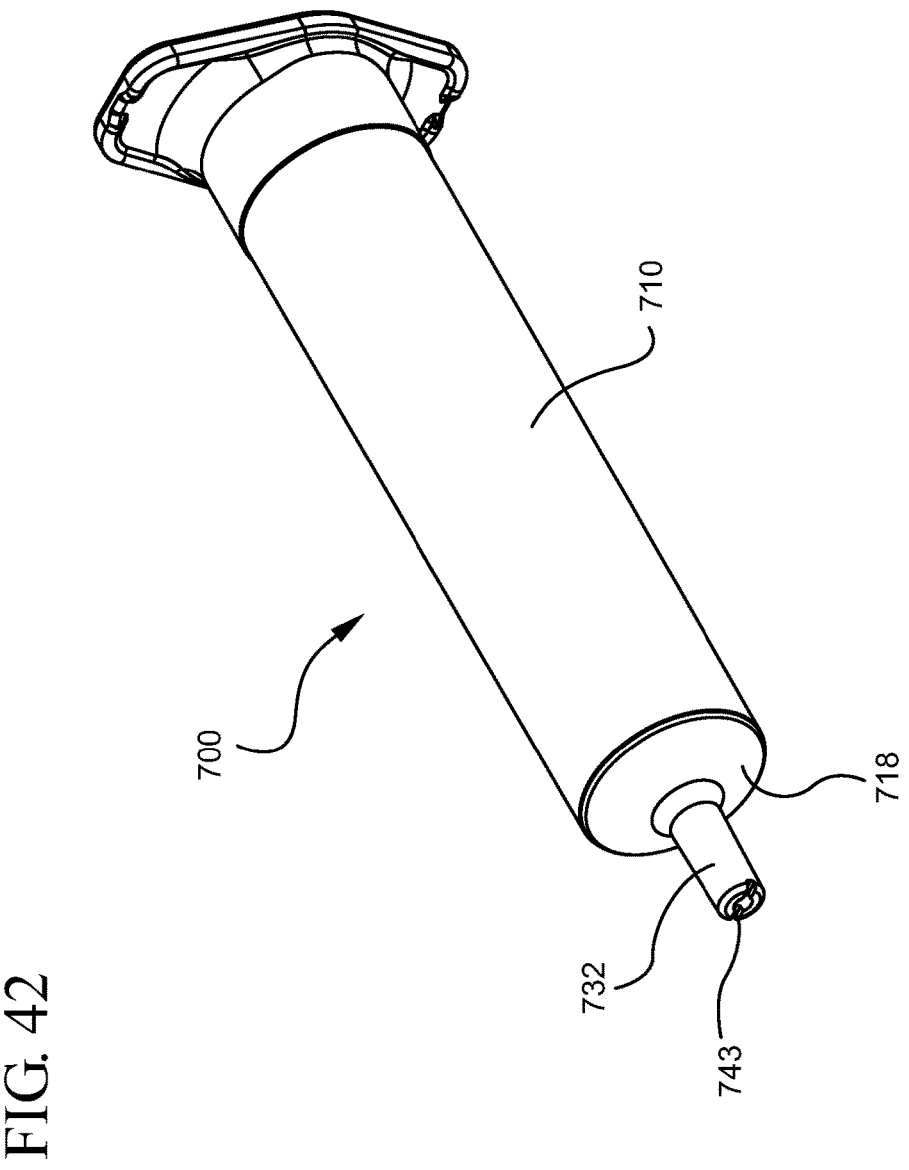
FIG. 42 illustrates a perspective view of a container according to one or more embodiments of the present invention.
Figure 43:
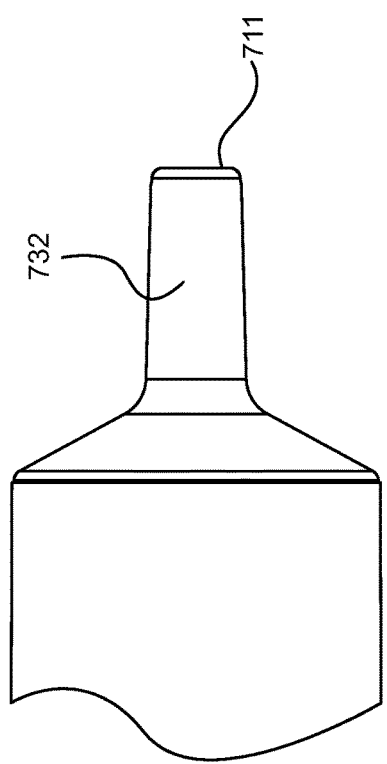
FIG. 43 illustrates an enlarged partial side elevational view of the container shown in FIG. 42.
Figure 44:
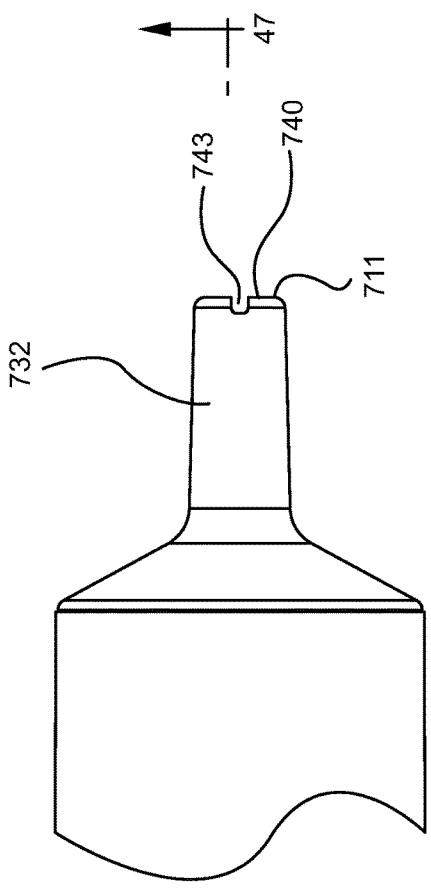
FIG. 44 illustrates a side elevational view of the container shown in FIG. 43, after rotating the container 90 degrees.
Figure 46:
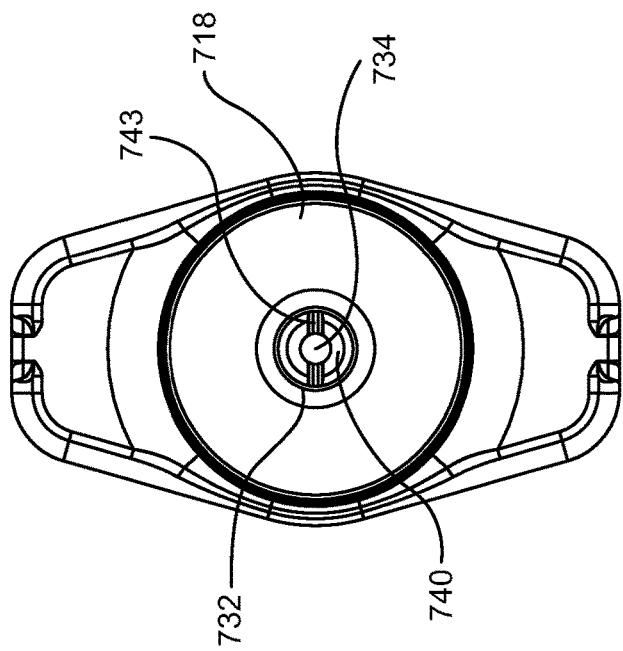
FIG. 46 illustrates a front elevational view of the container shown in FIG. 42.
Figure 45:
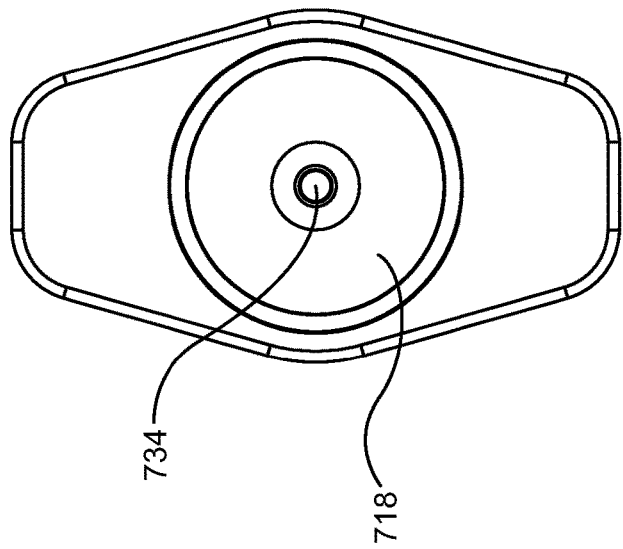
FIG. 45 illustrates a rear elevational view of the container shown in FIG. 42.
Figure 47:
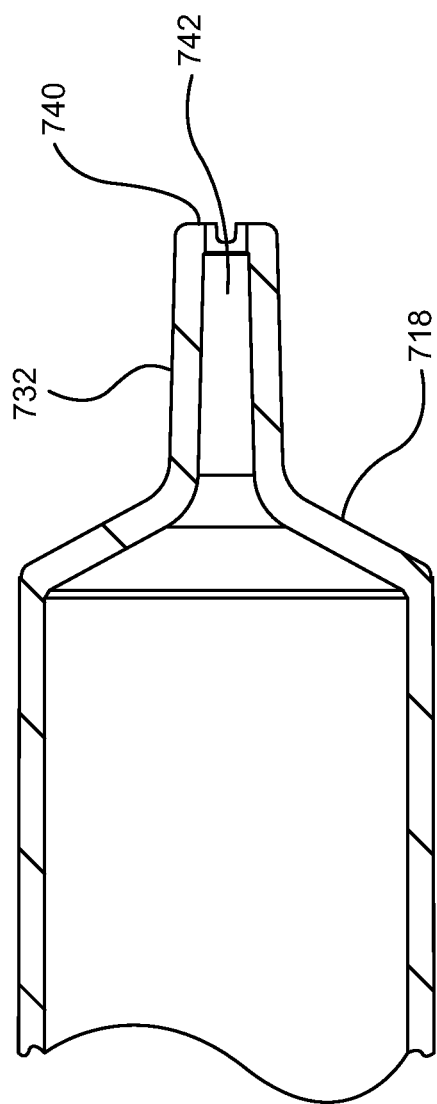
FIG. 47 illustrates a cross-sectional view of the container shown in FIG. 44 taken along line 47-47.
Figure 48:
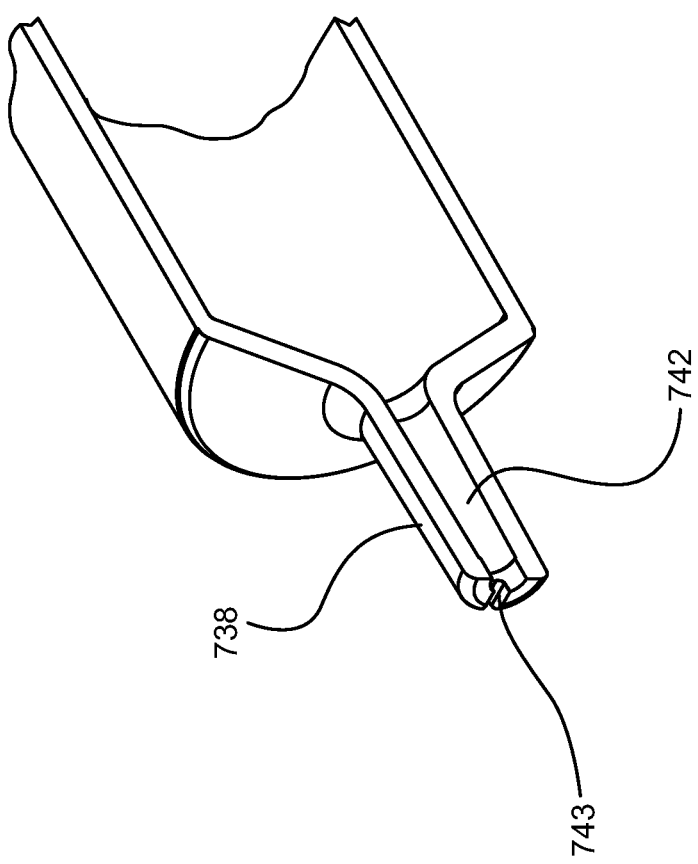
FIG. 48 shows a perspective view of the container shown in FIG. 47 taken from the distal end.
Figure 49:
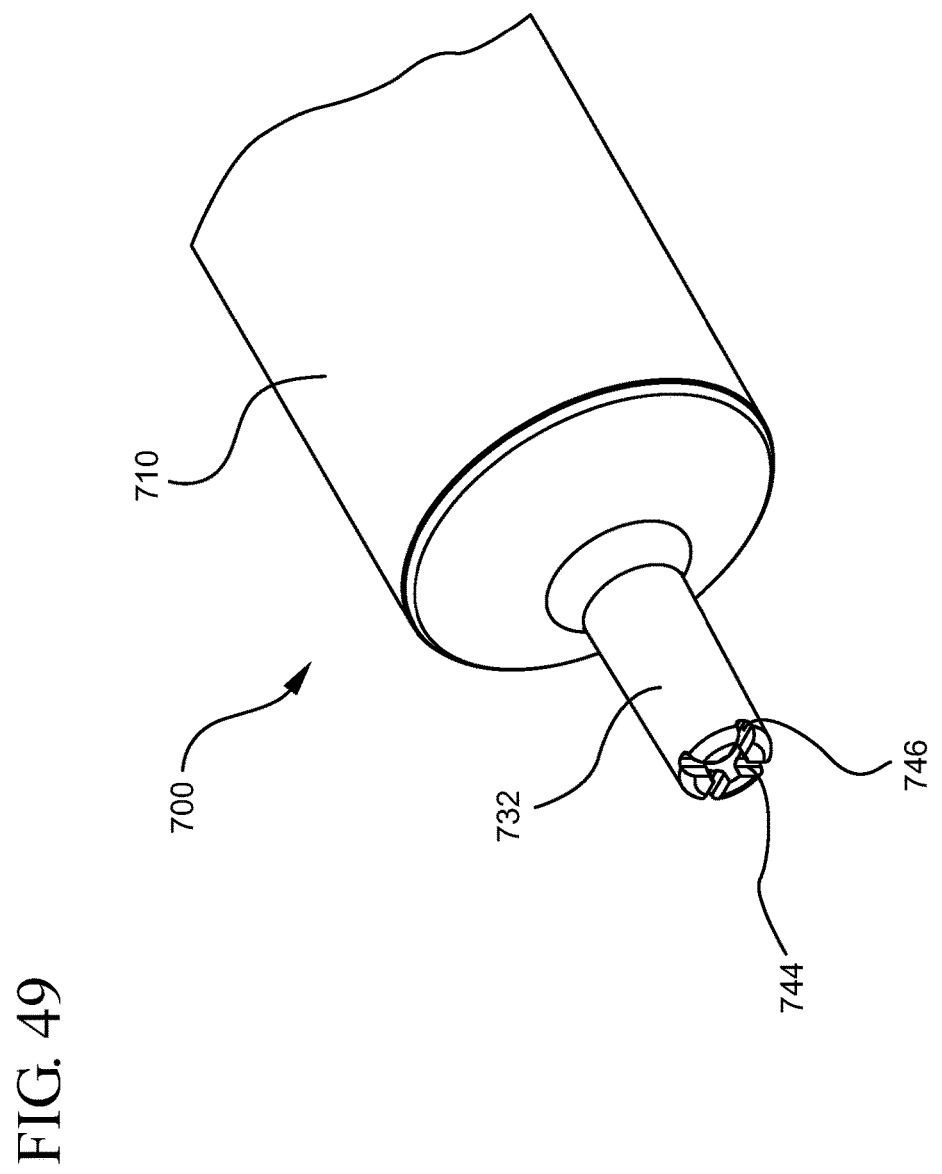
FIG. 49 illustrates an enlarged partial perspective view from a distal end of a container according to one or more embodiments of the present invention.
Figure 50:
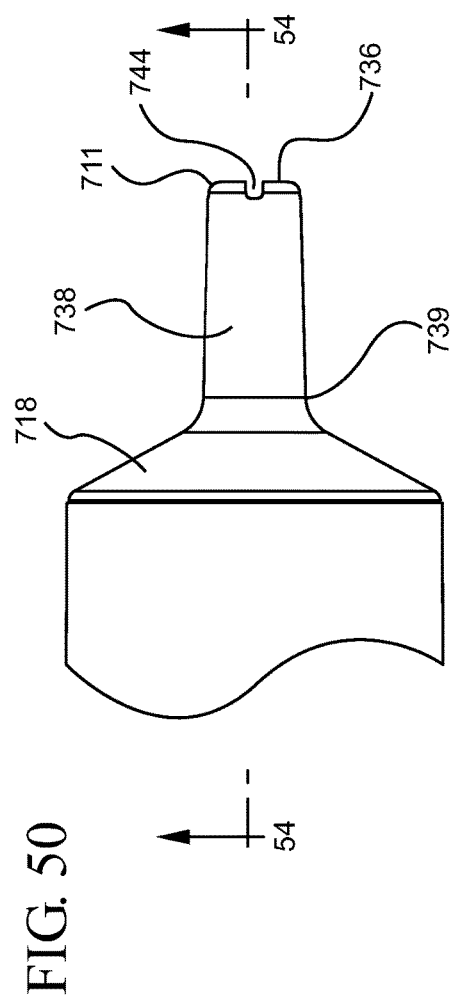
FIG. 50 illustrates an enlarged partial side elevational view of the container shown in FIG. 49.
Figure 51:
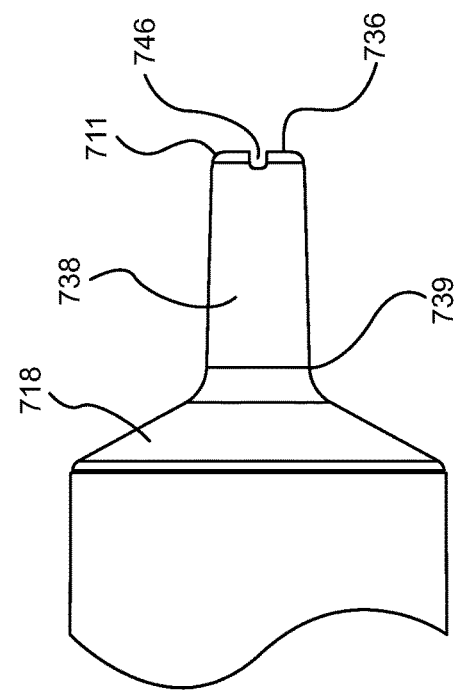
FIG. 51 illustrates a side elevational view of the container shown in FIG. 50, after rotating the container 90 degrees.
Figure 53:
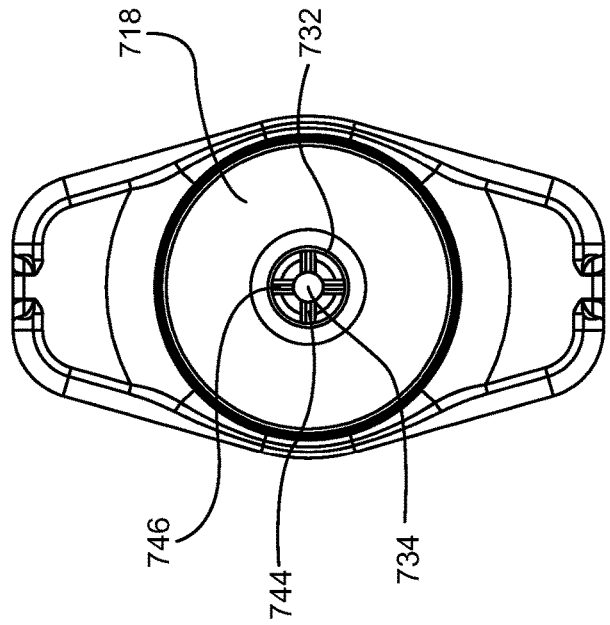
FIG. 53 illustrates a front elevational view of the container shown in FIG. 50.
Figure 52:
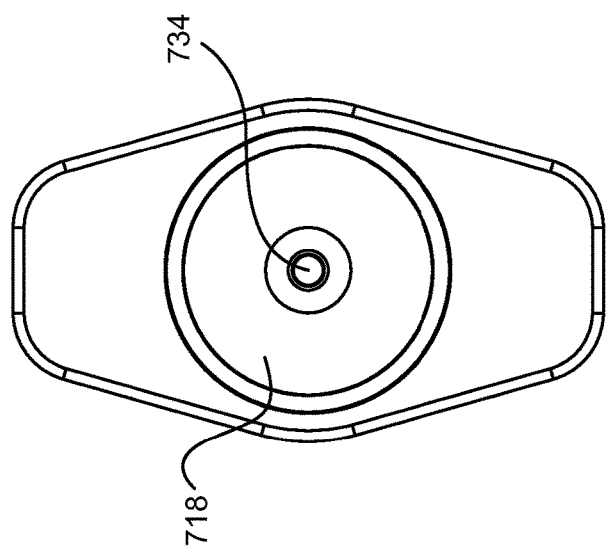
FIG. 52 illustrates a rear elevational view of the container shown in FIG. 50.
Figure 54:
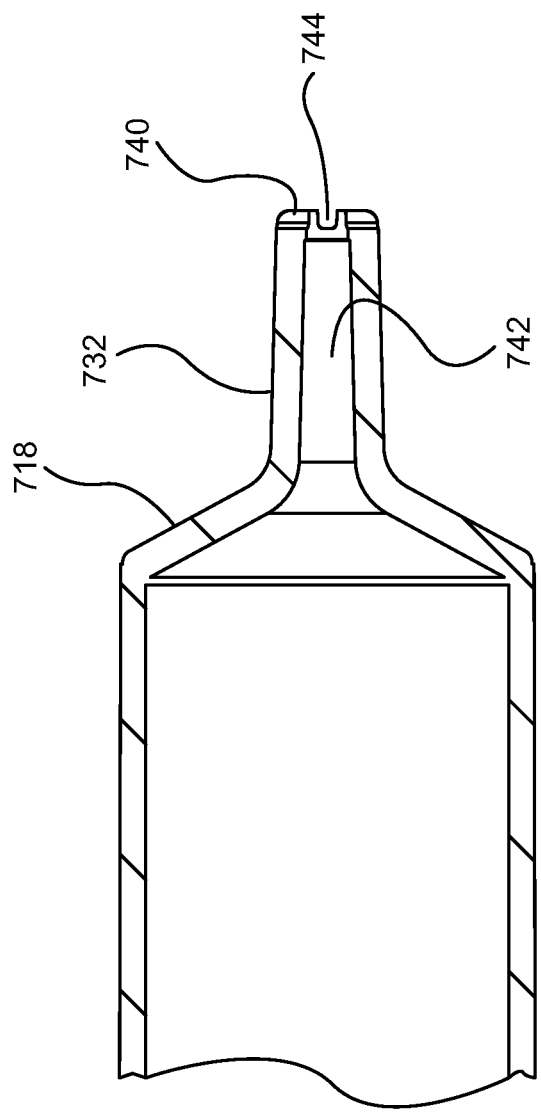
FIG. 54 illustrates a cross-sectional view of the container shown in FIG. 50 taken along line 54-54.
Figure 57:
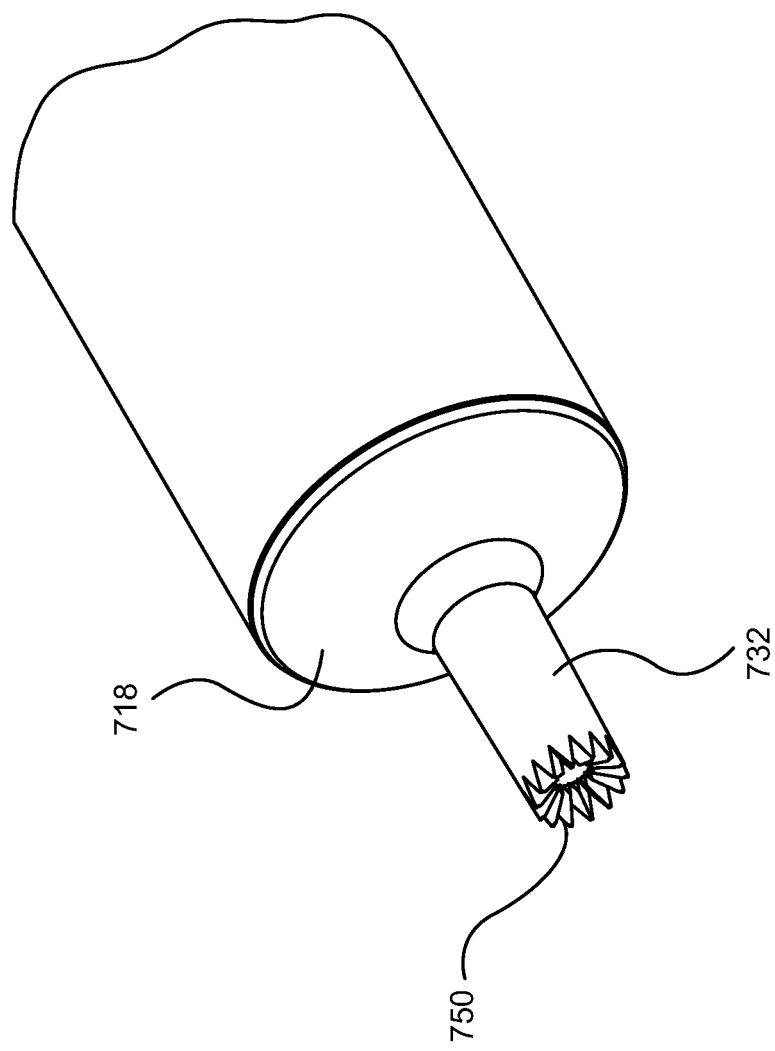
FIG. 57 illustrates an enlarged partial perspective view from a distal end of a container according to one or more embodiments of the present invention.
Figure 58:
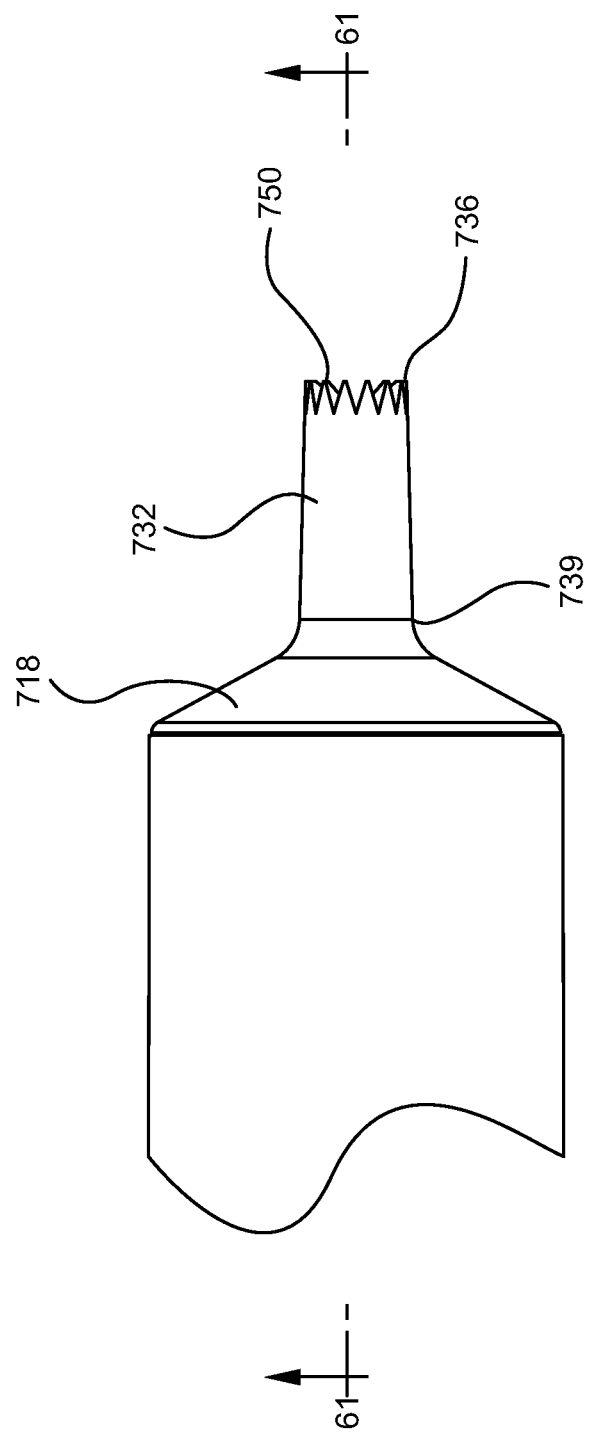
FIG. 58 illustrates a side elevational view of the container shown in FIG. 57.
Figure 60:
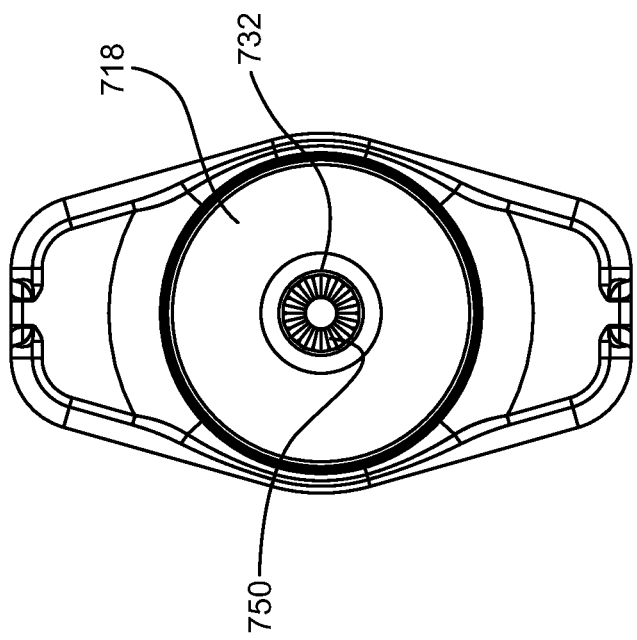
FIG. 60 illustrates a front elevational view of the container shown in FIG. 57.
Figure 59:
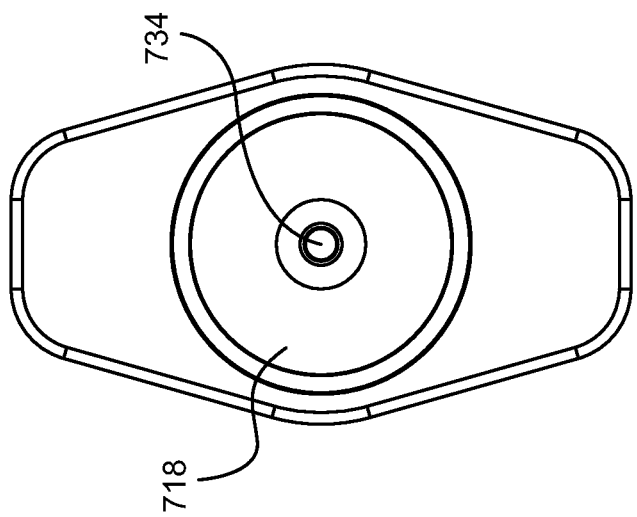
FIG. 59 illustrates a rear elevational view of the container shown in FIG. 57.
Figure 61:
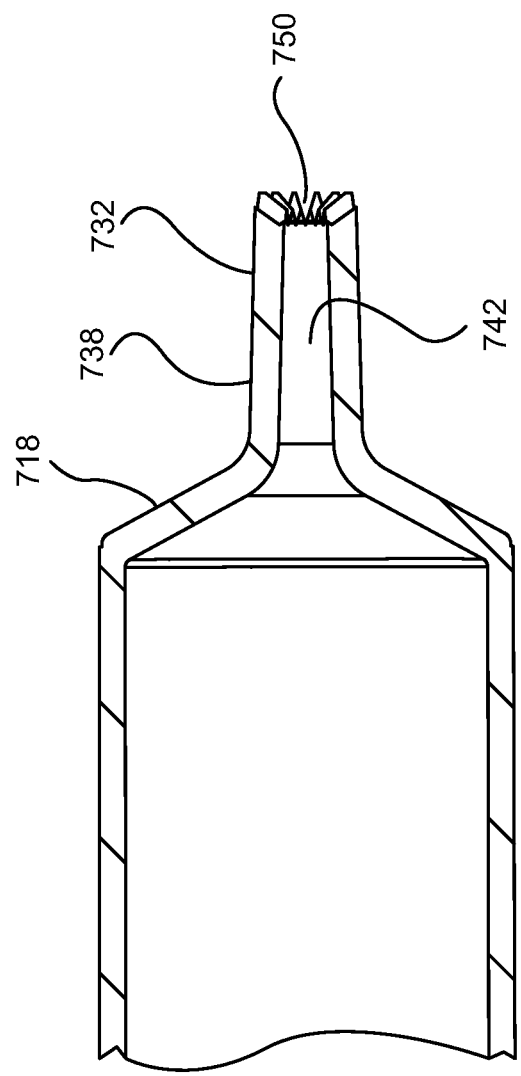
FIG. 61 illustrates an enlarged partial cross-sectional view of the container shown in FIG. 58 taken along line 61-61.
Figure 63:
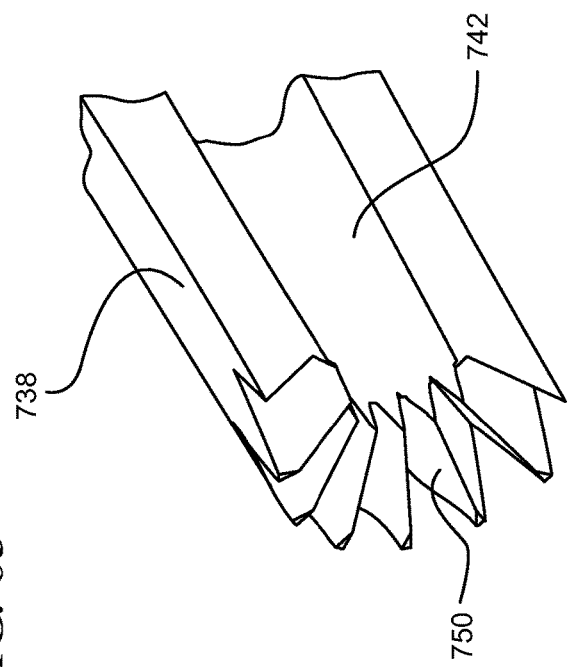
FIG. 63 illustrates an enlarged partial view of the tip of the container shown in FIG. 62.
Figure 62:
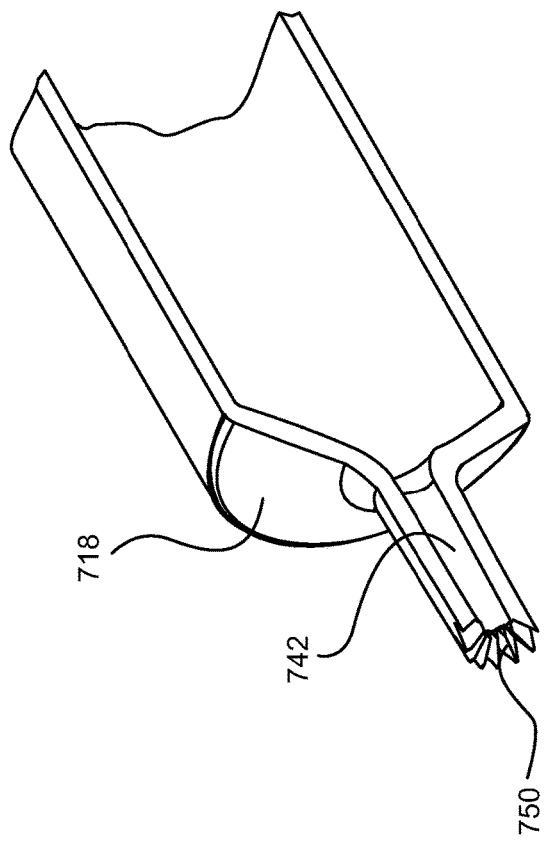
FIG. 62 shows an enlarged partial perspective view of the container shown in FIG. 61 taken from the distal end.

In one or more embodiments, as shown in FIGS. 29B and 29E, the non-luer element 550 may be provided as a continuous and singular barrier wall that extends continuously around the tip 532. In one or more embodiments, as shown in FIG. 29B, the non-luer element 550 may be provided as a uniform, continuous and singular barrier wall that extends continuously around the tip 532. In one or more embodiments, as shown in FIG. 29E, the non-luer element

550 may be provided as a continuous and singular barrier wall being flush with tip 532 having one or more curves or indentations that extends around the tip 532, where the tip 532 is visible through the curve or indentation of the collar. In the embodiment shown in FIGS. 29A, 29C, 29 D and 30-34, the non-luer element 550 is shown as a plurality of barrier walls 552 that form at least one aperture 557 or a plurality of apertures spaced between the barrier walls 552. In one or more embodiments, as shown in FIG. 29A, the apertures 557 of the embodiment shown extend from the distal end 558 to the proximal end 559 of the barrier wall. In one or more alternative embodiments, as shown in FIGS. 29 C and 29D, the apertures 557 may extend from the distal end 558 to a distance between the distal end 558 and the proximal end 559. In embodiments that incorporate apertures 557 in the barrier wall, in the event a standard female luer connector is able to fit over the barrier wall 552 such that the inside surface of the luer connector is in contact with the outside surface 556 of the barrier wall, the apertures 557 prevent or inhibit the formation of a fluid-tight seal by providing openings to the exterior of the connector that will result in leakage of fluid delivered through the tip. In one or more alternative embodiments, the aperture 557 provides visual indication of whether the non-luer element 550 functions similarly to a slip connector or a locking connector. In other words, the aperture 557 provides visual indication of whether the non-luer element 550 includes a luer slip fitting or a luer lock fitting. Specifically, the presence of the aperture 557 provides visual indication that the inside surface 554 of the barrier wall 552 is free of a plurality of threads or other locking feature that cooperates to lock a corresponding non-luer connector to the barrier wall 552. In one or more embodiments, the absence of the aperture 557 provides visual indication that the inside surface 554 of the barrier wall 552 includes a plurality of threads or other locking feature to lock a corresponding non-luer connector to the barrier wall 552.

In the embodiment shown, the barrier wall 552 is shown in the form of discrete walls that, when taken together, have a circular cross-section that forms a partial enclosure around the tip 532 that also has a circular cross-section. In one or more embodiments, the barrier wall 552 may have a triangular cross-section or other non-circular cross-section, which would prevent a standard female luer connector having a circular cross-section, for example the hub body 132 of FIGS. 1-3, from fitting or sliding within the channel 560 preventing the tip 532 and the inside surface 134 of the hub body 132 from forming an interference fit connection and/or fluid-tight engagement with the outside surface 538 of the tip 532. Accordingly, the non-luer element 550 prevents connection of a standard female luer connector, for example, the luer connector 133 of needle hub 130, to the syringe barrel 510.

In one or more alternative embodiments, the barrier wall 552 may have an outer cross-sectional dimension that is smaller than the inner cross-sectional dimension of a standard female luer connector. In such embodiments, the smaller outer cross-sectional dimension of the barrier wall 552 prevents sufficient contact between the inside surface 134 of the standard female luer connector and the outside surface 556 of the barrier wall 552 to form a interference fit connection and/or fluid-tight engagement there between. The barrier wall 552 may also have a length that prevents formation of an interference fit connection and/or fluid-tight engagement with a standard female luer connector, for example the luer connector 133 shown in FIG. 4. Specifically, the length of the barrier wall 552 may be too long or too short to permit fluid-tight engagement with the inside surface 134 of the luer connector 133.

As will be described below, the non-luer element 550 may have an outer cross-sectional dimension that permits connection to another corresponding non-luer connector. For example, the female non-luer connector 200 may have an exterior surface with an exterior cross-sectional dimension sized to fit within the channel 560 such that the inside surface 214 forms an interference fit connection and/or fluid-tight engagement with the outside surface 538 of the tip.

As described above with reference to FIGS. 23-28, the non-luer element 550 may also be utilized to prevent the user from forcing an incorrect interference fit connection and/or fluid-tight engagement between the tip 532 and a standard female luer connector when the female luer connector incorporates a soft or semi-rigid material, typically a rubber or elastomeric valve or seal. In such devices the rubber or elastomeric valve or seal may prevent the user from seeing leakage of the incorrect connection between the male and female connectors because the valve or seal conforms to the size and shape of the non-luer connector, sealing leaking fluid within the female luer connector. Such valves or seals are typically disposed within the hub cavity or on the inside surface of the hub cavity of standard female luer connectors. Standard female luer connectors with such valves or seals may be referred to as soft luer connectors or semi-rigid luer connectors. The valves or seals are typically utilized to allow the inside surface or the cavity of the standard female luer connector to conform to a variety of shapes. This prevents leakage between the male connector and the standard female connector due to insufficient formation of a fluid-tight seal between the standard female luer connector and a male connector. In such embodiments, the outer surface 538 of the tip 532 could potentially be connected to the standard female luer connector, with the valve or seal providing a seal between the tip 532 and the standard female luer connector. In one or more embodiments, the barrier wall 552 is shaped and/or sized to have inner cross-sectional dimension that prevents connection of a standard female luer connector that includes a valve or seal, as described above, to the tip 532. Specifically, the inner cross-sectional dimension of the barrier wall 552 is greater than the inner cross-sectional dimension of a standard female luer connector and less than the outer cross-sectional dimension of a standard female luer connector. Accordingly, an attempt to connect the standard female luer connector to the non-luer connector 500 will result in alignment of the hub body of the standard female luer connector with the barrier wall 552 such that the barrier wall 552 will physically block the tip 532 from penetrating the rubber or elastomeric valve or seal and therefore prevent the hub body of the standard female luer connector from attaching to the tip 532. Accordingly, the non-luer connector 500 minimizes the risk that a user can utilize the non-luer connector 500 described herein with an unintended standard female soft luer connector.

In use, to assemble the non-luer connector 500 to a correct, corresponding non-luer connector, for example, the female non-luer connector 200 shown in FIGS. 5-13, the wall 212 is inserted into the channel 560 between the barrier wall 552 and the tip 532 such that the tip 532 is disposed within the cavity 216. A force is applied in the distal direction on the syringe barrel 510 until the outside surface 538 of the tip engages the inside surface 214 of the wall of the female non-luer connector 200. In embodiments which utilize a threaded portion on the inside surface 554 of the barrier wall 552, the wall 212 of the female non-luer connector 200 is inserted into the channel 560 and rotated with respect to the syringe barrel 510 such that the tab 220 engages the threaded portion.

One or more embodiments of a non-luer connector 600 for use in a drug delivery device according to the second aspect of the present invention are shown in FIGS. 35-41. FIGS. 35-41 illustrate a non-luer connector 600 that includes a non-luer element 650 that prevents attachment of a standard female luer connector, for example needle hub 130 described above. The non-luer connector 600 of FIGS. 35-41 is shown integrally formed with a container in the form of a syringe barrel 610, as described above with reference to FIGS. 14-22. The container may be provided in other forms, for example, a drug bag, epidural pump or other containers known in the art. The syringe barrel 610 shown in FIGS. 35-41 includes a distal wall 618 and a tip 632 that extends in the distal direction from the distal wall 618. The tip 632 includes a passageway 642 and an opening 634 in fluid communication with the chamber of the syringe barrel 610. The tip 632 has a distal end 636 and a proximal end 639.

The outside surface 638 of the tip may have a dimension and/or shape that forms an interference fit connection and/or fluid-tight engagement with the outside surface of a corresponding non-luer connector, for example, the female non-luer connector 200. It will be appreciated, however, that the dimension and/or shape of the outside surface 638 of the tip according to the invention may permit the user to force an incorrect interference fit connection and/or fluid-tight engagement of the non-luer connector 600 with a standard female luer connector. As will be described below, the non-luer element 650 prevents such incorrect connection or engagement thereof. In one or more embodiments, the outside surface 638 of the tip has a dimension and/or shape that prevents forcing of an interference fit connection and/or fluid-tight engagement with a standard female luer connector but permits such connection and/or engagement with a corresponding non-luer connector.

In one or more embodiments, the outside surface 638 of the tip has an outer cross-sectional dimension as described with reference to FIGS. 29-34. In one or more embodiments, the outside surface 638 of the tip 632 may have a taper as also described with reference to FIGS. 29-34. The outside surface 638 of the tip 632 of one or more embodiments may have a length as described with reference to FIGS. 29-34.

The non-luer element 650 is integrally formed or provided in the container. Specifically, in the embodiment shown in FIGS. 35-41, the non-luer element 650 is integrally formed and disposed on outside surface 638 of the tip 632. The non-luer element 650 extends radially outwardly from the outside surface 638 of the tip. The non-luer element 650 includes an exterior surface 652 that defines an outer cross-sectional dimension that is greater than the outer cross-sectional dimension of the tip 632, when measured from the outside surface 638 of the tip. In the embodiment shown, the non-luer element 650 is shown as a circular disc having at least one narrowing edge 654.

The non-luer element 650 is disposed between the distal end 636 and a proximal end 639 of the tip 632. In the embodiment shown, the non-luer element 650 is disposed approximately at a mid-point between the distal end 636 and a proximal end 639. In one or more alternative embodiments, the non-luer element 650 may be disposed adjacent to or at the distal end 636 of the tip 632. Optionally, the non-luer element 650 may be disposed adjacent to or at the proximal end 639 of the tip 632.

The position of the non-luer element 650 in one or more embodiments may be modified to prevent connection of a standard female luer connector to the tip 632. Specifically, in one or more embodiments, the non-luer element 650 may be disposed closer to the distal end 636 of the tip 632 to allow fluid-tight engagement only of corresponding female non-luer connectors having an inside cavity of shorter length than the cavity of standard female luer connectors. Accordingly, the non-luer element 650 prevents the standard female luer connector from fully sliding in the proximal direction over the tip 632 and prevents formation of an interference fit connection and/or fluid-tight engagement between the standard female luer connector and the tip 632. That is, the standard female luer connector will contact the non-luer element 650 before it has been moved sufficiently proximally on the tip 632 to form a fluid-tight connection by contact of the outside surface 638 of the tip with the inner surface of the standard female luer connector.

The non-luer element 650 of the embodiment shown in FIGS. 35-41 has a cross-section that has an outer cross-sectional dimension that is greater than the inner cross-sectional dimension of a standard female luer connector, for example, the luer connector 133 of needle hub 130 shown in FIG. 4. Specifically, the outer cross-sectional dimension of the non-luer element 650 prevents the open proximal end of the standard female luer connector, for example, the hub body 132, from sliding over or fitting over the outside surface 638 of the tip and fully engaging the outside surface 638 of the tip 632. In other words, the non-luer element 650 functions as a barrier to movement of the luer connector over the tip 632 in the proximal direction.

In one or more embodiments, the outer cross-sectional dimension of the non-luer element 650 is in the range from about 0.175 inches to about 0.500 inches. In one or more specific embodiments, the outer cross-sectional dimension of the non-luer element 650 is in the range from about 0.175 inches to about 0.305 inches or from about 0.306 inches to about 0.500 inches. The upper limit of the outer cross-sectional dimension of the non-luer element 650 includes 0.300 inches, 0.302 inches, 0.304 inches, 0.306 inches, 0.308 inches and 0.310 inches. The lower limit of the cross-sectional dimension of the non-luer element 650 includes 0.170 inches, 0.172 inches, 0.174 inches, 0.176 inches, 0.178 inches and 0.180 inches.

In the embodiment shown in FIGS. 35-41, the non-luer element 650 may be provided as a continuous and singular disc-like structure that extends continuously circumferentially around the tip 632. In one or more embodiments, the non-luer element 650 may be provided in the form of discrete projections disposed around a portion of the circumference of the outside surface 538 of the tip 532. Spaces may be provided between the projections. In embodiments that incorporate discrete projections and/or spaces there between, in the event a standard female luer connector is able to fit over the non-luer element 650 such that the inside surface of the luer connector is in contact with the exterior surface 652 of the non-luer element 650, the spaces would prevent or inhibit the formation of a fluid-tight seal by providing areas of the non-luer element 650 and/or outside surface 638 of the tip that are not in contact with the inside surface of the luer connector. In one or more specific embodiments, the spaces would result in openings from the interior of the standard female luer connector to the outside surface 638 of the of the non-luer connector that would cause the fluid to leak.

In the embodiment shown, the non-luer element 650 has a circular cross-section. In one or more embodiments, the non-luer element 650 may have a square, triangular cross-section or other non-circular cross-section, which would prevent a standard female luer connector having a circular cross-section, for example the luer connector 133 of needle hub 130 of FIG. 4. Specifically, the hub body 132 of needle hub 130 would be prevented from fitting or sliding over the non-luer element 650 such that the tip 632 and the inside surface 134 of the hub body 132 would not be able to form an interference fit connection and/or fluid-tight engagement with the outside surface 638 of the tip 632. Accordingly, the non-luer element 650 prevents connection of a standard female luer connector to the syringe barrel 610 of the non-luer connector 600. Specifically, if the non-luer element 650 has a non-circular outer cross-sectional dimension that is smaller than the inner cross-sectional dimension of the standard circular female luer, there will be gaps in the contact points between the non-luer element 650 and/or tip 632 that would cause the fluid to leak.

As will be described below, the non-luer element 650 is positioned on the tip 632 to permit connection of the tip 632 to another corresponding non-luer connector. For example, the cavity 216 of a female non-luer connector 200 may have length that is equal to the length of the tip 632 from its distal end 636 to the non-luer element 650 such that the inside surface 214 forms an interference fit connection and/or fluid-tight engagement with the exterior surface 638 of tip 632. Accordingly, in one or more embodiments, the non-luer element 650 is positioned such that the length of the tip 632 between a point distally adjacent to the non-luer element 650 and the distal end 636 of the tip is less than or equal to the length of the cavity 216 of the female non-luer connector 200 to permit formation of an interference fit connection and/or fluid-tight engagement between the tip 632 and the female non-luer connector 200.

In one or more embodiments, the non-luer element 650 is positioned, shaped and/or sized to have an outer cross-sectional dimension that prevents connection of the tip 632 to a standard female luer connector that includes a valve or seal, as described above with reference to FIGS. 29-34. In one or more embodiments, the non-luer element 650 is positioned such that the standard female luer connector is prevented from sliding over the length of the tip 632 such that, upon penetration of the valve or seal by the tip 632, the opening 634 of the tip 632 remains adjacent or near the open proximal end of the standard female luer connector but does not enter the cavity sufficiently to cause any substantial contact between the outside surface of the tip 632 and the inside surface of the standard female luer connector. That is, the valve or seal of the standard female luer connector contacts the non-luer element 650 and prevents further proximal movement of the standard female luer connector before substantial contact between the tip 632 and the standard female luer connector is achieved. The position of the opening 634 compromises the sealing ability of the valve or seal disposed within the cavity of the standard female luer connector and visible leakage occurs despite the presence of the valve or seal. Accordingly, the non-luer connector 600 minimizes the risk that a user can inadvertently utilize the non-luer connector 600 described herein with an unintended standard female luer connector.

In use, to assemble the non-luer connector 600 to a corresponding non-luer connector, for example, the female non-luer connector 200 shown in FIGS. 5-13, the tip 632 of the non-luer connector 600 is disposed within the cavity 216 of the hub. A force is applied in the distal direction on the non-luer connector 600 until the outside surface 638 of the tip 632 engages the inside surface 214 of the wall of the female non-luer connector 200 in an interference fit connection and/or fluid-tight engagement.

One or more embodiments of a non-luer connector 700 for use in a drug delivery device according to the third aspect of the present invention are shown in FIGS. 42-63. FIGS. 42-63 illustrate a non-luer connector 700 that includes structure to prevent the formation of a fluid-tight connection between the non-luer connector 700 and a standard female luer connector by increasing the leakage or possibility of leakage of liquid in a misconnection. The non-luer connector 700 also has structure that enables attachment of the non-luer connector 700 to another corresponding non-luer connector, for example, the female non-luer connector 200. The non-luer connector 700 of FIGS. 42-63 is shown integrally formed to a container, provided in the form of a syringe barrel 710, as described above with reference to FIGS. 14-22. The container may be provided in other forms, for example, a drug bag, epidural pump and other containers known in the art. The syringe barrel 710 shown in FIGS. 42-63 includes a distal wall 718. A tip 732 extends in the distal direction from the distal wall 718 and includes a passageway 742 and an opening 734 in fluid communication with the chamber of the syringe barrel 710. The tip 732 has a distal end 736 and a proximal end 739. The tip includes an end wall 740 disposed at the distal end 736 that extends from the opening 734 to the outside surface 738 of the tip.

The outside surface 738 of the tip may have a dimension and/or shape that prevent the formation of a fluid-tight engagement with the inside surface of a standard female luer connector. In the embodiment shown, the tip 732 includes a non-luer element that is integrally formed thereon. Specifically, the end wall 740 includes a notch 743 or other structure for enlarging the opening 734 of the tip such that it extends to the outside surface 738 of the tip. In other words, the notch 743 provides a path for fluid to escape from the opening 734 to the outside surface 738 of the tip even when the end wall 740 is pressed against a flat surface, such as the end wall of the cavity of a standard female luer, provided that the inside surface 214 of the cavity 216 does not form a tight interference fit with the outside surface 738 of the non-luer tip 732. To accomplish this, the notch 743 extends from the passageway through the sidewall to form an aperture in the side wall at the distal end of the tip. The notch 743 may provide a beveled or curved edge to the distal end 736 of the tip 732 adjacent to the outside surface 738 of the tip that forms an aperture in the side wall at the distal end of the tip.

To establish fluid-tight engagement between the tip 732 and a hub or connector, regardless of whether the hub or connector has a standard female luer connector or female non-luer connector, a fluid-tight seal is typically formed between the outside surface 738 of the tip and inside surface of the female connector. If a fluid-tight seal is not formed between the inside surface of the female connector (i.e., the cavity) and the tip 732, a fluid-tight engagement will not be formed between the female connector and the tip 732. If fluid-tight engagement is not formed, leakage may or may not occur for the following reason.

In embodiments in which the outside surface 738 of a tip 732 has an outer cross-sectional dimension that prevents formation of a fluid-tight seal with the inside surface of a female connector cavity, the distal end 736 of the tip 732 may have a dimension that allows the end wall 740 of the tip 732 to contact the distal end of the inside surface of the cavity and potentially form at least a partially fluid-tight seal. That could allow a user to utilize the tip 732 with a standard female luer connector. In such situations, the leakage that may occur from the seal between the end wall 740 of the tip 732 and the distal end of the female connector cavity, even if only partial, may be too minimal to be noticed by the practitioner.

In the embodiment shown in FIGS. 42-63, the notch 743 disposed on the end wall 740 prevents the formation of a fluid-tight seal between the end wall 740 and the distal inside surface of a standard female luer hub, for example, the inside surface 134 of the needle hub 130, because it provides a larger outlet or avenue for leakage of the fluid within the container. The notch 743 thus prevents the formation of a fluid-tight seal at the end wall 740 of the tip 732 by providing an outlet into the side space between tip 732 and the hub even if end wall 740 of tip is in fluid-tight contact with the distal inside surface of the hub cavity. Accordingly, the notch 743 maximizes leakage between the tip 732 and the standard female luer connector if the connection there between is improper because a fluid-tight seal is not formed at the end wall 740 and the fluid is permitted to leak between the inside surface 134 of the hub and the outside surface 738 of the tip.

For a hub or connector to properly establish a fluid-tight engagement at the end wall 740, the female non-luer connector must have a dimension and/or shape to accommodate and enclose the notch 743. The inside surface 214 of female non-luer connector 200 may be shaped to have a taper which corresponds to the taper of the non-luer male tip, thus providing close contact between the outside surface of the tip and the inside surface of the female connector and substantially eliminating any space between them that could channel leaking fluid out of the female connector. This fully encloses or seals the notch 743 and prevents leakage of the fluid from the correct non-luer male-female connection.

The notch 743 has a dimension and/or shape that prevents the inside surface of a standard female luer connector from enclosing or sealing the notch 743. In one or more embodiments, the tip 732 may have a dimension, taper or shape that allows the notch 743 to be positioned or disposed in a manner in which the inside surface of a standard female luer connector cannot enclose or seal the notch 743. Specifically, in embodiments in which the outside surface 738 of the tip has a taper, length and/or outer cross-sectional dimension that prevents formation of a fluid-tight with a standard female luer connector, the notch 743 may be positioned, have a dimension or shape that prevents the inside surface of the standard female luer connector from contacting or sufficiently enclosing or sealing the notch 743. In one or more embodiments, the length of the tip 732 may be modified such that attachment of a standard female luer connector to the tip 732 creates dead space within the standard female luer connector and the tip 732 that prevents the formation of a seal between the standard female luer connector and the notch 743. In general, the notch will have a depth measured from the end wall 740 toward the proximal end 739 of the tip 732 that is sufficient to result in visible leakage into the dead space of an incorrect male-female connection but not large enough to cause a correct connection to leak in spite of adequate contact between the outside surface of the tip and the inside surface of the female cavity.

In one or more embodiments, the notch 743 has a depth measured from the end wall 740 toward the proximal end 739 of the tip 732 in the range from about 0.010 inches to about 0.100 inches. In one or more specific embodiments, the depth of the notch 743 may be in the range from about 0.01 inches to about 0.049 inches or from about 0.500 inches to about 0.100 inches. The upper limit of the depth of the notch 743 includes 0.040 inches, 0.042 inches, 0.044 inches, 0.046 inches, 0.048 inches, 0.050 inches, 0.052 inches, 0.054 inches, 0.056 inches, 0.058 inches and 0.060 inches. The lower limit of the depth of the notch 743 includes 0.005 inches, 0.006 inches, 0.007 inches, 0.008 inches, 0.009 inches, 0.012 inches, 0.014 inches, 0.016 inches, 0.018 inches and 0.02 inches. The notch 743 of one or more embodiments may have a width or cross-sectional dimension in the range from about 0.010 inches to about 0.080 inches. In one or more specific embodiments, the notch 743 has a width in the range from about 0.01 inches to about 0.049 inches or from about 0.05 inches to about 0.08 inches. The upper limit of the width of the notch 743 includes 0.040 inches, 0.042 inches, 0.044 inches, 0.046 inches, 0.048 inches, 0.050 inches, 0.052 inches, 0.054 inches, 0.056 inches, 0.058 inches and 0.060 inches. The lower limit of the width of the notch 743 may include, 0.005 inches, 0.006 inches, 0.007 inches, 0.008 inches, 0.009 inches, 0.012 inches, 0.014 inches, 0.016 inches, 0.018 inches and 0.02 inches.

The notch 743 of FIGS. 42-48 is shown as an indentation in the wall that extends through the width of the end wall 740. The notch 743 may be characterized as two notches that are disposed on opposite sides of the opening 734.

In the embodiment shown in FIGS. 49-56, the end wall 740 may include two notches 744,746. In the embodiment shown, the two notches 744, 746 are disposed at a right angle with respect to each other, when measured from the opening 734. In one or more alternative embodiments, additional notches may be added. The notches may be spaced at regular or irregular intervals from each other. The notch of FIGS. 49-56 may also be described as four separate notches that are disposed across the end wall 740 and which radiate outwardly from the opening 734. The four notches are shown as disposed at 90 degree intervals, when measured from the opening 734.

In the embodiment shown in FIGS. 57-63, the end wall 740 may include a plurality of notches 750 that are disposed adjacent to one another along the circumference of the distal end. The plurality of notches 750 surrounds the opening of the tip 732. The plurality of notches 750 have a wedge shape, wherein each of the plurality of notches 750 extends into the end wall 740 and forms a point. In other words, the plurality of notches has a zigzag profile. In one or more embodiments, each of the plurality of notches 750 have a first side 752 that has a decreasing slope that extends in the proximal direction into the end wall and a second side 754 that has an increasing slope that extends from the first side in the distal direction to the first side of an adjacent notch. An edge 755 connects the first side and the second side. The edge 755 is shown as being angled and/or having a slope that decreases from the outside surface 738 to the opening 734. The plurality of notches 750 may have a height that, when measured from the end wall 740 increases from the opening 734 to the outside surface 738 of the tip. In other words, the plurality of notches 750 may be angled toward the opening 734 of the tip.

In one or more embodiments, the angled plurality of notches 750 include a cutting edge 756 that is adapted to pierce or cut a valve or seal that may be utilized with a standard female luer connector, as described above with reference to FIGS. 29-34 and 35-41. Specifically, when a user attempts to assemble a standard female luer connector with a valve or seal to a non-luer connector 700, the cutting edge 756 of the plurality of notches cuts and/or pierces the valve or seal thereby preventing the valve or seal from minimizing the leakage between the improperly connected non-luer connector 700 and the standard female luer connector. In addition, the cutting edge 756 of one or more embodiments may also damage the standard female luer connector, further discouraging or preventing connection of a standard female luer connector to the non-luer connector 700. Accordingly, the cutting edge 756 minimizes the risk that a user can utilize the non-luer connector 700 described herein with an unintended standard female luer connector.

In one or more embodiments, the notch 743 disposed on the end wall 740 may be used in conjunction with a plurality of barrier walls 552 that form at least one aperture 557 or a plurality of apertures spaced between the barrier walls 552 to prevent the formation of a fluid-tight seal between the end wall 740 and the distal inside surface of a standard female luer hub by providing openings to the exterior of the connector that will result in leakage of fluid delivered through the tip. The apertures 557 of the embodiment extend from the distal end 558 to the proximal end 559 of the barrier wall. In one or more alternative embodiments, the apertures 557 may extend from the distal end 558 to a distance between the distal end 558 and the proximal end 559.

In one or more embodiments, the outside surface 738 of the tip may have an outer cross-sectional dimension and/or taper as described above with reference to FIGS. 29-34. The tip 732 of one or more embodiments may also have a length as described above with reference to FIGS. 29-34.

In use with a corresponding non-luer connector, for example, the female non-luer connector 200 of FIGS. 5-13, the tip 732 is inserted into the cavity 216 of the female non-luer connector 200. A force is applied to the syringe barrel 710 in the distal direction and/or to the female non-luer connector 200 in the proximal direction to cause the inside surface 214 of the wall 212 of the female non-luer connector to engage the outside surface 738 of the tip 723 in an interference fit connection and/or fluid-tight engagement. To remove the female non-luer connector 200 from the syringe barrel 710, a force is applied to the container in the proximal direction and/or to the female non-luer connector 200 in the distal direction to disengage the interference fit connection and/or the fluid-tight engagement of there between.

Figure 64:
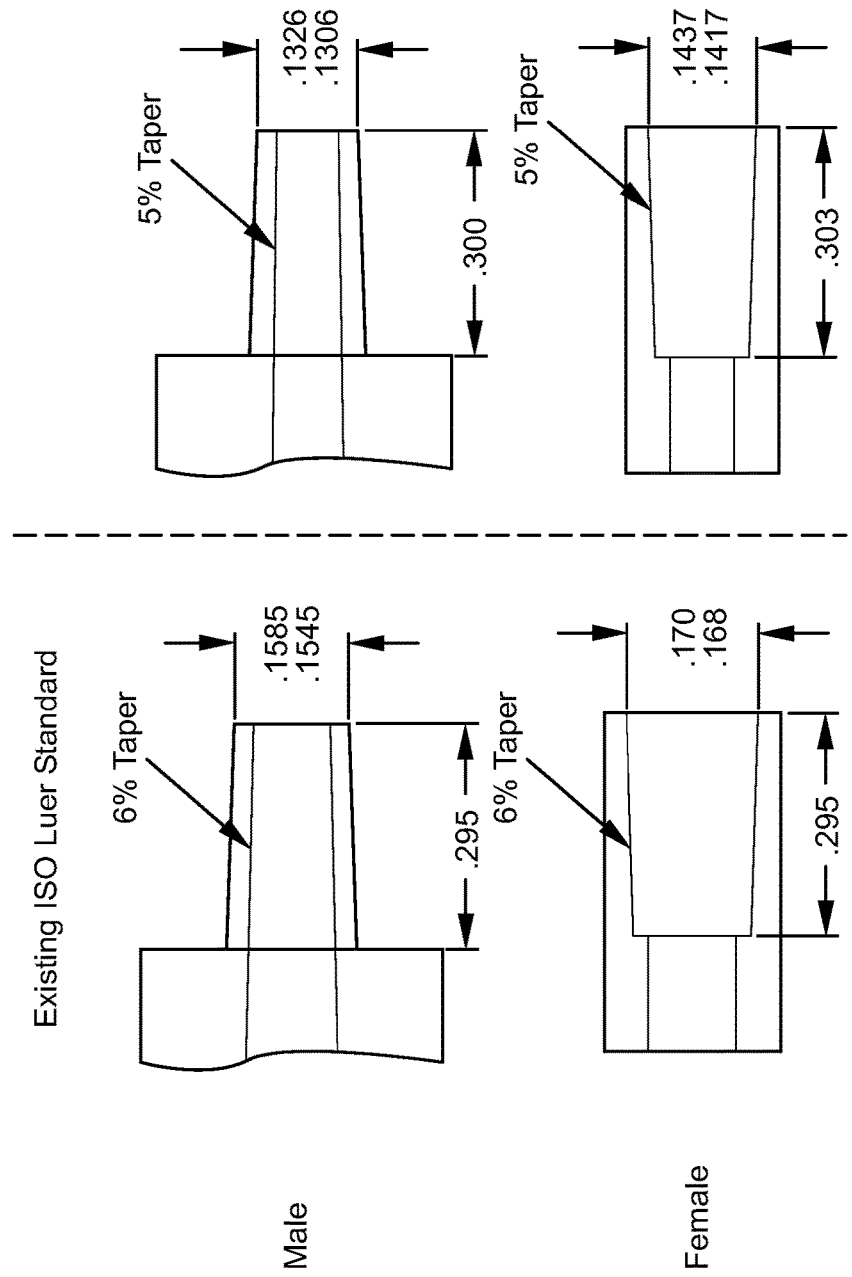
FIG. 64 show chart comparing the existing ISO standard for standard luer connectors according to the prior art and the proposed standard for male and female connectors for neuraxial applications.

In one or more embodiments, the notch 743, notches 744, 746 and plurality of notches 750 may be utilized with male connectors that will adopt proposed new standards for neuraxial applications. Specifically, under ISO 80369-6, for small bore connectors for liquids and gases in healthcare applications, the taper of the male connector and female connector will be modified from the existing ISO luer standard of 6% to 5% from their proximal ends to the distal ends. For male connectors, the new 5% taper provides a more gradual decrease in the outer cross-sectional dimension of the connector from the proximal end to the open distal end. For female connectors, the new 5% taper provides a more gradual decrease in the inner cross-sectional dimension of the connector from the open proximal end to the distal end, as shown in FIG. 64. In addition, the outer cross-sectional dimension at the open distal end of the male connector will be less than the range of the current ISO luer standard of 0.1545 inches to 0.1585 inches. Specifically, the current proposed ISO standards provide for the outer cross-sectional dimension for the male connector at the open distal end to measure in the range from about 0.1306 inches to about 0.1326 inches. The inner cross-sectional dimension of the female connector at the open proximal end will be less than the range of the current ISO luer standard of 0.168 inches to 0.170 inches. Specifically, the current proposed ISO standards provide for the inner cross-sectional dimension for the female connector at the open proximal end to measure in the range from about 0.1417 inches to about 0.1437 inches. The length of the male connector for neuraxial applications will also be increased from 0.295 inches to about 0.300 inches. The length of female connectors for neuraxial applications will also be increased from 0.295 inches to about 0.303 inches.

The more gradual taper in the new ISO standards for neuraxial applications for both male and female connectors and the smaller outer cross-sectional dimension and inner cross-sectional dimensions of the male and female connectors, respectively, are intended to prevent fluid tight connection of a male connector for a neuraxial application with a female standard luer connector and a female connector for a neuraxial application with a male standard luer connector. However, the smaller outer cross-sectional dimension of the male connector for neuraxial applications at the distal end thereof may make it possible for a user to inadvertently or purposely attach the male connector for neuraxial applications to a female standard luer connector, which may have an inner cross-sectional dimension at its distal end that could accommodate the smaller outer cross-sectional dimension of the male connector for neuraxial applications. The ability to attach the male connector for neuraxial applications to a female standard luer connector, even if not ideal, could allow the formation of at least a partial fluid-tight engagement sufficient to deliver unintended fluids or liquids to a patient at an incorrect delivery site.

The notch 743, notches 744, 746 and plurality of notches 750 described herein connect the opening 734 to the outside surface 738 of the tip, preventing partial fluid-tight connection between the distal end of the tip and the distal wall of a larger standard female connector, such that a user would not be able establish sufficient fluid-tight engagement to utilize a male connector for neuraxial applications that is incorrectly attached to a female standard luer connector. Specifically, the notches 743, notches 744, 746 and plurality of notches 750 increase leakage from such an incorrect connection and prevent circumvention of the new ISO proposals for neuraxial applications.

One or more embodiments of the present invention may incorporate a visual indicator to provide visual indication of the compatibility of the components of the drug delivery devices described herein. Specifically, a container having a non-luer connector may have a color or be made from a colored polymeric material that corresponds to the color of a correct corresponding female non-luer connector. In one or more embodiments, the plunger rod of a syringe may also have a color that corresponds to a correct corresponding female non-luer connector. The visual indicators may be placed on the hub body and/or the needle shield of the female non-luer connector. Other visual indicators may include labeling that conveys that the container and/or female non-luer connector include a non-luer connector.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A non-luer connector for connection to a second non-luer connector, the non-luer connector comprising:
an open distal end, an open proximal end, a proximal wall extending distally from the open proximal end, the proximal wall including an inside surface defining a cavity for receiving at least a portion of the second non-luer connector, and an attachment end extending from the proximal wall, the attachment end including a first narrowed wall extending from the proximal wall to a second narrowed wall disposed distally adjacent to the first narrowed wall, a third narrowed wall disposed distally adjacent to the second narrowed wall and extending to the open proximal end, an inner cross-sectional dimension of the first narrowed wall being less than an inner cross-sectional dimension of the inside surface of the proximal wall, the second narrowed wall having an inner cross-sectional dimension that is less than the inner cross-sectional dimension of the first narrowed wall, the third narrowed wall having an inner cross-sectional dimension that is less than the inner cross-sectional dimensions of the proximal wall, the first narrowed wall and the second narrowed wall; a length of a cavity measured from the open proximal end to an end of the second narrowed wall, but not including the second narrowed wall, being in the range from about 0.200 inches to 0.500 inches, the inside surface of the proximal wall having a taper in the range from 0.5% to 5.9% decreasing in a proximal to distal direction, an outside surface with a radially outwardly extending rim disposed around an entire circumference of the outside surface at the open proximal end of the non-luer connector, the radially outwardly extending rim including a radially outwardly extending tab disposed along at least a portion of the rim, the outside surface including two arms disposed on opposite sides of the non-luer connector that extend from the first narrowed wall to a location adjacent to the open distal end, an annular disc disposed adjacent to the two arms that extends radially outwardly from the outside surface, the third narrowed wall including four protrusions that extend radially outwardly from the outside surface and extend from the annular disc to the open distal end along a same axis.

2. The non-luer connector of claim 1, wherein the inner cross-sectional dimension of the proximal wall is in the range from about 0.100 inches to about 0.145 inches.

3. The non-luer connector of claim 1, wherein the inner cross-sectional dimension of the proximal wall is in the range from about 0.1306 inches to about 0.1326 inches.

4. The non-luer connector of claim 1, wherein the taper decreasing in a proximal to distal direction is in the range from about 3.0% to 5.9%.

5. The non-luer connector of claim 1, wherein the second non-luer connector comprises a hub body including an open proximal end, an interior surface defining a cavity with an inner cross-sectional dimension measured at the open proximal end of the hub body of less than 0.168 inches and a needle cannula attached to the hub body.

6. The non-luer connector of claim 5, wherein the inner cross-sectional dimension of the cavity of the hub body at the open proximal end is in the range from about 0.110 inches to about 0.150 inches.

7. The non-luer connector of claim 6, wherein the inner cross-sectional dimension of the cavity of the hub body measured at the open proximal end is in the range from about 0.1417 inches to about 0.1437 inches.

8. The non-luer connector of claim 5, wherein the inside surface of the proximal wall has one of a non-circular cross-section, a square cross-section and a triangular cross-section shape and the inner cross-sectional dimension of the inside surface of the proximal wall is selected to form a fluid-tight seal with an elongate tip of a container.

9. The drug delivery device of claim 5, wherein an inner cross-sectional dimension of the cavity for receiving at least a portion of the second non-luer connector is selected to form a fluid-tight seal with an elongate tip of a container.

10. The non-luer connector of claim 1, wherein the cavity for receiving at least a portion of the second non-luer connector has a length in the range from about 0.250 inches to about 0.500 inches.

11. The non-luer connector of claim 1, wherein the taper of the inside surface of the proximal wall is in the range from about 3% to 5.9%.

12. The non-luer connector of claim 1, wherein the inside surface of the proximal wall has one of a non-circular cross-section, a square cross-section and a triangular cross-section shape.

* * * * *